US012758533B2

(12) United States Patent
Johnson et al.

(10) Patent No.: US 12,758,533 B2
(45) Date of Patent: Oct. 13, 2026

(54) NANOPARTICLES FOR DELIVERY OF THERAPEUTICS TO THE EYE FOR TREATMENT OF GLAUCOMA

(71) Applicant: Northwestern University, Evanston, IL (US)

(72) Inventors: Mark Johnson, Evanston, IL (US); Amir Vahabikashi, Evanston, IL (US); Trevor Stack, Evanston, IL (US); Michael Patrick Vincent, Evanston, IL (US); Evan Alexander Scott, Evanston, IL (US)

(73) Assignee: Northwestern University, Evanston, IL (US)

( * ) Notice: Subject to any disclaimer, the term of this patent is extended or adjusted under 35 U.S.C. 154(b) by 295 days.

(21) Appl. No.: 18/577,632

(22) PCT Filed: Jul. 11, 2022

(86) PCT No.: PCT/US2022/073598
§ 371 (c)(1),
(2) Date: Jan. 8, 2024

(87) PCT Pub. No.: WO2023/283656
PCT Pub. Date: Jan. 12, 2023

(65) Prior Publication Data

US 2024/0307358 A1 Sep. 19, 2024

Related U.S. Application Data

(60) Provisional application No. 63/203,128, filed on Jul. 9, 2021.

(51) Int. Cl.

| | |
|---|---|
| ***A61K 31/427*** | (2006.01) |
| ***A61K 9/00*** | (2006.01) |
| ***A61K 9/107*** | (2006.01) |
| ***A61K 9/14*** | (2006.01) |
| ***A61P 27/06*** | (2006.01) |

(52) U.S. Cl.
CPC .......... *A61K 31/427* (2013.01); *A61K 9/0051* (2013.01); *A61K 9/107* (2013.01); *A61K 9/146* (2013.01); *A61P 27/06* (2018.01)

(58) Field of Classification Search
None
See application file for complete search history.

(56) References Cited

U.S. PATENT DOCUMENTS

| | | | | |
|---|---|---|---|---|
| 10,633,493 | B2 | 4/2020 | Scott et al. | |
| 10,829,752 | B2 | 11/2020 | Satchell | |
| 11,202,823 | B2 | 12/2021 | Scott et al. | |
| 11,737,978 | B2 | 8/2023 | Scott et al. | |
| 2019/0388559 | A1 * | 12/2019 | Eixenberger | A61K 9/0009 |
| 2021/0052498 | A1 | 2/2021 | Scott et al. | |
| 2021/0106697 | A1 | 4/2021 | Scott et al. | |
| 2021/0308065 | A1 | 10/2021 | Scott et al. | |
| 2022/0047719 | A1 | 2/2022 | Scott et al. | |
| 2022/0119510 | A1 | 4/2022 | Scott et al. | |
| 2022/0401367 | A1 | 12/2022 | Scott et al. | |
| 2023/0330022 | A1 | 10/2023 | Scott et al. | |

FOREIGN PATENT DOCUMENTS

| | | | | |
|---|---|---|---|---|
| CN | 111617036 | A * | 9/2020 | A61K 31/56 |
| WO | WO-2019217459 | A1 * | 11/2019 | C12Y 115/01001 |
| WO | 2020206307 | A1 | 10/2020 | |
| WO | 2023283656 | A1 | 1/2023 | |

OTHER PUBLICATIONS

Shi et al.; Identification of high-affinity VEGFR3-binding peptides through a phage-displayed random peptide library; Cross Mark; J Gynecol Oncol vol. 26, No. 4:327-335 http://dx.doi.org/10.3802/jgo.2015.26.4.327 pISSN 2005-0380 • eISSN 2005-0399 (2015) (Year: 2015).*

Shi et al.; Identification of high-affinity VEGFR3-binding peptides through a phage-displayed random peptide library; Cross Mark; J Gynecol Oncol vol. 26, No. 4:327-335 http://dx.doi.org/10.3802/jgo.2015.26.4.327 pISSN 2005-0380 • eISSN 2005-0399 (2015) Manuscript (Year: 2015).*

Yi et al.; Surface Engineered Polymersomes for Enhanced Modulation of Dendritic Cells During Cardiovascular Immunotherapy; Wiley-VCH Verlag GmbH & Co. KGaA, Weinheim; Adv. Funct. Mater. 2019, 29, 1904399 (16 pgs.) (Year: 2019).*

Machine translation CN111617036A (Year: 2020).*

Is latrunculin a cell softening agent—Google Search (Year: 2025).*

Latrunculin a and eye—Google Search (Year: 2025).*

What is a latrunculin a administration molarity—Google Search (Year: 2025).*

Canal of Schlemm_ Location, function, glaucoma _ Kenhub (Year: 2023).*

VEGFR-3_FLT-4 receptor and the SC cells which express this lymphatic lineage receptor—Google Search (Year: 2025).*

Stack. "Modulation of Schlemm's Canal Endothelial Cell Stiffness via Latrunculin Loaded BlockCopolymer Micelles" 1-16. Biomedical Materials Research. Web. Mar. 6, 2018. Entire document; DOI: 10.1002/jbm.a/36376.

Vincent. "Surface Engineering of FLT4-Targeted Nanocarriers Enhances Cell-Softening Glaucoma Therapy" 32823-32836. Applied Materials and Interfaces. Web. Jul. 7, 2021; Abstract, p. 32824, col. 1, Paragraph 3, p. 32825, col. 1, Paragraph 3, p. 32828, Table 2; DOI: https://doi.org/10.1021/acsami.1c09294.

(Continued)

*Primary Examiner* — Robert A Wax
*Assistant Examiner* — John W Lippert, III
(74) *Attorney, Agent, or Firm* — Quarles & Brady LLP

(57) ABSTRACT

The present invention provides systems for targeted delivery of therapeutic agents to Schlemm's canal (SC) endothelial cells. Also provided are methods for using the systems to treat glaucoma or reduce intraocular pressure.

18 Claims, 32 Drawing Sheets

Specification includes a Sequence Listing.

(56) References Cited

OTHER PUBLICATIONS

Yi. "Surface engineered polymersomes for enhanced modulation of dendrilic cells during cardiovascular immunotherapy" 1-34. Advanced Functional Materials. Web. Oct. 17, 2019; Abstract, p. 34, Table 1, Rows 4-10; DOI: 10.1002/adfm.201904399.
International Search Report for PCT/US2022/073598 mailed Oct. 19, 2022.
Stack, Trevor, et al. "Targeted delivery of cell softening micelles to Schlemm's canal endothelial cells for treatment of glaucoma." Small 16.43 (2020): 2004205.
Stamer, W. Daniel, et al. "Isolation, culture, and characterization of endothelial cells from Schlemm's canal." Investigative ophthalmology & visual science 39.10 (1998): 1804-1812.
Sterling, Teague, and John J. Irwin. "ZINC 15-ligand discovery for everyone." Journal of chemical information and modeling 55.11 (2015): 2324-2337.
Swaminathan, Swarup S., et al. "Secreted protein acidic and rich in cysteine (SPARC)-null mice exhibit more uniform outflow." Investigative ophthalmology & visual science 54.3 (2013): 2035-2047.
Tanihara, Hidenobu, et al. "Phase 2 randomized clinical study of a Rho kinase inhibitor, K-115, in primary open-angle glaucoma and ocular hypertension." American journal of ophthalmology 156.4 (2013): 731-736.
Tham, Yih-Chung, et al. "Global prevalence of glaucoma and projections of glaucoma burden through 2040: a systematic review and meta-analysis." Ophthalmology 121.11 (2014): 2081-2090.
Thomasy, Sara M., et al. "Substratum stiffness and latrunculin B regulate matrix gene and protein expression in human trabecular meshwork cells." Investigative ophthalmology & visual science 53.2 (2012): 952-958.
Tripathi, Ramesh C., Charles B. Millard, and Brenda J. Tripathi. "Protein composition of human aqueous humor: SDS-PAGE analysis of surgical and post-mortem samples." Experimental eye research 48.1 (1989): 117-130.
Van Zyl, Tavé, et al. "Cell atlas of aqueous humor outflow pathways in eyes of humans and four model species provides insight into glaucoma pathogenesis." Proceedings of the National Academy of Sciences 117.19 (2020): 10339-10349.
Velluto, Diana, et al. "PEG-b-PPS-b-PEI micelles and PEG-b-PPS/PEG-b-PPS-b-PEI mixed micelles as non-viral vectors for plasmid DNA: tumor immunotoxicity in B16F10 melanoma." Biomaterials 32.36 (2011): 9839-9847.
Vincent, Michael P., et al. "The combination of morphology and surface chemistry defines the immunological identity of nanocarriers in human blood." Advanced therapeutics 4.8 (2021): 2100062.
Wilson, A. M., and A. Di Polo. "Gene therapy for retinal ganglion cell neuroprotection in glaucoma." Gene therapy 19.2 (2012): 127-136.
Zhang, Xian, et al. "In vivo imaging of Schlemm's canal and limbal vascular network in mouse using visible-light OCT." Investigative ophthalmology & visual science 61.2 (2020): 23-23.
Zhou, E. H., et al. "Mechanical responsiveness of the endothelial cell of Schlemm's canal: scope, variability and its potential role in controlling aqueous humour outflow." Journal of The Royal Society Interface 9.71 (2012): 1144-1155.
Du, F., et al., (2019): Homopolymer Self-Assembly via Poly(propylene Sulfone) Networks. ChemRxiv. Preprint.
Du F. et al., Sequential intracellular release of water-soluble cargos from Shell-crosslinked polymersomes. J Control Release. 2018; 282:90-100.
E. Garcia-Valenzuela, S. Shareef, J. Walsh, S. C. Sharma, Exp Eye Res 1995, 61, 33.
L. A. Kerrigan, D. J. Zack, H. A. Quigley, S. D. Smith, M. E. Pease, Arch Ophthalmol 1997, 115, 1031.
L. Guo, S. E. Moss, R. A. Alexander, R. R. Ali, F. W. Fitzke, M. F. Cordeiro, Invest Ophthalmol Vis Sci 2005, 46, 175.
I. Spector, N. R. Shochet, Y. Kashman, A. Groweiss, Science 1983, 219, 493.
M. Coué, S. L. Brenner, I. Spector, E. D. Korn, FEBS Letters 1987, 213, 316.
E. G. Yarmola, T. Somasundaram, T. A. Boring, I. Spector, M. R. Bubb, J Biol Chem 2000, 275, 28120.
Karlin S, Altschul SF. Methods for assessing the statistical significance of molecular sequence features by using general scoring schemes. Proc Natl Acad Sci U S A. Mar. 1990;87(6):2264-8. doi: 10.1073/pnas.87.6.2264. PMID: 2315319; PMCID: PMC53667.
Altschul SF, Madden TL, Schaffer AA, Zhang J, Zhang Z, Miller W, Lipman DJ. Gapped BLAST and PSI-BLAST: a new generation of protein database search programs. Nucleic Acids Res. Sep. 1, 1997;25(17):3389-402. doi: 10.1093/nar/25.17.3389. PMID: 9254694; PMCID: PMC146917.
Burke, J. A.; Zhang, X.; Bobbala, S.; Frey, M. A.; Bohorquez Fuentes, C.; Freire Haddad, H.; Allen, S. D.; Richardson, R. A. K.; Ameer, G. A.; Scott, E. A. Subcutaneous Nanotherapy Repurposes the Immunosuppressive Mechanism of Rapamycin to Enhance Allogeneic Islet Graft Viability. Nat. Nanotechnol. 2022, 17 (3), 319-330. https://doi.org/10.1038/s41565-021-01048-2.
Nichols et al. Factors affecting size and swelling of poly(ethylene glycol) microspheres formed in aqueous sodium sulfate solutions without surfactants, Biomaterials 30(29) (2009) 5283-91.
Scott et al. Modular scaffolds assembled around living cells using poly(ethylene glycol) microspheres with macroporation via a non-cytotoxic porogen, Acta Biomater 6(1) (2010) 29-38.
Vasdekis et al. Vesicle Photonics, Annu. Rev. Mater. Res. 43 (2013) 283-305.
Allen SD et al. On the advancement of polymeric bicontinuous nanospheres toward biomedical applications. Nanoscale Horizons. 2019, 18 pages.
Modak M, Bobbala S, Lescott C, Liu YG, Nandwana V, Dravid VP, Scott EA. Magnetic Nanostructure-Loaded Bicontinuous Nanospheres Support Multicargo Intracellular Delivery and Oxidation-Responsive Morphological Transitions. ACS Appl Mater Interfaces. 2020; 12(50):55584-95. Epub Dec. 2, 2020. doi: 10.1021/acsami.0c15920. PubMed PMID: 33259182.
Vincent, M. P., Navidzadeh, J. O., Bobbala, S. & Scott, E. A. Leveraging self-assembled nanobiomaterials for improved cancer immunotherapy. Cancer Cell 40, 255-276 (2022).
Du F, et al. Immunotheranostic Polymersomes Modularly Assembled from Tetrablock and Diblock Copolymers with Oxidation-Responsive Fluorescence. Cell Mol Bioeng. 2017;10(5):357-70.
Shang, S, et al. "Induction of mycobacterium tuberculosis lipid-specific T cell responses by pulmonary delivery of mycolic acid-loaded polymeric micellar Nanocarriers." Frontiers in immunology 9 (2018): 2709.
Frey M, et al. Influences of nanocarrier morphology on therapeutic immunomodulation. Nanomedicine, 2018, 13(14): 1795-1811.
Scott EA, et al. Mass spectrometric mapping of fibrinogen conformations at poly(ethylene terephthalate) interfaces. Biomaterials. 2007;28(27):3904-17. Epub Jun. 22, 2007.
Scott EA. Immune Theranostics. Presentation at 2018 US Frontiers of Engineering Symposium. Sep. 7, 2018. 24 pages.
Frey M, et al. Mapping the supramolecular assembly space of poly(sarcosine)-b-poly(propylene sulfide) using a combinatorial copolymer library. Chem Commun (Camb). 2020;56(49):6644-7.
Karabin NB, et al. The Combination of Morphology and Surface Chemistry Defines the Biological Identity of Nanocarriers in Human Blood. bioRxiv. 2020.
Nagaraj R, et al. High Density Display of an Anti-Angiogenic Peptide on Micelle Surfaces Enhances Their Inhibition of αvß3 Integrin-Mediated Neovascularization In Vitro. Nanomaterials (Basel). 2020;10(3).
Stack T, Liu Y, Frey M, Bobbala S, Vincent M, Scott E. Enhancing subcutaneous injection and target tissue accumulation of nanoparticles via co-administration with macropinocytosis inhibitory nanoparticles (MiNP). Nanoscale Horiz. Jun. 2021. 393-400.
Soni D, et al. The Sixth Revolution in Pediatric Vaccinology: Immunoengineering and Delivery Systems. Pediatric Research. (2020): 1-9.
Stack T, et al. Co-administration of macropinocytosis inhibitory nanoparticles (MiNP) for enhanced nanoparticle circulation time

(56) References Cited

OTHER PUBLICATIONS and target tissue accumulation following subcutaneous injection. bioRxiv. 2020:2020.08.26.267054.
Scott EA. Immune Theranostics. The Bridge. vol. 48 Issue 4. p. 34-39. Dec. 14, 2018.
Zhang, Jingjing, et al. "Human CIK Cells Loaded with Gold Nanoprisms as Theranostic Platform for Targeted Photoacoustic Imaging and Enhanced Immuno-Photothermal Combined Therapy." Nano Biomedicine & Engineering 8.3 (2016).
Johnson, Mark. "What controls aqueous humour outflow resistance?. " Experimental eye research 82.4 (2006): 545-557.
Johnson, Mark, et al. "The pore density in the inner wall endothelium of Schlemm's canal of glaucomatous eyes." Investigative ophthalmology & visual science 43.9 (2002): 2950-2955.
Johnson, Mark, et al. "Modulation of outflow resistance by the pores of the inner wall endothelium." Investigative ophthalmology & visual science 33.5 (1992): 1670-1675.
Kizhatil, Krishnakumar, et al. "Schlemm's canal is a unique vessel with a combination of blood vascular and lymphatic phenotypes that forms by a novel developmental process." PLoS biology 12.7 (2014): e1001912.
Kahook, Malik Y., et al. "Long-term safety and ocular hypotensive efficacy evaluation of netarsudil ophthalmic solution: rho kinase elevated IOP treatment trial (ROCKET-2)." American journal of ophthalmology 200 (2019): 130-137.
Karmel, M. "Glaucoma pipeline drugs: targeting the trabecular meshwork." American Academy of Ophthalmology (2013).
Kashman, Y., A. Groweiss, and U. Shmueli. "Latrunculin, a new 2-thiazolidinone macrolide from the marine sponge Latrunculia magnifica." Tetrahedron Letters 21.37 (1980): 3629-3632.
Kaufman, Paul L., Anders Bill, and Ernst H. Bárány. "Effect of cytochalasin B on conventional drainage of aqueous humor in the cynomolgus monkey." Experimental Eye Research 25 (1977): 411-414.
Kopczynski, Casey C., and David L. Epstein. "Emerging trabecular outflow drugs." Journal of ocular pharmacology and therapeutics 30.2-3 (2014): 85-87.
Shi, Li-Feng, Yan Wu, and Cai-Yun Li. "Identification of high-affinity VEGFR3-binding peptides through a phage-displayed random peptide library." Journal of gynecologic oncology 26.4 (2015): 327-335.
Leber, Th. "Studien über den Flüssigkeitswechsel im Auge." Albrecht von Graefes Archiv für Ophthalmologie 19 (1873): 87-185.
Levy, Brian, et al. "Ocular hypotensive safety and systemic absorption of AR-13324 ophthalmic solution in normal volunteers." American journal of ophthalmology 159.5 (2015): 980-985.
Lewis, Richard A., et al. "Fixed-dose combination of AR-13324 and latanoprost: a double-masked, 28-day, randomised, controlled study in patients with open-angle glaucoma or ocular hypertension." British Journal of Ophthalmology (2015).
Vincent, Michael P., et al. "Surface chemistry-mediated modulation of adsorbed albumin folding state specifies nanocarrier clearance by distinct macrophage subsets." Nature communications 12.1 (2021): 648.
Mao, Lisa Kay, William C. Stewart, and M. Bruce Shields. "Correlation between intraocular pressure control and progressive glaucomatous damage in primary open-angle glaucoma." American journal of ophthalmology 111.1 (1991): 51-55.
Karabin, Nicholas B., et al. "Sustained micellar delivery via inducible transitions in nanostructure morphology." Nature communications 9.1 (2018): 624.
Napoli, Alessandro, et al. "Lyotropic behavior in water of amphiphilic ABA triblock copolymers based on poly (propylene sulfide) and poly (ethylene glycol)." Langmuir 18.22 (2002): 8324-8329.
Napoli, Alessandro, et al. "Oxidation-responsive polymeric vesicles." Nature materials 3.3 (2004): 183-189.
Nel, Andre E., et al. "Understanding biophysicochemical interactions at the nano—bio interface." Nature materials 8.7 (2009): 543-557.
Norbury, Christopher C. "Drinking a lot is good for dendritic cells." Immunology 117.4 (2006): 443-451.
Oh, Nuri, and Ji-Ho Park. "Endocytosis and exocytosis of nanoparticles in mammalian cells." International journal of nanomedicine 9.sup1 (2014): 51-63.
Okka, Mehmet, Baohe Tian, and Paul L. Kaufman. "Effects of latrunculin B on outflow facility, intraocular pressure, corneal thickness, and miotic and accommodative responses to pilocarpine in monkeys." Transactions of the American Ophthalmological Society 102 (2004): 251.
Park, Chan Young, et al. "High-throughput screening for modulators of cellular contractile force." Integrative Biology 7.10 (2015): 1318-1324.
Patel, Gaurang, et al. "Molecular taxonomy of human ocular outflow tissues defined by single-cell transcriptomics." Proceedings of the National Academy of Sciences 117.23 (2020): 12856-12867.
Perkumas, K. M., and W. D. Stamer. "Protein markers and differentiation in culture for Schlemm's canal endothelial cells." Experimental eye research 96.1 (2012): 82-87.
Peterson, Jennifer A., et al. "Effect of latrunculin-B on outflow facility in monkeys." Experimental eye research 70.3 (2000): 307-313.
Peterson, Jennifer A., et al. "Latrunculin-A increases outflow facility in the monkey." Investigative Ophthalmology and Visual Science 40 (1999): 931-941.
Peterson, Jennifer A., et al. "Latrunculins' effects on intraocular pressure, aqueous humor flow, and corneal endothelium." Investigative Ophthalmology & Visual Science 41.7 (2000): 1749-1758.
Petros, Robby A., and Joseph M. DeSimone. "Strategies in the design of nanoparticles for therapeutic applications." Nature reviews Drug discovery 9.8 (2010): 615-627.
Prausnitz, Mark R., and Jeremy S. Noonan. "Permeability of cornea, sclera, and conjunctiva: a literature analysis for drug delivery to the eye." Journal of pharmaceutical sciences 87.12 (1998): 1479-1488.
Quigley, Harry A., and Aimee T. Broman. "The number of people with glaucoma worldwide in 2010 and 2020." The British journal of ophthalmology 90.3 (2006): 262.
Quigley, Harry A., et al. "Retinal ganglion cell death in experimental glaucoma and after axotomy occurs by apoptosis." Investigative ophthalmology & visual science 36.5 (1995): 774-786.
Vargas-Pinto, R., et al. "The effect of the endothelial cell cortex on atomic force microscopy measurements." Biophysical journal 105.2 (2013): 300-309.
Rossman, Jeremy S., George P. Leser, and Robert A. Lamb. "Filamentous influenza virus enters cells via macropinocytosis." Journal of virology 86.20 (2012): 10950-10960.
Russell, Paul, and Mark Johnson. "Elastic modulus determination of normal and glaucomatous human trabecular meshwork." Investigative ophthalmology & visual science 53.1 (2012): 117-117.
Cerritelli, Simona, Diana Velluto, and Jeffrey A. Hubbell. "PEG-SS-PPS: reduction-sensitive disulfide block copolymer vesicles for intracellular drug delivery." Biomacromolecules 8.6 (2007): 1966-1972.
Allen, Sean D., et al. "Polymersomes scalably fabricated via flash nanoprecipitation are non-toxic in non-human primates and associate with leukocytes in the spleen and kidney following intravenous administration." Nano Research 11 (2018): 5689-5703.
Allen, Sean D., et al. "Celastrol-loaded PEG-b-PPS nanocarriers as an anti-inflammatory treatment for atherosclerosis." Biomaterials science 7.2 (2019): 657-668.
Yi, Sijia, et al. "An injectable hydrogel platform for sustained delivery of anti-inflammatory nanocarriers and induction of regulatory T cells in atherosclerosis." Frontiers in Bioengineering and Biotechnology 8 (2020): 542.
Yi, Sijia, et al. "Tailoring nanostructure morphology for enhanced targeting of dendritic cells in atherosclerosis." ACS nano 10.12 (2016): 11290-11303.
Yi, Sijia, et al. "Surface engineered polymersomes for enhanced modulation of dendritic cells during cardiovascular immunotherapy." Advanced functional materials 29.42 (2019): 1904399.
Schwalbe, G. "Untersuchungen über die Lymphbahnen des Auges und ihre Begrenzungen." Archiv für mikroskopische Anatomie 6.1 (1870): 261-362.

(56) References Cited

OTHER PUBLICATIONS

Scott, Evan A., et al. "Dendritic cell activation and T cell priming with adjuvant- and antigen-loaded oxidation-sensitive polymersomes." Biomaterials 33.26 (2012): 6211-6219.
Segura, Tatiana, and Jeffrey A. Hubbell. "Synthesis and in vitro characterization of an ABC triblock copolymer for siRNA delivery." Bioconjugate chemistry 18.3 (2007): 736-745.
Seidel, Erich. "Weitere experimentelle Untersuchungen über die Quelle und den Verlauf der intraokularen Saftströmung: IX. Mitteilung. Über den Abfluß des Kammerwassers aus der vorderen Augenkammer." Albrecht von Graefes Archiv für Ophthalmologie 104 (1921): 357-402.
Serle, Janet B., et al. "Two phase 3 clinical trials comparing the safety and efficacy of netarsudil to timolol in patients with elevated intraocular pressure: Rho kinase elevated IOP treatment trial 1 and 2 (ROCKET-1 and ROCKET-2)." American journal of ophthalmology 186 (2018): 116-127.
Sit, Arthur J., et al. "Factors affecting the pores of the inner wall endothelium of Schlemm's canal." Investigative Ophthalmology and Visual Science 38.8 (1997): 1517-1525.
Yi, S., S. Y. Kim, M. P. Vincent, S. A. Yuk, S. Bobbala, F. Du, and E. A. Scott. 2022. Dendritic peptide-conjugated polymeric nanovectors for non-toxic delivery of plasmid DNA and enhanced non-viral transfection of immune cells. iScience 25:104555. PMCPMC9234717.
Stack, Trevor, et al. "Modulation of Schlemm's canal endothelial cell stiffness via latrunculin loaded block copolymer micelles." Journal of Biomedical Materials Research Part A 106.7 (2018): 1771-1779.
Vasdekis, Andreas E., et al. "Precision intracellular delivery based on optofluidic polymersome rupture." ACS nano 6.9 (2012): 7850-7857.
Tanna, Angelo P., Hamed Esfandiari, and Kyla Teramoto. "Reversible corneal endothelial abnormalities with netarsudil." Journal of Glaucoma 29.6 (2020): e41-e43.
Tanna, Angelo P., and Mark Johnson. "Rho kinase inhibitors as a novel treatment for glaucoma and ocular hypertension." Ophthalmology 125.11 (2018): 1741-1756.
Piotrowski-Daspit, Alexandra S., et al. "Polymeric vehicles for nucleic acid delivery." Advanced drug delivery reviews 156 (2020): 119-132.
Stano, Armando, et al. "Tunable T cell immunity towards a protein antigen using polymersomes vs. solid-core nanoparticles." Biomaterials 34.17 (2013): 4339-4346.
Vahabikashi, Amir, et al. "Increased stiffness and flow resistance of the inner wall of Schlemm's canal in glaucomatous human eyes." Proceedings of the National Academy of Sciences 116.52 (2019): 26555-26563.
Agrahari, Vibhuti, et al. "A comprehensive insight on ocular pharmacokinetics." Drug delivery and translational research 6 (2016): 735-754.
Allen, Sean, Yu-Gang Liu, and Evan Scott. "Engineering nanomaterials to address cell-mediated inflammation in atherosclerosis." Regenerative engineering and translational medicine 2 (2016): 37-50.
Allen, Sean, et al. "Facile assembly and loading of theranostic polymersomes via multi-impingement flash nanoprecipitation." Journal of Controlled Release 262 (2017): 91-103.
Allen, Sean D., et al. "Benchmarking bicontinuous nanospheres against polymersomes for in vivo biodistribution and dual intracellular delivery of lipophilic and water-soluble payloads." ACS applied materials & interfaces 10.40 (2018): 33857-33866.
Allen, Sean, Michael Vincent, and Evan Scott. "Rapid, scalable assembly and loading of bioactive proteins and immunostimulants into diverse synthetic nanocarriers via flash nanoprecipitation." JoVE (Journal of Visualized Experiments) 138 (2018): e57793.
Allingham, R. Rand, et al. "The relationship between pore density and outflow facility in human eyes." Investigative ophthalmology & visual science 33.5 (1992): 1661-1669.
Andrés-Guerrero, Vanessa, Julián García-Feijoo, and Anastasios Georgios Konstas. "Targeting Schlemm's canal in the medical therapy of glaucoma: current and future considerations." Advances in therapy 34 (2017): 1049-1069.
Anselmo, Aaron C., et al. "Elasticity of nanoparticles influences their blood circulation, phagocytosis, endocytosis, and targeting." ACS nano 9.3 (2015): 3169-3177.
Araki, Nobukazu, Melissa T. Johnson, and Joel A. Swanson. "A role for phosphoinositide 3-kinase in the completion of macropinocytosis and phagocytosis by macrophages." The Journal of cell biology 135.5 (1996): 1249-1260.
Ascher, K. W. "Aqueous veins: preliminary note." American Journal of Ophthalmology 25.1 (1942): 31-38.
Aspelund, Aleksanteri, et al. "The Schlemm's canal is a VEGF-C/VEGFR-3-responsive lymphatic-like vessel." The Journal of clinical investigation 124.9 (2014): 3975-3986.
Asrani, Sanjay, et al. "Netarsudil/latanoprost fixed-dose combination for elevated intraocular pressure: three-month data from a randomized phase 3 trial." American journal of ophthalmology 207 (2019): 248-257.
Bacharach, Jason, et al. "Double-masked, randomized, dose-response study of AR-13324 versus latanoprost in patients with elevated intraocular pressure." Ophthalmology 122.2 (2015): 302-307.
Bill, Anders. "The albumin exchange in the rabbit eye." Acta Physiologica Scandinavica 60.1-2 (1964): 18-29.
Bill, Anders. "The aqueous humor drainage mechanism in the cynomolgus monkey (*Macaca irus*) with evidence for unconventional routes." Investigative ophthalmology & visual science 4.5 (1965): 911-919.
Bill, Anders. "The drainage of albumin from the uvea." Experimental Eye Research 3.2 (1964): 179-187.
Bill, Anders, and Krister Hellsing. "Production and drainage of aqueous humor in the cynomolgus monkey (*Macaca irus*)." Investigative Ophthalmology & Visual Science 4.5 (1965): 920-926.
Bobbala, Sharan, Sean David Allen, and Evan Alexander Scott. "Flash nanoprecipitation permits versatile assembly and loading of polymeric bicontinuous cubic nanospheres." Nanoscale 10.11 (2018): 5078-5088.
Bobbala, Sharan, et al. "Employing bicontinuous-to-micellar transitions in nanostructure morphology for on-demand photo-oxidation responsive cytosolic delivery and off-on cytotoxicity." Nanoscale 12.9 (2020): 5332-5340.
Bobbala, Sharan, Michael P. Vincent, and Evan A. Scott. "Just add water: hydratable, morphologically diverse nanocarrier powders for targeted delivery." Nanoscale 13.26 (2021): 11349-11359.
Boussommier-Calleja, Alexandra, et al. "Pharmacologic manipulation of conventional outflow facility in ex vivo mouse eyes." Investigative ophthalmology & visual science 53.9 (2012): 5838-5845.
Boussommier-Calleja, Alexandra, et al. "Physical factors affecting outflow facility measurements in mice." Investigative ophthalmology & visual science 56.13 (2015): 8331-8339.
Braakman, Sietse T., et al. "Biomechanical strain as a trigger for pore formation in Schlemm's canal endothelial cells." Experimental eye research 127 (2014): 224-235.
Rasmussen, Carol A., et al. "Latrunculin B reduces intraocular pressure in human ocular hypertension and primary open-angle glaucoma." Translational vision science & technology 3.5 (2014): 1-1.
Dautriche, Cula N., et al. "A closer look at Schlemm's canal cell physiology: implications for biomimetics." Journal of functional biomaterials 6.3 (2015): 963-985.
Cerritelli, Simona, et al. "Aggregation behavior of poly (ethylene glycol-bl-propylene sulfide) di- and triblock copolymers in aqueous solution." Langmuir 25.19 (2009): 11328-11335.
Chen, Tiffany J., and Nikesh Kotecha. "Cytobank: providing an analytics platform for community cytometry data analysis and collaboration." High-dimensional single cell analysis: Mass cytometry, multi-parametric flow cytometry and bioinformatic techniques (2014): 127-157.
Choquet, Hélène, Janey L. Wiggs, and Anthony P. Khawaja. "Clinical implications of recent advances in primary open-angle glaucoma genetics." Eye 34.1 (2020): 29-39.

(56) References Cited

OTHER PUBLICATIONS

Dowling, David J., et al. "Toll-like receptor 8 agonist nanoparticles mimic immunomodulating effects of the live BCG vaccine and enhance neonatal innate and adaptive immune responses." Journal of Allergy and Clinical Immunology 140.5 (2017): 1339-1350.
Overby, Darryl R., et al. "Altered mechanobiology of Schlemm's canal endothelial cells in glaucoma." Proceedings of the national Academy of Sciences 111.38 (2014): 13876-13881.
Dutta, Dipannita, and Julie G. Donaldson. "Search for inhibitors of endocytosis: Intended specificity and unintended consequences." Cellular logistics 2.4 (2012): 203-208.
Scott, Evan A., Nicholas B. Karabin, and Punn Augsornworawat. "Overcoming immune dysregulation with immunoengineered nanobiomaterials." Annual review of biomedical engineering 19 (2017): 57-84.
Elias, Drew R., et al. "Effect of ligand density, receptor density, and nanoparticle size on cell targeting." Nanomedicine: nanotechnology, biology and medicine 9.2 (2013): 194-201.
Ethier, C. Ross, et al. "Two pore types in the inner-wall endothelium of Schlemm's canal." Investigative ophthalmology & visual science 39.11 (1998): 2041-2048.
Sahay, Gaurav, Elena V. Batrakova, and Alexander V. Kabanov. "Different internalization pathways of polymeric micelles and unimers and their effects on vesicular transport." Bioconjugate chemistry 19.10 (2008): 2023-2029.
Gao, Huajian, Wendong Shi, and Lambert B. Freund. "Mechanics of receptor-mediated endocytosis." Proceedings of the National Academy of Sciences 102.27 (2005): 9469-9474.
Grant, W. Morton. "Clinical measurements of aqueous outflow." AMA archives of ophthalmology 46.2 (1951): 113-131.
Hämäläinen, Kaisa-Mari, et al. "Characterization of paracellular and aqueous penetration routes in cornea, conjunctiva, and sclera." Investigative ophthalmology & visual science 38.3 (1997): 627-634.
Herd, Heather, et al. "Nanoparticle geometry and surface orientation influence mode of cellular uptake." ACS nano 7.3 (2013): 1961-1973.
Huang, Yi, et al. "The effect of size, charge, and peptide ligand length on kidney targeting by small, organic nanoparticles." Bioengineering & Translational Medicine 5.3 (2020): e10173.
Spector, Ilan, et al. "Latrunculins—novel marine macrolides that disrupt microfilament organization and affect cell growth: I. Comparison with cytochalasin D." Cell motility and the cytoskeleton 13.3 (1989): 127-144.
Iversen, Tore-Geir, Tore Skotland, and Kirsten Sandvig. "Endocytosis and intracellular transport of nanoparticles: Present knowledge and need for future studies." Nano today 6.2 (2011): 176-185.
Yoo, Jihye, et al. "Active targeting strategies using biological ligands for nanoparticle drug delivery systems." Cancers 11.5 (2019): 640.

* cited by examiner

A

| Nanoparticle | Description |
|---|---|
| tBL-MC | targeted blank micelles (MCs) |
| BL-MC | blank MC (non-targeted) |
| tLatA MC | targeted MC carrying LatA |
| ntLatA MC | non-targeted MC carrying LatA |

b

SEQUENCE LISTING

```
Sequence total quantity: 1
SEQ ID NO: 1            moltype = AA  length = 12
FEATURE                 Location/Qualifiers
source                  1..12
                        mol_type = protein
                        organism = synthetic construct
SEQUENCE: 1
WHWLPNLRHY AS                                                      12
```

NANOPARTICLES FOR DELIVERY OF THERAPEUTICS TO THE EYE FOR TREATMENT OF GLAUCOMA

CROSS-REFERENCE TO RELATED APPLICATIONS

This application is the national stage entry of PCT/US2022/073598, filed on Jul. 11, 2022, which claims the benefit of and priority to U.S. Provisional Application No. 63/203,128 filed on Jul. 9, 2021. The contents of each are incorporated herein by reference in their entireties.

STATEMENT REGARDING FEDERALLY SPONSORED RESEARCH

This invention was made with government support under grant numbers EY019696 and HL132390 awarded by the National Institutes of Health.

SEQUENCE LISTING

The contents of the electronic sequence listing (title: 702581.02185.xml; size: 1,744 bytes; date of creation: Jul. 8, 2022) is hereby incorporated by reference in its entirety.

BACKGROUND OF THE INVENTION

Glaucoma is the leading cause of irreversible blindness, lacks a cure, and is currently estimated to affect 76 million people worldwide[1]. The prevalence of glaucoma continues to rise, with the number of individuals living with the disease projected to increase to ~112 million people by 2040[1]. The hallmark of glaucoma is elevated intraocular pressure (≥21 mm Hg)[2], which progressively damages retinal ganglion cells[3]. Multiple lines of evidence demonstrate mechanical dysfunction in pressure-regulating tissues contribute to this increase in intraocular pressure[4-13]. In the eye, intraocular pressure is determined by the balance between the rate of aqueous humor production by the ciliary body, and the rate of aqueous humor outflow through tissues of the conventional[14-17] and uveoscleral[18-21] outflow pathways. Ocular hypertension results from increased resistance to aqueous humor outflow through the conventional outflow pathway[22] that is positioned at the iridocorneal angle of the anterior segment and consists of the trabecular meshwork, Schlemm's canal, collector channels, intrascleral venous plexus and the aqueous veins. Decreased porosity[4-8] of the Schlemm's canal endothelium contributes to the increase in outflow resistance in glaucoma, and these porosity changes arise from an increase in Schlemm's canal stiffness that impairs pore formation[12]. Most recently, it was demonstrated that the source of outflow resistance is localized to a region within 1 μm of the inner wall of the Schlemm's canal endothelial surface[13].

Currently, first and second line glaucoma therapeutics decrease intraocular pressure by either (i) decreasing aqueous humor inflow, or (ii) driving a greater proportion of the aqueous humor outflow through the unconventional outflow pathway[23]. However, these treatments do not address the source of the increased outflow resistance that contributes to ocular hypertension[23]. Cell softening agents, such as actin depolymerizers and rho kinase inhibitors, improve aqueous humor outflow[24-26] by directly addressing dysfunction in the conventional outflow pathway. Cell softening agents are approved for clinical use in the US (Netarsudil[27-32]) and abroad (Ripasudil[33]), but suffer from side effects, including conjunctival hyperemia, conjunctival hemorrhage, cornea verticillata, eye pruritus, reduced visual acuity, and blurred vision[23]. Targeted drug delivery vehicles may address these issues by directing cell softening agents to their site of action while minimizing adverse events arising from off-target effects.

Thus, there is a remaining need in the art for a system that can be used to selectively deliver cell softening agents to Schlemm's canal endothelial cells to treat glaucoma.

SUMMARY OF THE INVENTION

In a first aspect, the present invention provides systems for targeted delivery of a therapeutic agent to a cell, particularly a Schlemm's canal (SC) endothelial cell. The systems comprise: (a) a nanocarrier comprising a poly(ethylene glycol)-block-poly(propylene sulfide) (PEG-b-PPS) copolymer, (b) the therapeutic agent loaded in the nanocarrier; and (c) a targeting moiety that targets SC endothelial cells incorporated into the surface of the nanocarrier. The targeting moiety comprises: (i) a peptide that specifically binds to SC endothelial cells; (ii) a polyethylene glycol (PEG) spacer; and (iii) a hydrophobic anchor.

In a second aspect, the present invention provides pharmaceutical compositions comprising a system described herein and one or more pharmaceutically acceptable carriers.

In a third aspect, the present invention provides methods of reducing the intraocular pressure in a subject in need thereof. The methods comprise administering to the subject a therapeutically effective amount of a pharmaceutical composition comprising a system described herein.

In a fourth aspect, the present invention provides methods of treating glaucoma in a subject in need thereof. The methods comprise administering to the subject a therapeutically effective amount of a pharmaceutical composition comprising a system described herein.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Figure 1:
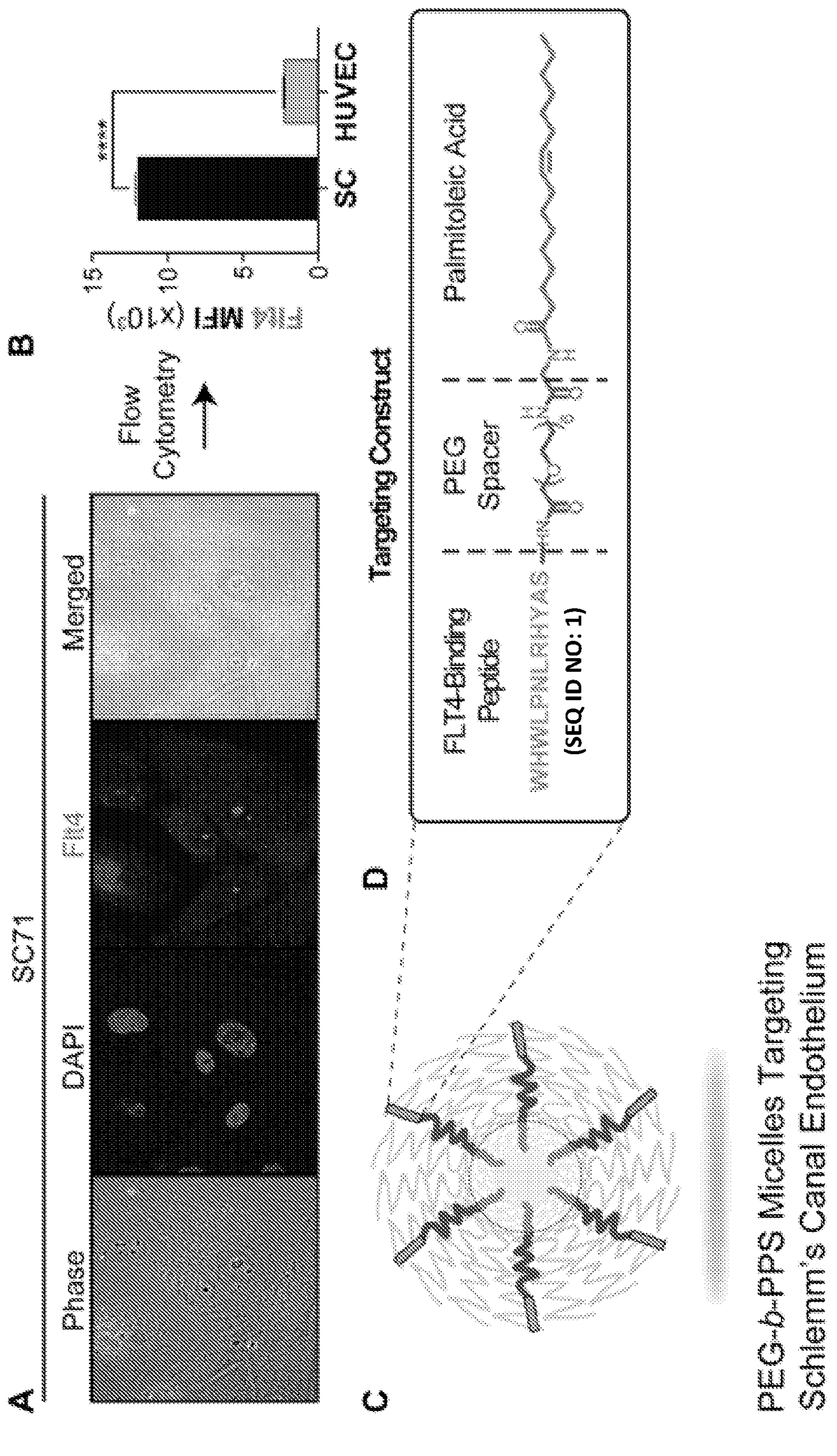
FIG. 1 shows the design of PEG-b-PPS micelles that target Schlemm's canal (SC) cells in the anterior segment of the eye. (A, B) Human SC cells express FLT4/VEGFR3. (A) Representative confocal microscopy images of SC endothelial cells that were stained with anti-FLT4 antibody to confirm presence of FLT4 on the cell surface. Cells were stained with Hoechst 33342 (blue) and anti-FLT4 antibody (red). (B) Flow cytometry data comparing median fluorescence intensity (MFI) of SC cells and HUVECs stained with anti-FLT4 antibodies. Data shown as mean±SEM. Significance determined by unpaired t-test (****$p<0.0001$). (C) Schematic representation of peptide-displaying micelles. (D) The peptide targeting construct consisting of targeting peptide, PEG spacer and palmitoleic acid tail. (E) LCMS spectra of the purified FLT4-targeting peptide construct. (F) Peptide loading efficiency of PEG6 peptide construct into PEG-b-PPS micelles at various molar ratios as determined by tryptophan fluorescence measurements. Data shown as mean±SD, N=3 technical replicates. (G) STEM micrograph of negatively stained PEG-b-PPS micelles (MC) displaying the peptide targeting construct (5%) (200,000× magnification). (H) Synchrotron small angle x-ray scattering (SAXS) plots for blank micelles, and micelles displaying the targeting peptide at 1% and 5% molar ratios. A core shell model (solid line) was fit to the data (gray points). The core radius (rc), shell thickness (rt), and total MC radius (r) is displayed together with the chi square ($X^2$) value for the final model fit.
Figure 1:
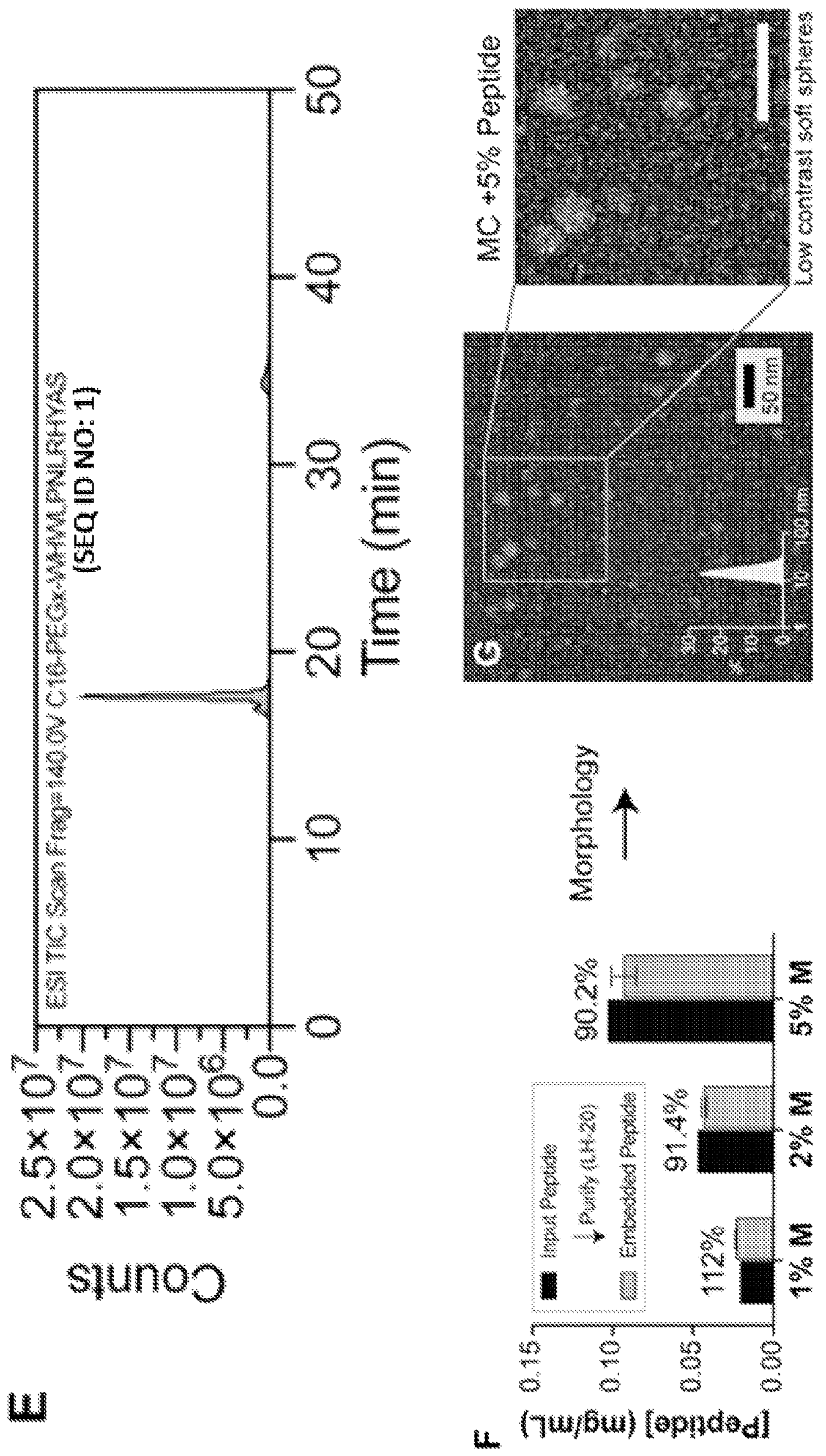
Figure 1:
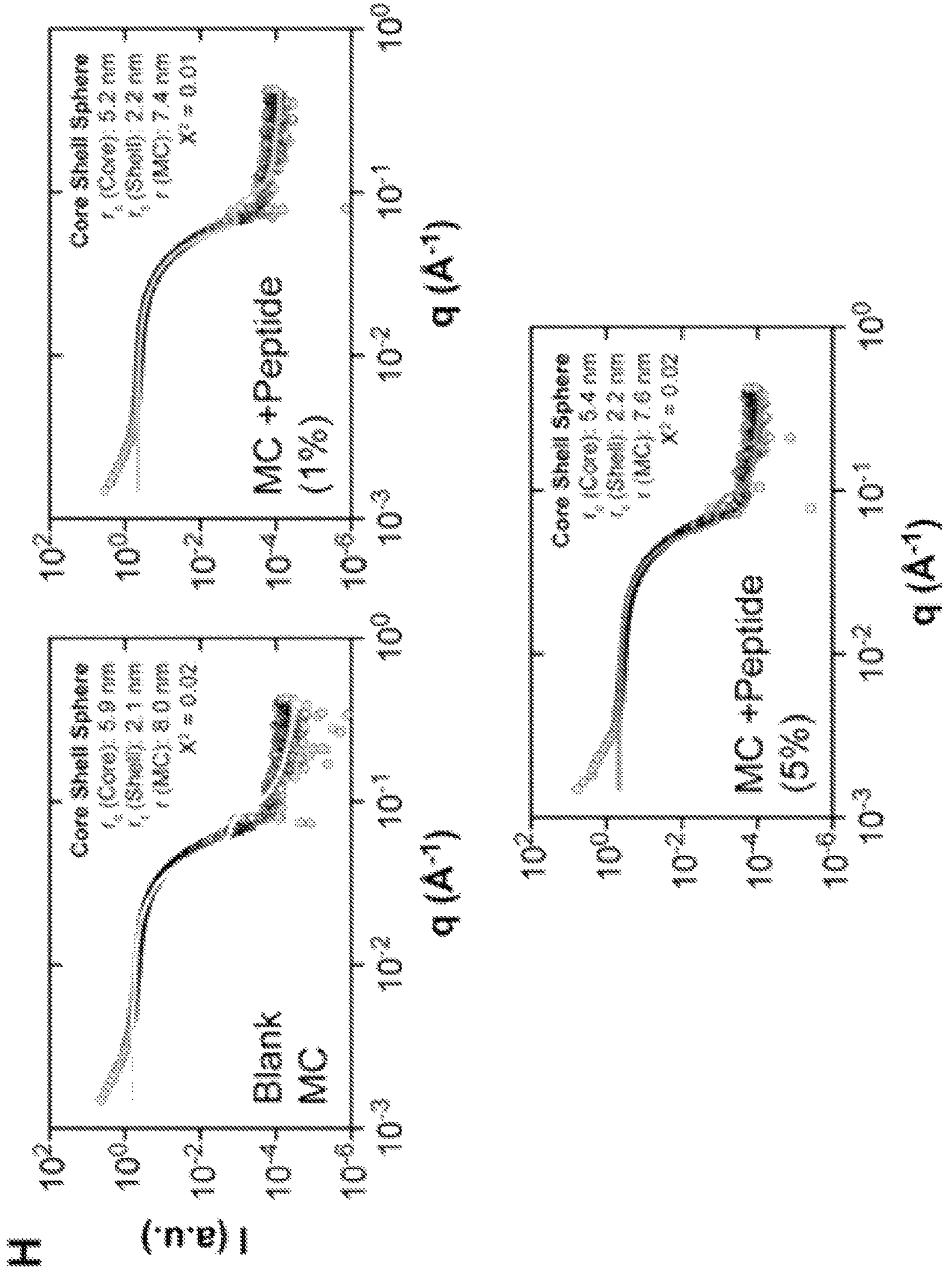

The present invention provides systems for targeted delivery of therapeutic agents to Schlemm's canal (SC) endothelial cells. Also provided are methods for using the systems to treat glaucoma or reduce intraocular pressure.

Primary open-angle glaucoma is associated with elevated intraocular pressure that damages the optic nerve and leads to gradual vision loss. One cause of this elevated intraocular pressure is increased stiffness of the SC endothelium in the aqueous humor outflow pathway. Several agents that relax this endothelium lower intraocular pressure in glaucoma patients and are approved for clinical use. However, these treatments have undesirable off-target effects and a lower than desired potency.

To address these issues, the present inventors developed a targeted self-assembled PEG-b-PPS micelle loaded with the cell softening agent latrunculin A (tLatA-MC). Their micelles are targeted to SC cells by a lipid-anchored targeting peptide that binds to the VEGFR3/FLT4 receptor, a lymphatic lineage marker that is highly expressed by SC cells relative to other ocular cells. In Example 1, the inventors demonstrate that increasing the targeting peptide surface density on the micelles increases their uptake by SC cells in vitro. They also demonstrate that tLatA-MC decrease SC cell stiffness in vitro and reduce intraocular pressure by 30-50% in a mouse model. In Example 2, the inventors confirm that VEGFR3/FLT4 receptors are a clinically relevant target that is present on SC cells from glaucoma patients and test several lipid-PEGx-peptide targeting constructs that differ in their number of PEG spacer units (x). They found that increasing the length of the PEG spacer in these constructs increased the accessibility of FLT4-binding peptides and enhanced nanocarrier uptake by SC cells. Further, they found that this enhanced targeting translates to intraocular pressure reductions in vivo that are sustained for a significantly longer time as compared to controls. Together, their results support the use of this cell-softening nanotherapy to selectively modulate the stiffness of SC cells for therapeutic reduction of intraocular pressure and treatment of glaucoma.

Systems:

The present invention provides targeted delivery systems that can be utilized to deliver therapeutic agents to target cells in the eye of a subject to treat glaucoma. Specifically, in a first aspect, the present invention provides systems for targeted delivery of a therapeutic agent to a SC endothelial cell. The systems comprise: (a) a nanocarrier comprising a poly(ethylene glycol)-block-poly(propylene sulfide) (PEG-b-PPS) copolymer, (b) one or more therapeutic agent loaded in the nanocarrier; and (c) a targeting moiety that targets SC endothelial cells incorporated into the surface of the nanocarrier. The targeting moiety comprises: (i) a peptide that specifically binds to SC endothelial cells; (ii) a polyethylene glycol (PEG) spacer; and (iii) a hydrophobic anchor.

A "nanocarrier" is nanomaterial that comprises a complex or vesicular nanoarchitecture and is used as a transport module for a cargo, such as a drug. A nanocarrier may encapsulate the cargo or the cargo may be incorporated into the nanocarrier itself. Commonly used nanocarriers include polymeric nanoparticles, liposomes, polymeric micelles, carbon nanotubes, dendrimers, solid lipid nanoparticles, magnetic nanoparticles, and quantum dots. The nanocarriers of the present invention are used to deliver cargo to specific cells within a subject.

In preferred embodiments, the nanocarrier is a micelle. As used herein, the term "micelle" refers a nanocarrier having a PEG weight fraction above 0.38. Suitably, the micelle has a PEG weight fraction of about 0.38 to about 0.69. Micelle nanocarriers have a spherical morphology and are typically smaller (e.g., less than 50 nm) than polymersomes. Micelles have a hydrophobic/lipophilic core and a hydrophilic exterior. The hydrophobic core can be loaded with lipophilic cargo (e.g., a therapeutic agent). Micelles can be prepared using known methods, for example, those described by Karabin et al. (*Nat Commun* 9, 624, 2018), which is incorporated herein by reference.

In some embodiments, the nanocarrier has a diameter within the range of 100 nm to 300 nm, 110 nm to 290 nm, 120 nm to 280 nm, 130 nm to 270 nm, 140 nm to 260 nm, 150 nm to 250 nm, 160 nm to 280 nm, 170 nm to 270 nm, 180 nm to 260 nm, 190 nm to 250 nm, 200 nm to 240 nm, 210 nm to 230 nm, or 215 nm to 225 nm. In other embodiments, the nanocarrier has a diameter within the range of 5 nm to 60 nm, 8 nm to 57 nm, 11 nm to 54 nm, 14 nm to 51 nm, 17 nm to 48 nm, 20 nm to 45 nm, 23 nm to 42 nm, 26 nm to 39 nm, 29 nm to 36 nm, or 32 nm to 33 nm. In other embodiments, the nanocarrier has a diameter within the range of 10 nm to 20 nm, 11 nm to 19 nm, 12 nm to 18 nm, 13 nm to 17 nm, or 14 nm to 16 nm.

The nanocarrier used with the present invention comprises a poly(ethylene glycol)-block-poly(propylene sulfide) (PEG-b-PPS) copolymer. PEG-b-PPS nanocarrier systems offer several advantages, including rapid gram-scale fabrication, high stability, high loading efficiency for proteins (e.g., ~70% for albumin) and small molecules (e.g., >90% for imiquimod derivatives), redox-sensitivity for intracellular delivery, and amenability to multimodal imaging. In the Examples the inventors utilized $PEG_{45}$-b-$PPS_{23}$. Thus, in some embodiments, the PEG-b-PPS copolymer is $PEG_{45}$-b-$PPS_{23}$. However, nearly any block lengths can be used. For example, in some embodiments, the PEG-b-PPS copolymer is $PEG_n$-b-$PPS_m$, wherein n can be any number ranging from 9 to 2300 and m can be any number ranging from 1 to 1000. Importantly, because polymer synthesis is inexact, there is a distribution of block lengths in any formulation. Thus, the numbers specified in these formulas merely represent the average block lengths.

PEG-b-PPS is an amphiphilic copolymer, i.e., a copolymer comprised of subunits or monomers that have different hydrophilic and hydrophobic characteristics. Typically, these subunits are present in groups of at least two and comprise blocks of a given character (e.g., a hydrophobic or hydrophilic block). Depending on the method of synthesis, these blocks may be comprised entirely of the same monomer or contain different monomer units dispersed throughout the block. These blocks can be arranged into a series of two blocks (diblock), three blocks (triblock), or more, forming the backbone of a block copolymer. Block units making up the copolymer can occur in regular intervals, or they can occur randomly. The ratio of hydrophobic to hydrophilic blocks in the copolymer is selected to achieve suitable aggregation for the desired architecture. PEG-b-PPS nanocarriers can be prepared via known methods. See, e.g., Du et al. (*Nat Commun* 29; 11(1):48962019, 2020), Du et al. (*J Control Release* 282:90-100, 2018), and Yi et al. (*ACS Nano* 10(12):11290-11303, 2016) each of which are incorporated herein by reference in their entirety.

The PEG-b-PPS copolymer used in the systems of the present invention may also include chemical modifications or end caps including, but not limited to, thiol, benzyl, pyridyl disulfide, phthalimide, vinyl sulfone, aldehyde, acrylate, maleimide, and n-hydroxysuccinimide groups. The chemical modifications may add a charged residue to the polymer or may be used to otherwise functionalize the polymer. Chemical moieties may also be covalently attached or grafted to the copolymer backbone. The grafted side chains may be added at regular intervals along the polymer backbone or randomly.

The nanocarriers of the present invention are "loaded" with a therapeutic agent, meaning that either (1) a therapeutic agent is incorporated into the nanocarrier itself, or (2), a therapeutic agent is encapsulated by the nanoparticle. In the Examples, the inventors encapsulated a therapeutic agent via cosolvent evaporation, as described by Stack et al. (*J Biomed Mater Res A* 106 (7), 1771-1779, 2018), which is hereby incorporated by reference in its entirety. Other common methods for loading a nanocarrier with a therapeutic agent include, without limitaiton, nanoprecipitation, flash nanoprecipitation, thin film hydration, and microfluidics.

As used herein, the term "therapeutic agent" refers to a molecule or drug that can be used to treat a disease or condition. In preferred embodiments, the therapeutic agent is an agent that can be used to treat glaucoma or high intraocular pressure. In some embodiments, the therapeutic agent is a cell softening agent. Suitable cell softening agents include, without limitation, actin depolymerizers (e.g., latrunculin A), Rho kinase inhibitors (e.g., Rhopressa, Glanatec), and nitric oxide donating compounds (e.g., Vyzulta). In other embodiments, the therapeutic agent is a gene therapy agent (e.g., a viral vector, a CRISPR reagent), anti-inflammatory agent (e.g., rapamycin, celastrol, vitamin D/calcitriol), anti-cancer agent (e.g., doxorubicin, camptothecin), or diagnostic agent (e.g., fluorescein, BODIPY, ethyl eosin, pheophorbide A). In the Examples, the inventors use their targeted delivery systems to deliver the drug latrunculin A to SC endothelial cells in the eyes of mice. Thus, in preferred embodiments, the therapeutic agent is latrunculin A. Latrunculin is a well-known transient actin depolymerizing agent that mechanically softens cells and has been shown to significantly reduce intraocular pressure in animal studies.

"Loading efficiency" is defined as the ratio of the amount of therapeutic agent in the assembled nanocarrier to the total amount of therapeutic agent applied during formulation of the nanocarrier. In some embodiments, the nanocarrier has a loading efficiency of the therapeutic agent of from 0.01% to 100%. In some embodiments, the nanocarrier has a loading efficiency of the therapeutic agent of from 0.1% to 98%, from 1% to 95%, from 5% to 90%, from 10% to 85%, from 15% to 80%, from 20% to 75%, from 25% to 70%, from 30% to 65%, from 35% to 60%, from 40% to 55%, or from 45% to 50%. In some embodiments, the loading efficiency is from 55% to 65%, from 56% to 64%, from 57% to 63%, from 58% to 62%, or from 59% to 61%.

Figure 2:
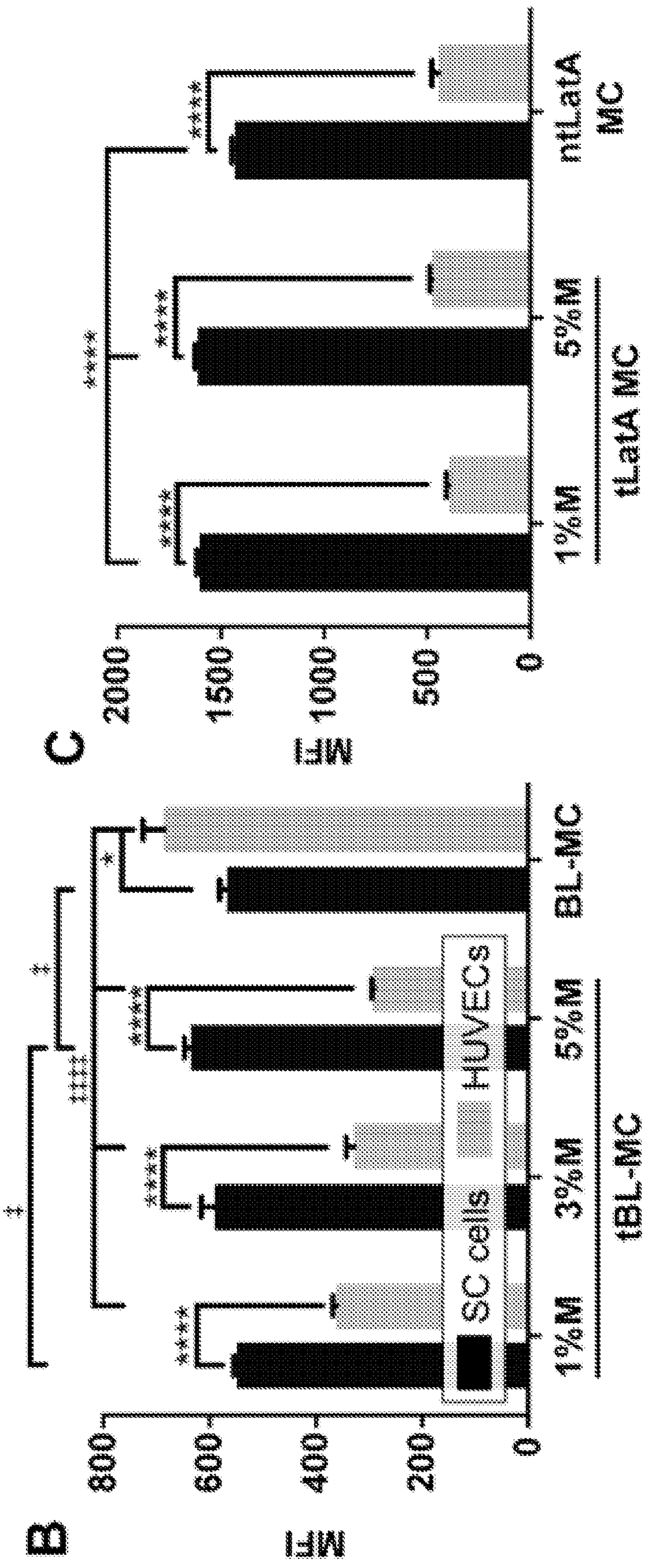
FIG. 2 demonstrates that the micellar display of a FLT4-binding peptide targets the delivery of latrunculin A to SC endothelial cells in vitro. (A-C) The FLT4-targeting peptide enhances micelle uptake by SC endothelial cells and decreases uptake by HUVEC. (A) Nanoparticle formulation abbreviations. (B) Unloaded micelles, (C) micelles loaded with latrunculin (LatA). Cells were incubated for 1 h with Alexa 555 labeled micelles incorporated with various molar ratios (1%, 3%, 5%) of peptide to micelle. After a 1-hour incubation, cells were washed, harvested, and fixed for analysis via flow cytometry. Median fluorescence intensity (MFI) was measured to quantify uptake of the various formulations by both cell types. Data shown as mean±SEM (n=3 biological replicates). In (B), significance was determined by one way ANOVA for each of the two cell types with post hoc Tukey's multiple comparisons test (‡‡‡‡ p<0.0001, ‡p<0.05). In (B-C), Two way ANOVA was used to evaluate differences between all groups with post hoc Sidak's multiple comparisons test (****p<0.0001, *p<0.05). (D-E) Targeted delivery of latrunculin A decreases the stiffness of human SC cells. (D) Representative images taken during AFM measurements of cells treated for 2 hours with BL-MC, tBL-MC (0.97 mg/mL), ntLatA-MC, or tLatA-MC (0.05 μM latrunculin A, 0.97 mg/mL); AFM tip is at top of each panel. (E) Stiffness of SC cells after 2 hours was determined by AFM; data shown is geometric mean±SD (≥5 measurements/condition). In (E), significance was determined by ANOVA with post hoc Tukey's multiple comparisons test (*p<0.05).
Figure 2:
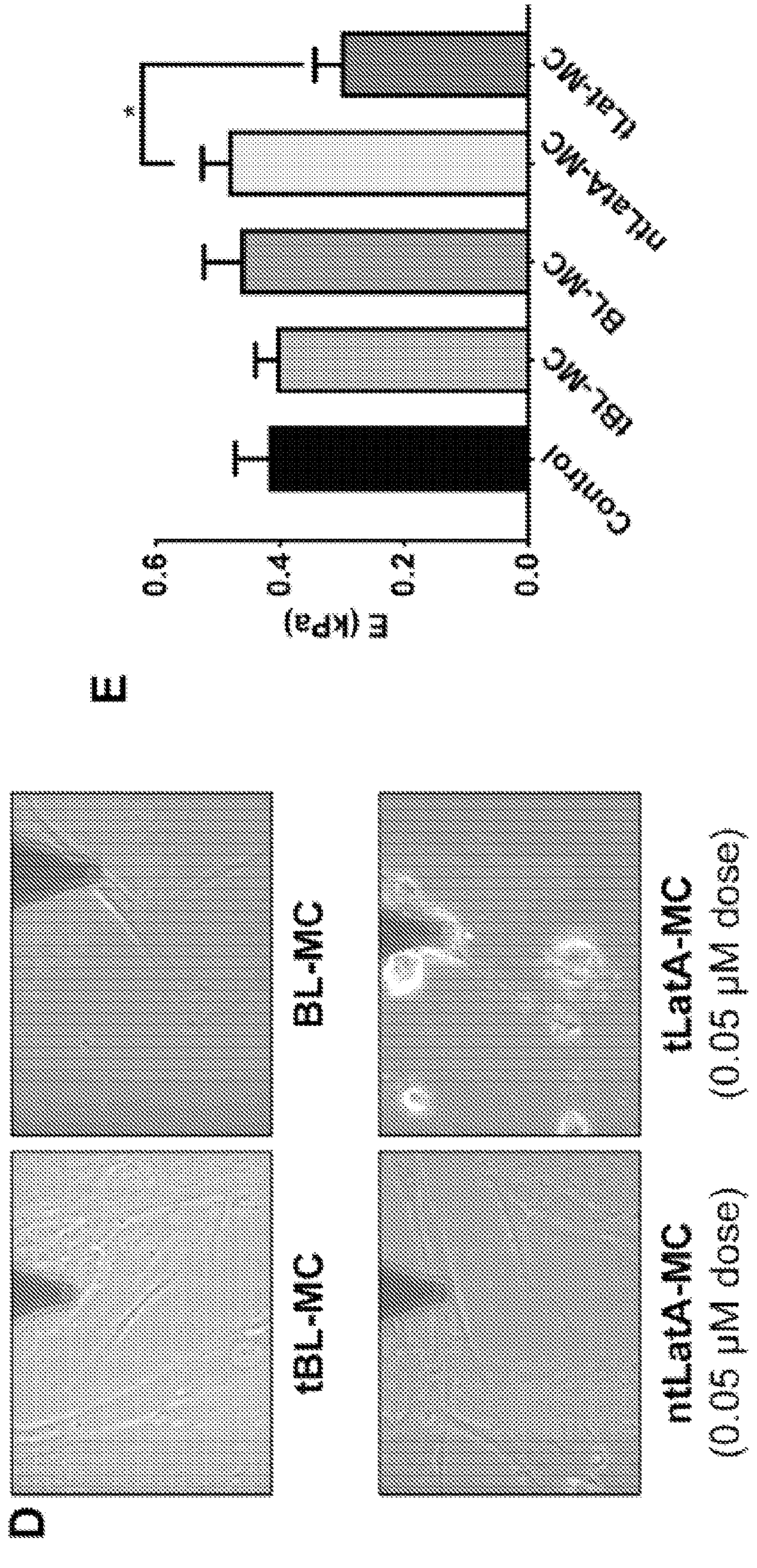

The systems of the present invention are used for targeted delivery of a therapeutic agent. As used herein, the term "targeted delivery" refers to the fact that the systems preferentially deliver the therapeutic agent to SC endothelial cells as compared to other ocular cells. The inventors have demonstrated that their nanocarriers are internalized by SC endothelial cells in significantly greater numbers than by human umbilical vein endothelial cells (see FIG. 2). Thus, "targeted delivery" can mean that the delivery to SC endothelial cells is statistically significantly greater than delivery to other cell types. In some embodiments, the delivery to endothelial cells is at least 2-fold greater, at least 5-fold great, at least 10-fold greater, at least 20-fold great, at least 30-fold greater, at least 40-fold greater, at least 50-fold greater, at least 60-fold greater, at least 70-fold greater, at least 80-fold greater, at least 90-fold greater, or at least 100-fold greater than the delivery to other cell types.

The systems of the present invention target therapeutic agents to SC endothelial cells. Schlemm's canal (SC) is a unique, complex vascular structure responsible for maintaining fluid homeostasis within the anterior segment of the eye by draining the flow of aqueous humor. In glaucoma, the normal outflow of aqueous humor into SC is progressively hindered, leading to a gradual increase in outflow resistance, which gradually results in elevated intraocular pressure. An increase in SC stiffness and decreased porosity of the SC endothelium contribute to this increase in outflow resistance. Thus, targeting cell softening agents to SC endothelial cells is a promising means to treat glaucoma.

In the systems of the present invention, targeted delivery to SC endothelial cells is achieved by including a targeting moiety on the surface of the nanocarrier. A "targeting moiety that targets SC endothelial cells" is any moiety that preferentially binds to SC endothelial cells as compared to other ocular cells. In the Examples, the inventors used a targeting moiety that comprises (i) a peptide that specifically binds to SC endothelial cells; (ii) a polyethylene glycol (PEG) spacer; and (iii) a hydrophobic anchor.

As used herein, the term "peptide" refers to short polymer of amino acids linked together by peptide bonds. Peptides are typically shorter than other amino acid polymers (e.g., proteins, polypeptides), and are typically about 50 amino acids or less in length. A peptide may comprise natural amino acids, non-natural amino acids, amino acid analogs, and/or modified amino acids. A peptide may comprise a portion of a naturally occurring protein or may be artificial.

The peptides used in the systems of the present invention specifically bind to SC endothelial cells, meaning that they bind to a moiety that is preferentially found on the surface of SC endothelial cells as compared to other ocular cells. In the Examples, the inventors utilized the targeting peptide of SEQ ID NO:1 (WHWLPNLRHYAS), which binds the FLT4/VEGFR3 receptor. The VEGFR3/FLT4 receptor is a lymphatic lineage marker that is highly expressed by SC endothelial cells relative to other ocular cells. Thus, in some embodiments, the peptide binds to a FLT4/VEGFR3 receptor. In specific embodiments, the peptide has a sequence of SEQ ID NO:1 or a sequence having 95% sequence similarity to SEQ ID NO:1. In some embodiments, the peptide has a sequence having 97% sequence similarity to SEQ ID NO:1. In some embodiments, the peptide has a sequence having 99% sequence similarity to SEQ ID NO:1. Other peptides that can bind to the FLT4/VEGFR3 receptor are also contemplated.

"Percentage of sequence similarity" is determined by comparing two optimally aligned sequences over a comparison window. The aligned sequences may comprise additions or deletions (i.e., gaps) relative to each other for optimal alignment. The percentage is calculated by determining the number of matched positions at which an identical nucleic acid base or amino acid residue occurs in both sequences, dividing the number of matched positions by the total number of positions in the window of comparison and multiplying the result by 100 to yield the percentage of sequence identity. Protein and nucleic acid sequence identities are evaluated using the Basic Local Alignment Search Tool ("BLAST"), which is well known in the art (*Proc. Natl. Acad. Sci. USA* (1990) 87: 2267-2268; *Nucl. Acids Res.* (1997) 25: 3389-3402). The BLAST programs identify homologous sequences by identifying similar segments, which are referred to herein as "high-scoring segment pairs", between a query amino acid or nucleic acid sequence and a test sequence which is preferably obtained from a protein or nucleic acid sequence database. Preferably, the statistical significance of a high-scoring segment pair is evaluated using the statistical significance formula *Proc. Natl. Acad. Sci. USA* (1990) 87: 2267-2268), the disclosure of which is incorporated by reference in its entirety. The BLAST programs can be used with the default parameters or with modified parameters provided by the user.

The "incorporation efficiency" of the targeting moiety is defined as the ratio of the amount of targeting moiety in the assembled nanocarrier to the total amount of targeting moiety applied during formulation of the nanocarriers. In some embodiments, the nanocarrier has an incorporation efficiency of the targeting moiety of greater than 90%. In some embodiments, the incorporation efficiency of the targeting moiety is greater than 95%, greater than 97%, greater than 98%, or greater than 99%.

A "molar ratio" is the ratio between the amounts (in moles) of any two substances involved in a chemical reaction. In some embodiments of the present invention, the molar ratio of the targeting moiety to the PEG-b-PPS copolymer is from 1% to 5%. In some embodiments, the molar ratio of the targeting moiety to the PEG-b-PPS copolymer is 1%. In some embodiments, the molar ratio of the targeting moiety to the PEG-b-PPS copolymer is 3%. In some embodiments, the molar ratio of the targeting moiety to the PEG-b-PPS copolymer is 5%.

Figure 11:
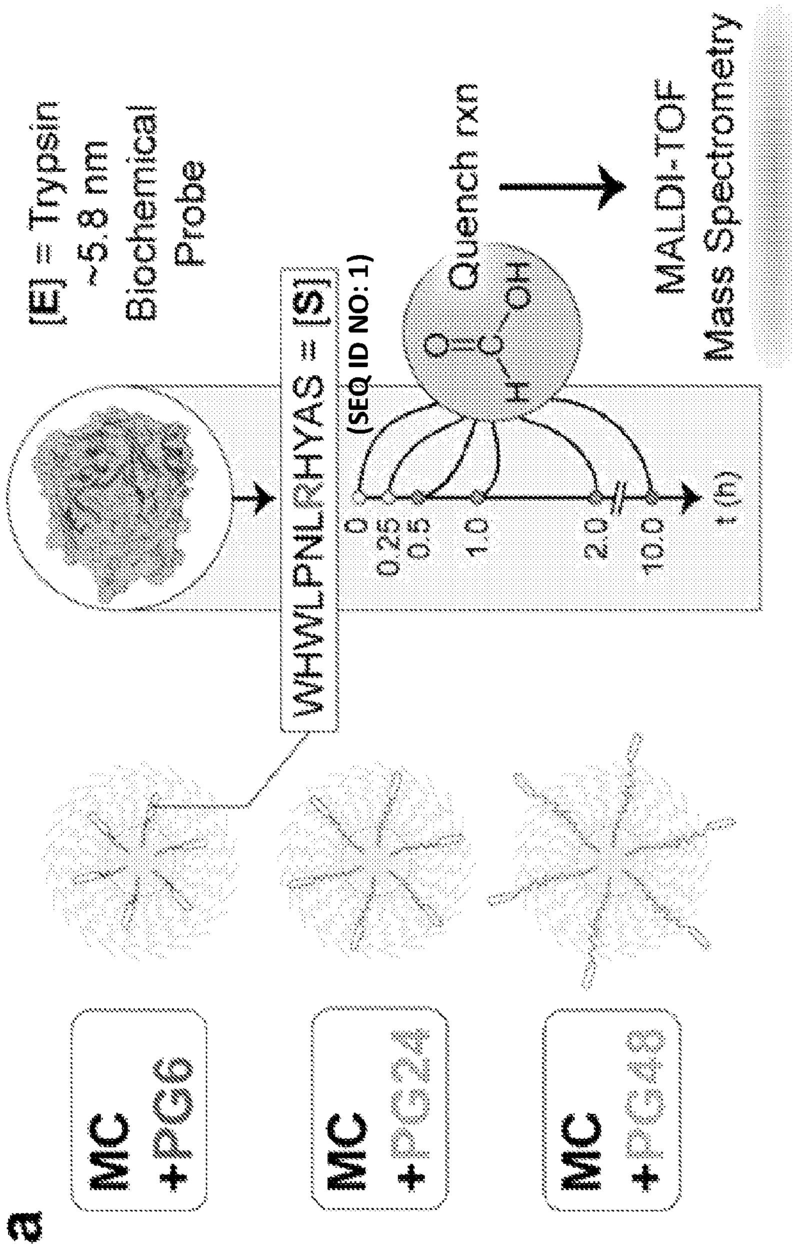
FIG. 11 demonstrates that differences in ligand biochemical accessibility modulate the rate of micelle uptake by SC endothelial cells and vascular endothelial cells in vitro. (a-b) Determination of biochemical access to lipid-anchored targeting peptides displayed on polymeric micelles. (a) Illustration of protease protection assay to evaluate peptide accessibility. (b) Trypsin proteolysis kinetics (n=5). Concentrations: [Peptide]=40 nM; [Trypsin]=800 nM. Pseudo first-order association model fits are displayed for comparison, $y=y_0+(y_{max}-y_0)*(1-e^{-kx})$, where k is the proteolysis rate ($hours^{-1}$). In all cases, $r^2>0.94$. (c-f) The surface-displayed PG48 FLT4-targeting peptide significantly increases micelle uptake by human SC cells and decreases uptake by HUVECs in vitro. (c) Illustration of PEG-b-PPS micelle formulations and the cellular uptake study. (d, e) Cellular uptake by normal SC cells (d) or HUVECs (e). MFI determined by flow cytometry. The mean±s.e.m. is displayed (n=3). (f) SC targeting specificity defined here as $SC_{MFI}/HUVEC_{MFI}$. For (d-f), statistical significance was determined by ANOVA with post hoc Tukey's multiple comparisons test and a 5% significance level. **p<0.0001, p<0.01, *p<0.05.
Figure 11:
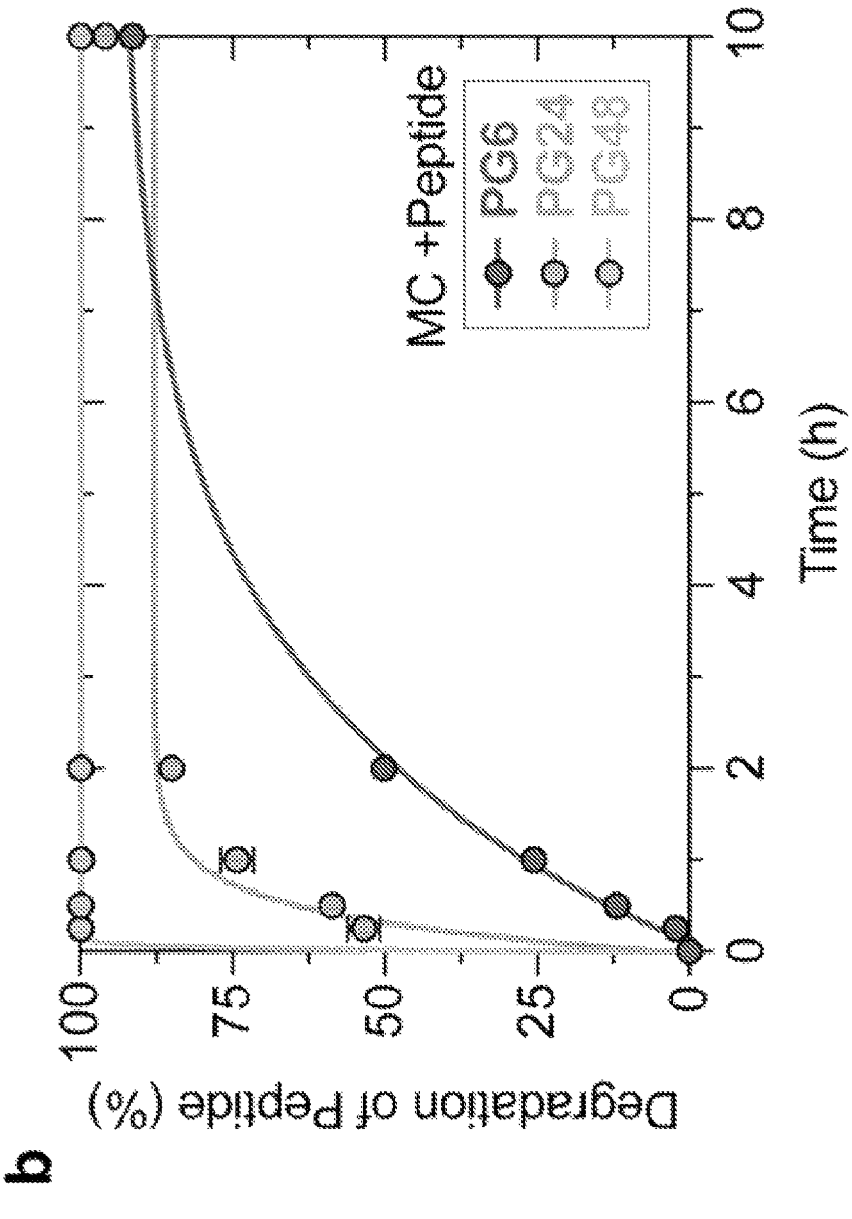
Figure 11:
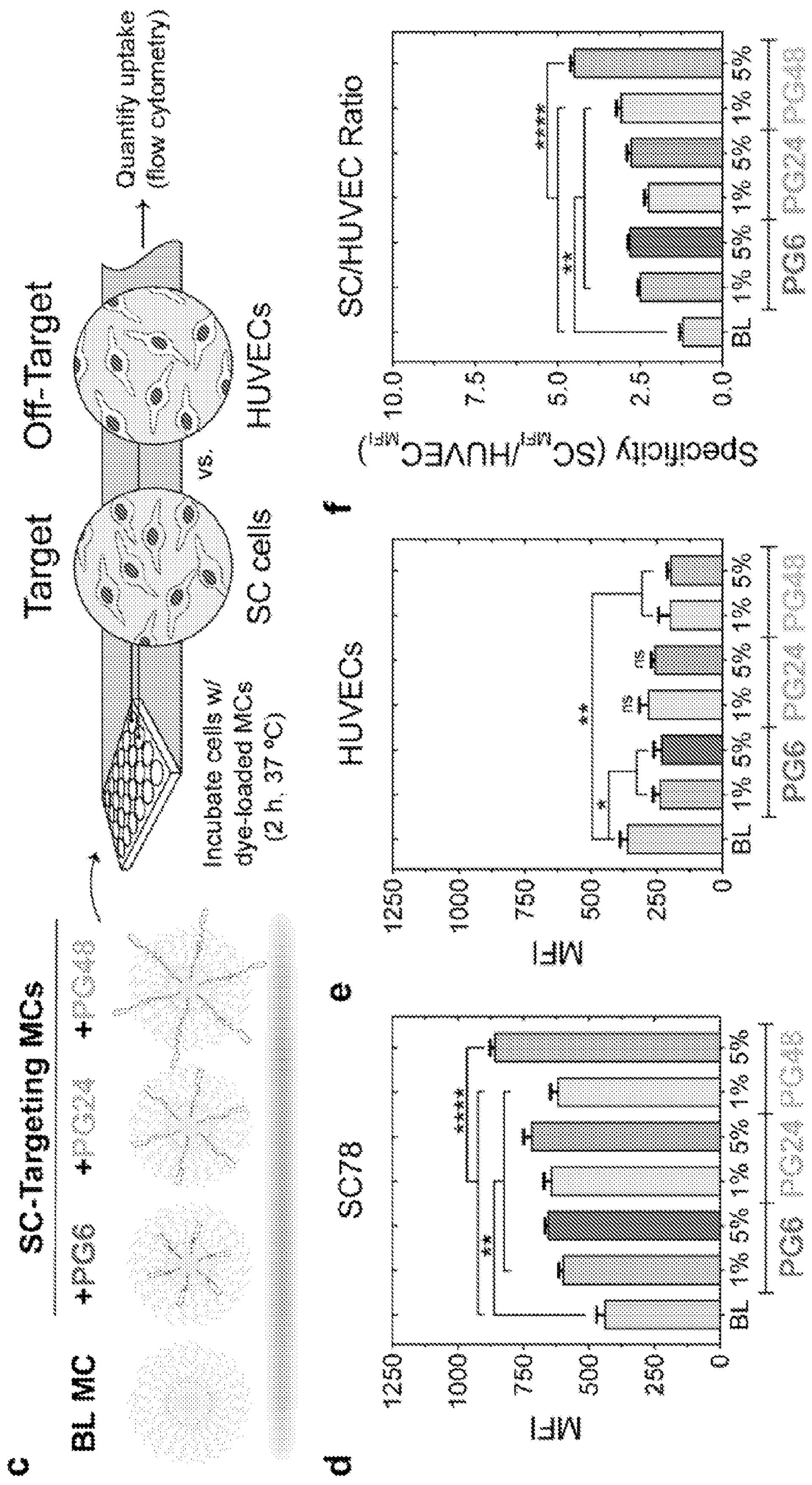

As used herein, a "polyethylene glycol (PEG) spacer" is a formulation of PEG that is used to link the peptide portion of the targeting moiety to the hydrophobic anchor. PEG is a polyether compound derived from petroleum. It is composed of repeating ethylene glycol units, i.e., —(O—$CH_2$—$CH_2$)—. In some embodiments, the PEG spacer has a formula "—HN—C(O)—$CH_2$—(O—$CH_2$—$CH_2$)$_n$—NH—C(O)—," wherein one end is attached to the peptide and the other end is attached to the hydrophobic anchor. In some embodiments, the PEG spacer has from 6 to 48 units (i.e., the "n" in the formula is an integer of 6-48). In Example 2, the inventors compared the ability of targeting moieties comprising PEG spacers with 6, 24, and 48 units to increase nanocarrier uptake by SC cells. They found that the PEG spacer with 48 units (i.e., PG48) provides increased targeting peptide accessibility as compared to the shorter PEG spacers and produces the greatest enhancement of nanocarrier uptake (see FIG. 11). Thus, in preferred embodiments, the PEG spacer has 48 units or more.

In the systems of the present invention, the targeting moiety is incorporated into the surface of the nanocarrier via a hydrophobic anchor. A "hydrophobic anchor" is a hydrophobic molecule that is attached to a moiety that one wishes to display on a membrane such that embedment of the hydrophobic molecule into the membrane anchors the moiety to the membrane. Suitable hydrophobic molecules for use as a hydrophobic anchor include, without limitation, lipids, cholesterol, hydrophobic polymers, and other lipophilic molecules that have a partition coefficient greater than 2. One example is a carboxylic acid hydrophobic anchor. In the Examples, the inventors included palmitoleic acid in their targeting moiety to facilitate insertion into the nanocarrier surface. Palmitoleic acid is an omega-7 monounsaturated fatty acid (16:1n-7) with the formula CH3(CH2)5CH═CH(CH2)7COOH. Thus, in some embodiments, the hydrophobic anchor is palmitoleic acid.

Pharmaceutical Compositions:

The systems disclosed herein may be incorporated into pharmaceutical compositions. Thus, in a second aspect, the present invention provides pharmaceutical compositions comprising a system described herein and one or more pharmaceutically acceptable carriers. The pharmaceutical compositions may be used in methods of treating glaucoma or reducing the intraocular pressure in a subject in need thereof.

The term "pharmaceutically acceptable carrier" refers to any carrier, diluent, or excipient that is compatible with the other ingredients of a composition and is not deleterious to the recipient. Pharmaceutically acceptable carriers are known in the art and include, but are not limited to, diluents (e.g., Tris-HCl, acetate, phosphate), preservatives (e.g., thimerosal, benzyl alcohol, parabens), solubilizing agents (e.g., glycerol, polyethylene glycerol), emulsifiers, liposomes, nanoparticles, and adjuvants. Pharmaceutically acceptable carriers may be aqueous or non-aqueous solutions, suspensions, or emulsions. Examples of nonaqueous solvents are propylene glycol, polyethylene glycol, vegetable oils (e.g., olive oil), and injectable organic esters (e.g., ethyl oleate). Aqueous carriers include isotonic solutions, alcoholic/aqueous solutions, emulsions, and suspensions, including saline and buffered media.

The pharmaceutical compositions of the present invention may further include additives such as albumin or gelatin to prevent absorption to surfaces, detergents (e.g., Tween 20, Tween 80, Pluronic F68, bile acid salts), antioxidants (e.g., ascorbic acid, sodium metabisulfite), bulking substances or tonicity modifiers (e.g., lactose, mannitol).

The pharmaceutical compositions may be formulated into dosage forms according to standard practices in the field of pharmaceutical preparations. See, e.g., Alphonso Gennaro, ed., *Remington's Pharmaceutical Sciences,* 18th Ed., (1990) Mack Publishing Co., Easton, Pa.

Methods of Treatment:

In a third aspect, the present invention provides methods of reducing the intraocular pressure in a subject in need thereof. The methods comprise administering to the subject a therapeutically effective amount of a pharmaceutical composition comprising a system described herein.

As used herein, the term "intraocular pressure" refers to the fluid pressure inside the eye. Intraocular pressure is typically determined by tonometry.

The present methods reduce intraocular pressure in a subject, meaning that the intraocular pressure in the eyes of the subject is lower after the method has been performed than it was before the method was performed. In some embodiments, the intraocular pressure is reduced by at least 35% after 24 hours from the administration. In some embodiments, the intraocular pressure is reduced by at least 40%, at least 45%, at least 50%, at least 55%, at least 60%, at least 65%, at least 70%, at least 75%, at least 80%, at least 85%, at least 90%, or at least 95% after 24 hours from the administration.

In a fourth aspect, the present invention provides methods of treating glaucoma in a subject in need thereof. The methods comprise administering to the subject a therapeutically effective amount of a pharmaceutical composition comprising a system described herein.

As used herein, the term "glaucoma" refers to a neurodegenerative disease characterized by damage to the optic nerve, usually due to excessively high intraocular pressure. Glaucoma is the leading cause of irreversible blindness.

As used herein, "treating" describes the management and care of a subject for the purpose of combating glaucoma. Treating includes the administration of a system or pharmaceutical composition described herein to prevent the onset of the symptoms or complications, to alleviate the symptoms or complications, to prevent the progression of symptoms or complications, or to eliminate the glaucoma. For example, treatment with the systems of the present invention may result in a stabilization of intraocular pressure, a reduction in intraocular pressure, or a reduction in one or more other symptom or condition associated with glaucoma (e.g., blurred vision, halos around lights, eye redness, eye pain, headaches, loss of vision, patchy blind spots in your side or central vision, tunnel vision, among others).

Accordingly, as used herein, the term "therapeutically effective amount" refers to an amount sufficient to achieve one or more of the outcomes listed above. For any active agent, a therapeutically effective amount can be estimated initially in cell culture assays or in as animal model. An appropriate amount of the system or pharmaceutical composition to be administered is dependent on a variety of factors, including the severity of the condition, the body weight and age of the subject, the frequency of administration, the duration of treatment, and the like. The disclosed compositions may be administered at any suitable dosage, frequency, and for any suitable duration necessary to achieve the desired therapeutic effect, i.e., to treat glaucoma or reduce intraocular pressure.

In the Examples, the inventors demonstrated that nanocarriers comprising the cell softening therapeutic agent latrunculin A can be used to reduce intraocular pressure in a mouse model of glaucoma. Thus, in some embodiments, the therapeutic agent is latrunculin A. In some embodiments, the concentration of latrunculin A in the pharmaceutical composition is 0.05 μM-20 μM. In some embodiments, the concentration of latrunculin A in the pharmaceutical composition is 0.1 μM-19 μM, 0.3 μM-18 μM, 0.5 μM-17 μM, 1 μM-15 μM, 2 μM-13 μM, 4 μM-11 μM, 6 μM-9 μM, or 7 μM-8 μM.

As used herein, the term "administering" refers to the introduction of a substance into a subject's body. Suitable modes of administration include, without limitation, ocular administration, topical administration, and extended release from a depot placed in the anterior chamber or in the vitreous chamber of the eye, among others.

The "subject" to which the methods are applied may be a mammal or a non-mammalian animal, such as a bird. Suitable mammals include, but are not limited to, humans, cows, horses, sheep, pigs, goats, rabbits, dogs, cats, bats, mice, and rats. In certain embodiments, the methods may be performed on lab animals (e.g., mice and rats) for research purposes. In other embodiments, the methods are used to treat commercially important farm animals (e.g., cows, horses, pigs, rabbits, goats, sheep, and chickens) or companion animals (e.g., cats and dogs). In a preferred embodiment, the subject is a human. In some embodiments, the subject is in need of reduction of intraocular pressure or is having one or more symptom of glaucoma.

The use herein of the terms "including," "comprising," or "having," and variations thereof, is meant to encompass the elements listed thereafter and equivalents thereof as well as additional elements. Embodiments recited as "including," "comprising" or "having" certain elements are also contemplated as "consisting essentially of" and "consisting of" those certain elements.

As used herein, "about" means within 5-10% of a stated concentration range or within 5-10% of a stated number.

It should be apparent to those skilled in the art that many additional modifications beside those already described are possible without departing from the inventive concepts. In interpreting this disclosure, all terms should be interpreted in the broadest possible manner consistent with the context. Variations of the term "comprising" should be interpreted as referring to elements, components, or steps in a non-exclusive manner, so the referenced elements, components, or steps may be combined with other elements, components, or steps that are not expressly referenced. Embodiments referenced as "comprising" certain elements are also contemplated as "consisting essentially of" and "consisting of" those elements. The term "consisting essentially of" and "consisting of" should be interpreted in line with the MPEP and relevant Federal Circuit's interpretation. The transitional phrase "consisting essentially of" limits the scope of a claim to the specified materials or steps "and those that do not materially affect the basic and novel characteristic(s)" of the claimed invention. "Consisting of" is a closed term that excludes any element, step or ingredient not specified in the claim. The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

The present invention has been described in terms of one or more preferred embodiments, and it should be appreciated that many equivalents, alternatives, variations, and modifications, aside from those expressly stated, are possible and within the scope of the invention.

The following Examples are offered for illustrative purposes only and are not intended to limit the scope of the present invention in any way. Indeed, various modifications of the invention in addition to those shown and described herein will become apparent to those skilled in the art from the foregoing description and the following examples and fall within the scope of the appended claims.

EXAMPLES

Example 1

In view of the adverse off-target effects of glaucoma drugs, we sought to develop and optimize a nanocarrier platform employing a targeting moiety for selective intracellular delivery to Schlemm's canal (SC) cells as a glaucoma treatment strategy. Nanomaterials have been shown to be advantageous drug delivery platforms that are well-suited for targeting specific cells and tissues[8,9]. Enhanced targeting and cell specificity allows for less off-target drug delivery and a lower potential for side effects[10]. Targeted nanomaterials have been shown to lower the therapeutic threshold concentration for certain drugs after encapsulation as well as reduce cytotoxicity and other unwanted effects in many cell types including SC cells[11-13].

Latrunculin is a well-known transient actin depolymerizing agent that mechanically softens cells[14] and has been shown to significantly reduce IOP in animal studies[5,15]. A phase I clinical trial, at concentrations previously found to be effective in primates, found a modest reduction of IOP with side effects that included mild redness, irritation, and a transient increase in central corneal thickness[16]. We speculated that targeted delivery of latrunculin to SC cells would provide increased bioavailability while minimizing side effects. Self-assembled poly (ethylene glycol)-b-poly(propylene sulfide) (PEG-b-PPS) block co-polymers have been used as versatile nanocarriers in a wide range of applications[12,17-23]. Depending on the morphology employed, PEG-b-PPS nanocarriers can retain both hydrophobic and hydrophilic payloads respectively in their cores or aqueous interior compartments[20,21,24-26] and are highly customizable through control of charge, size, and targeting moieties on their surfaces[8,27]. Nanomaterials provide a wide range of options for sustained drug and gene delivery[19,22,28], and the development of SC targeted nanocarriers will thus provide versatile options for the long term delivery of glaucoma therapeutics following a single intracameral injection.

In the following Example, we describe the design and development of a PEG-b-PPS controlled delivery system for delivery of latrunculin A to SC cells. SC cells express the lymphatic lineage receptor VEGFR3/FLT4 at moderately high levels as compared with blood vascular cells, which lack this receptor[29]. Thus, PEG-b-PPS micellar nanocarriers decorated with a FLT4-specific targeting peptide and loaded with latrunculin A were generated. The targeting and functional efficacy of this formulation was assessed in vitro in SC cells using uptake assays and atomic force microscopy (AFM). In vivo efficacy was evaluated using a C57BL/6J mouse model by measuring changes in IOP over multiple days after administering targeted nanocarriers intracamerally. Results show that the targeted nanocarriers were highly selective for SC cells in comparison with blood vascular cells, and that targeted latrunculin-loaded micelles (tLatA-MC) significantly lowered IOP in mouse eyes, as compared to control eyes treated with non-targeted latrunculin-loaded micelles (ntLatA-MC).

Results

Peptide lipid constructs can be attached to PEG-b-PPS micelles for intracellular delivery to SC endothelial cells with high efficiency and do not influence micelle structure. VEGFR3/FLT4 is a lymphatic marker that is expressed at the surface of SC endothelial cells[30,31]. We hypothesized that displaying a ligand for this receptor at the micelle surface would enhance micelle uptake selectively by SC cells as compared with other ocular cells, particularly blood vascular cells. We examined expression of FLT4 in human SC cells and human umbilical vein endothelial cells (HUVEC; used as a generic blood vascular cell control). Schlemm's cells were isolated as previously described[32] and HUVEC were obtained from Lonza (Basel, Switzerland). Cells were prepared as described in the methods and labeled with anti-FLT4 antibody. FLT4 expression was evaluated using laser scanning confocal microscopy, widefield fluorescence microscopy, and flow cytometry. As expected, FLT4 was present on the SC cell surface at significantly higher abundance than the HUVEC cell surface (FIG. 1A, B).

Targeted micelles were developed that incorporated an FLT4-targeting ligand (tBL-MC, and tLatA-MC; (BL=blank, t=peptide target) (FIG. 1C). Several peptide sequences binding FLT4 were previously identified using phage display[33]. The highest affinity peptide sequence, WHWLPNLRHYAS (SEQ ID NO: 1), was selected as a targeting moiety and attached to a palmitoleic acid tail via a PEG spacer (FIG. 1D). We have previously used constructs of this format with polymersomes for optimization of cell-selective targeting[8]. This targeting peptide construct was synthesized by solid phase peptide synthesis and was purified using preparatory HPLC. The resulting peptide construct had a mass of 2151 g/mol as assessed by LC-MS and was of high purity (≥95% pure; FIG. 1E). Micelles were formed via the co-solvent evaporation method and separate batches were pooled and then separated into blank MC (BL-MC), non-targeted LatA-MC (nt-LatA-MC), and targeted LatA-MC (tLatA-MC) formulations. tLatA-MC formulations were generated by incubating PEG-b-PPS micelles on an end-to-end shaker with 5% molar ratio of the peptide construct to PEG-b-PPS copolymer. Latrunculin A content of the micelles was quantified using HPLC as previously described[11], and loading efficiency was found to vary between 55% and 65% across multiple formulations. Peptide incorporation did not alter latrunculin A content of the micelles (Table 1).

Figure 5:
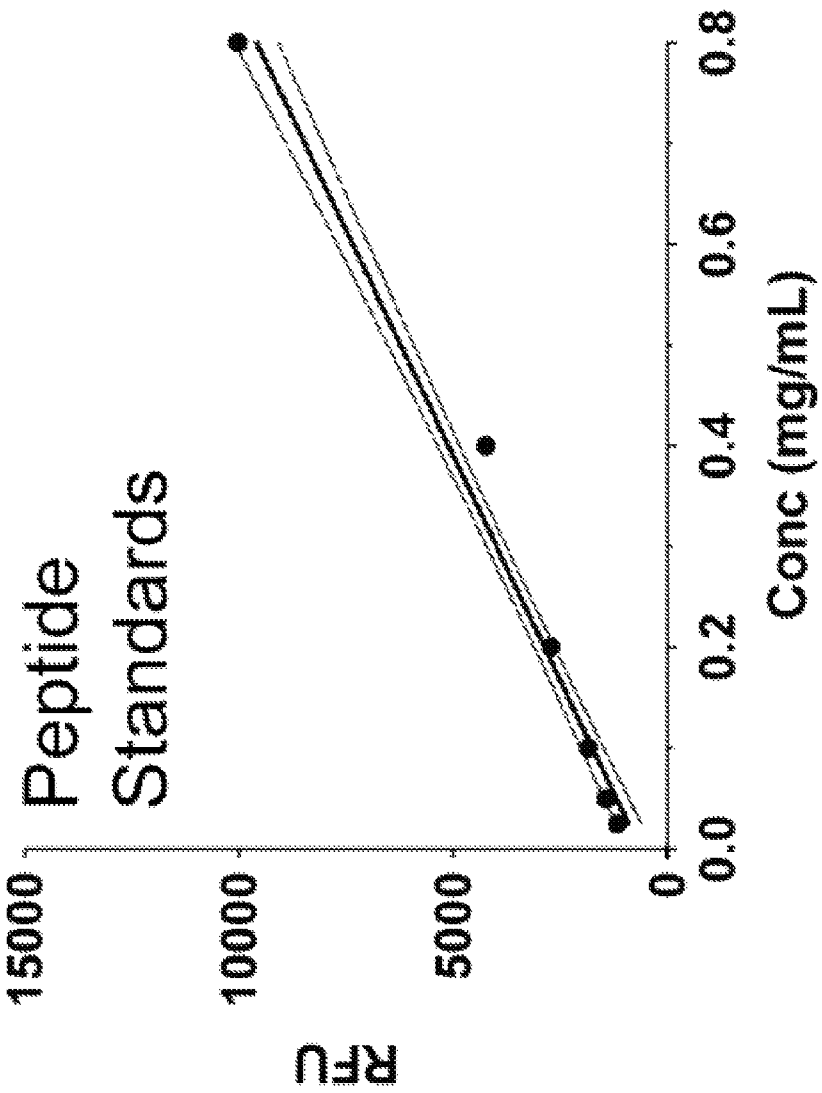
FIG. 5 shows the standard curve for the peptide fluorescence assay. Peptide-PEG-Lipid construct was dissolved in DMSO and serial dilutions were prepared in 1×PBS. Tryptophan fluorescence (Ex: 270 nm; Em: 350 nm) was measured using a SpectraMax M3 plate reader. $R^2$=0.98.

We next evaluated the tLatA-MC formulations for peptide incorporation using fluorescence spectroscopy. The tryptophan residues on the FLT4 targeting peptide grant the construct an intrinsic fluorescence that can be measured against a standard curve to determine peptide concentrations within the micelles (FIG. 5). Incorporation efficiencies of 91% or above were found for all measured molar ratios (FIG. 1F). Formulations were evaluated by transmission electron microscopy (TEM) and dynamic light scattering (DLS) to characterize size, polydispersity, and morphology (FIG. 1G). TEM characterization confirmed micelles prepared with peptide form successfully and are not disrupted by peptide embedding (FIG. 1G). There were not significant differences in micelle size between the groups (Table 1). We further characterized the micelle formulations with SAXS using synchrotron radiation (FIG. 1H). A core shell model was fit to each scattering profile, and the core shell radius and shell thickness of the micelles were estimated. Minimal differences in micelle dimensions were found between blank and peptide-displaying formulations (FIG. 1H). These results are consistent with our previous findings that neither latrunculin A loading nor incorporation of targeting peptide via lipid anchoring alter the size or structure of micelles[8], [11].

tLatA-MC demonstrated significantly greater uptake by SC cells and cell softening compared to non-targeted micelles in vitro. To evaluate the targeting efficacy of the FLT4 binding peptide, we examined the uptake of micelles. SC cells and HUVEC were incubated with 0.5 mg/mL Alexa 555 labeled micelles incorporated with various molar ratios (1%, 3%, 5%) of peptide to micelle for 1 hour at 37° C. Afterwards, cells were washed, harvested, and evaluated for particle uptake and cytotoxicity by flow cytometry. Flow cytometric analysis demonstrated that 5% peptide incorporation into targeted blank micelles (tBL-MC) modestly increased the number of particles internalized by SC cells as compared to ntBL-MC and 1% tBL-MC (FIG. 2A, B). Peptide incorporation significantly increased the number of particles internalized by SC cells as compared to HUVECs (FIG. 2B). This was primarily due to unexpectedly decreased micellar uptake by HUVEC as compared to blank MCs, which to our knowledge is a phenomenon not previously reported. This result may be related to altered cell membrane interactions caused by the palmitoleic acid in the targeted micelles[34].

When latrunculin A was loaded into micelles, the uptake by both cell types was altered. The decrease in uptake of targeted micelles (tBL-MC) by HUVECs, as compared with blank micelles (BL-MC), is no longer observed with latrunculin-loaded targeted micelles (tLatA-MC) (FIG. 2C). In SC cells, there was a statistically significant increase in all cases when peptide was incorporated as compared to blank micelles (FIG. 2C). SC cells demonstrated even greater uptake of the latrunculin A loaded constructs with and without peptide than the HUVEC. This difference increases considerably for the latrunculin A formulations, suggesting incorporation of latrunculin A alters the uptake pattern of micelles in both SC cells and HUVECs, perhaps by changing micellar properties that were not examined or through effects of latrunculin A on the cells. This phenomenon is of significant interest and is currently under additional investigation.

To evaluate the functional effects of tLatA-MC on cultured human SC cells, we used atomic force microscopy (AFM) to assess changes in cell stiffness and morphology (FIG. 2D, E) following treatment of SC cells with tLatA-MC (0.05 μM latrunculin A and 5% peptide by molar ratio) as compared with concentration-matched ntLatA-MC and micelle controls prepared without latrunculin A (BL-MC and tBL-MC) or a PBS vehicle control for 2 hours. latrunculin A-induced alterations in cell morphology, particularly the rounding of cell shape, indicative of cell softening[2,14], was observed by phase contrast microscopy (FIG. 2D). At this low concentration of latrunculin, only tLatA-MC significantly reduces SC cell stiffness (FIG. 2E). These data show that embedding the targeting peptide into the micelles increases the functional efficacy of the formulation in inducing cell softening of SC cells at low latrunculin concentrations as compared to ntLatA-MC.

tLatA-MC reduces IOP in C57B16 mice. We next evaluated the efficacy of our tLatA-MC formulation in vivo. Two different in vivo trials were performed (FIG. 3A); in the first, mice received intracameral injections of targeted latrunculin A-loaded tLatA-MC or blank micelle formulation, ntBL-MC. tLatA-MC significantly decreased IOP by 49% compared to blank MC at 24 hours (FIG. 3B).

Figure 3:
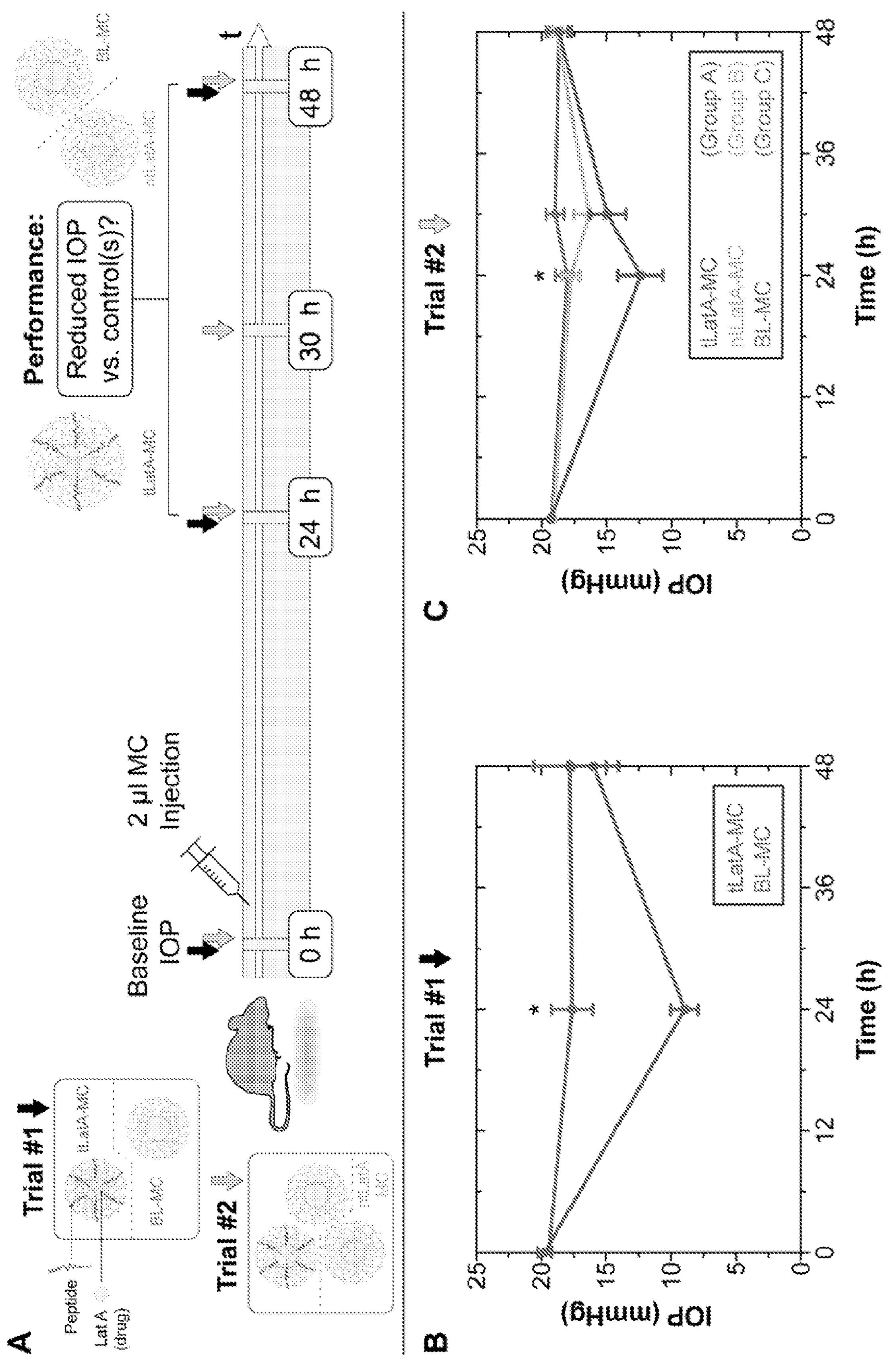
FIG. 3 demonstrates that targeted delivery of latrunculin reduces intraocular pressure (IOP) in mouse eyes. (A) Illustrative overview of experiments which consisted of two different IOP measurement schedules. Trial #1 and Trial #2 IOP timepoints are shown with black and grey arrows, respectively. (B) Trial 1 results. 2 μL of BL-MC or tLatA MC (40 mg/mL, 5% Peptide, 17 μM latrunculin A) were injected intracamerally into 5 mice. IOP was measured prior to injection, and after 24 h and 48 h. (C) Trial 2 results. 2 μL of BL-MC, ntLatA-MC, or tLatA-MC (15.5 μM latrunculin A, 40 mg/mL 5% peptide) micelles were injected into 1 eye of 5 mice each. IOP was measured prior to injection and at three timepoints during a 48-hour time course. IOP is measured by rebound tonometry (TonoLab; Icare). Data shown are mean±SEM (n=5). Trial #1 significance determined by unpaired t-test (*p<0.003). Trial #2 significance determined by ANOVA with post hoc Tukey's multiple comparisons test (*p<0.03).
Figure 6:
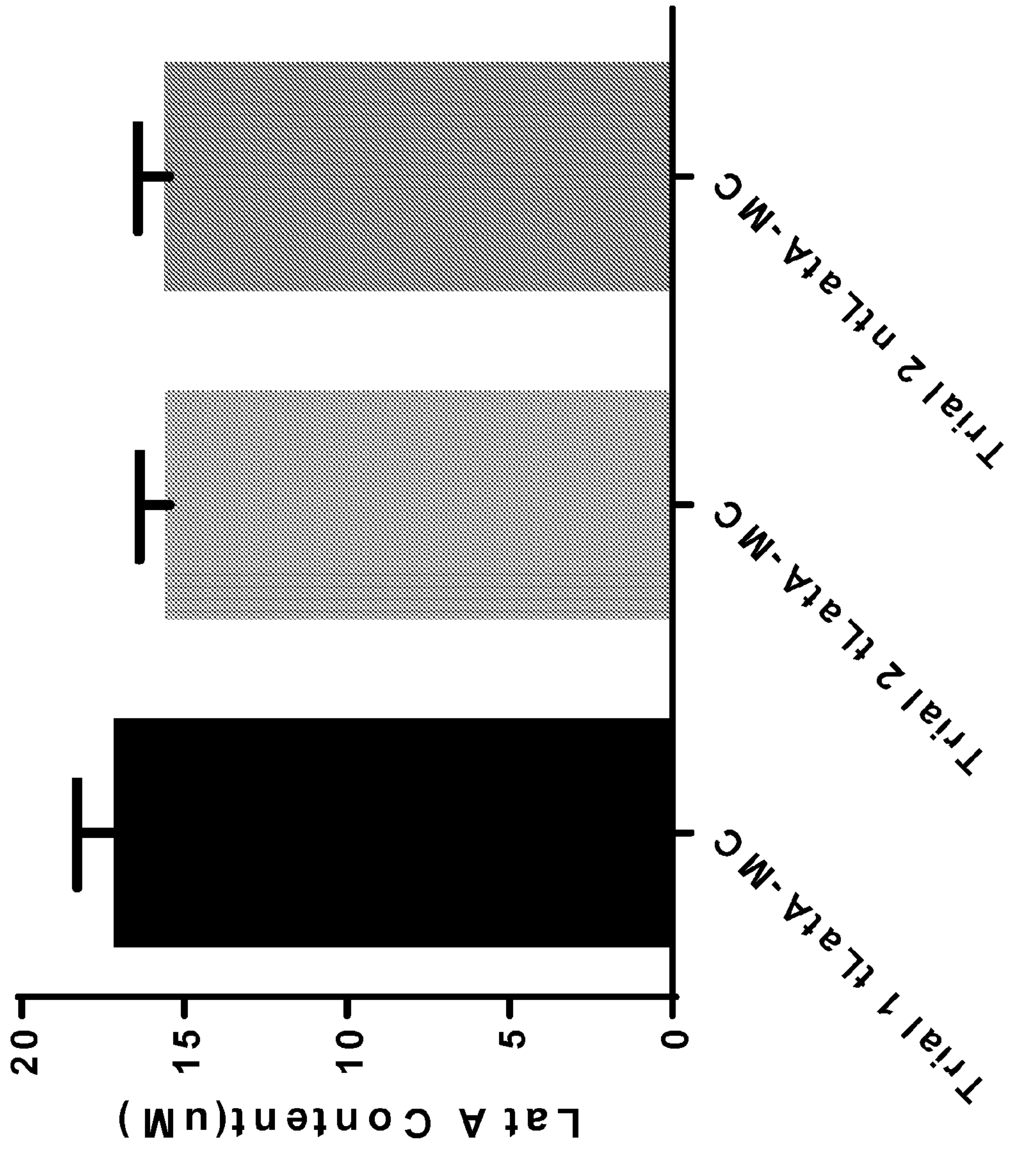
FIG. 6 shows the latrunculin A content of the 3 latrunculin-containing micelle formulations used in mouse studies. Latrunculin A content of targeted (t) or non-targeted (nt) LatA-MC formulations was determined by HPLC (Abs 234 nm). No significant differences were found between the two trials. Data are shown as mean±SD (N=3 technical replicates) and significance was determined by unpaired student's t-test.
Figure 7:
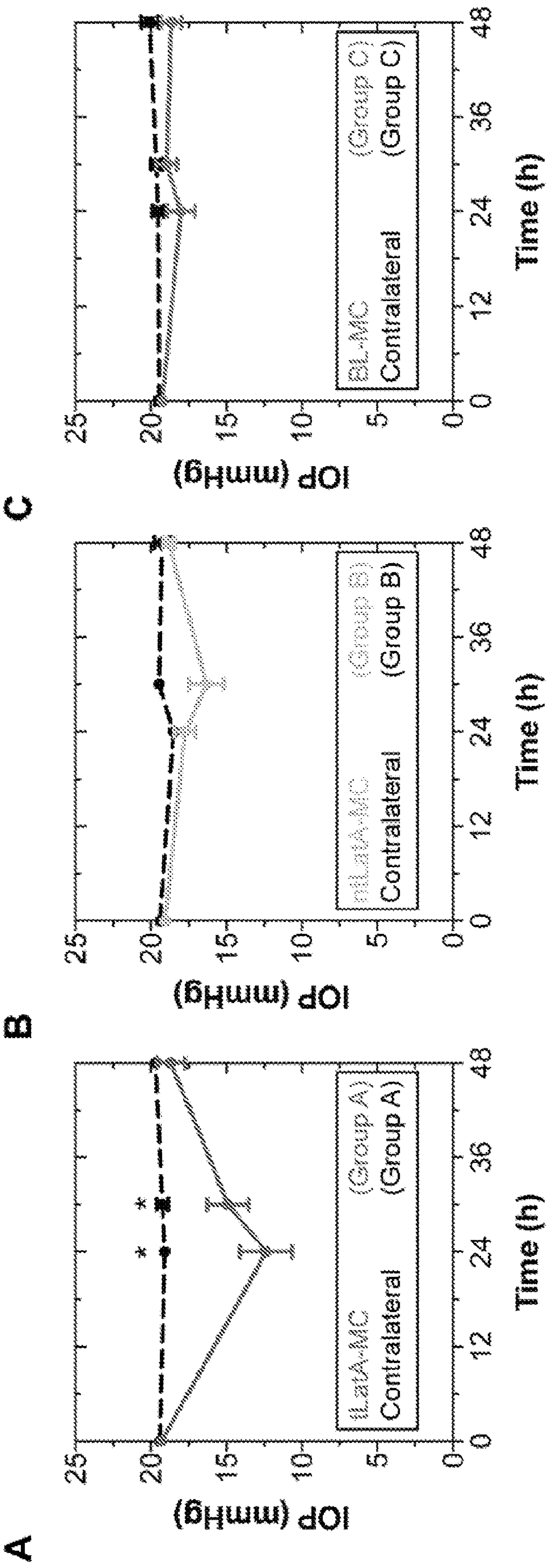
FIG. 7 shows the contralateral eye IOP recorded in trial #2. 2 μL of BL-MC (40 mg/mL polymer), ntLatA-MC (15.5 μM latrunculin A, 40 mg/mL polymer), or tLatA-MC (15.5 μM latrunculin A, 40 mg/mL 5% peptide) was injected into 1 eye of 5 mice each. IOP was measured in contralateral mouse eyes at 24, 30, and 48 hours post injection. The contralateral eye pressures for the (A) tLatA-MC, (B) ntLatA-MC, and (C) BL-MC groups are displayed. Significance was determined using paired t-test, n=5, *p<0.01.

We further evaluated the in vivo efficacy of tLatA-MC in a second trial designed to include non-targeted latrunculin A-loaded micelles, ntLatA-MC (FIG. 3A). Trial 2 revealed that tLatA-MC significantly reduced IOP by 30% and 31% compared to ntLatA-MC and BL-MC, respectively, at 24 hours (FIG. 3C). LatA-MC concentrations for both trials can be found in FIG. 6. Contralateral eyes that did not receive injection showed a consistent baseline for all three groups (FIG. 7). These data indicate that incorporation of FLT4 peptide into latrunculin A-loaded micelle formulations significantly lowered IOP in mice whereas non-targeted micelles did not. These results confirmed our observations in cultured cells probed by AFM (FIG. 2D, E), where only peptide-targeted micelles significantly increased the efficacy of encapsulated latrunculin A.

In collaboration with Duke University, our group repeated our prior delivery of nanocarriers to the eyes of live mice with newly prepared micelle formulations to confirm the performance of targeted micelles in lowering intraocular pressure in mice. This study included the following treatment groups, which we administered to the eyes of mice: (i) latrunculin A-loaded micelles that displayed the original targeting peptide construct ("targeted latrunculin A micelles"), (ii) latrunculin A-loaded micelles that do not display peptide ("latrunculin A micelles"), and (iii) micelles that do not encapsulate latrunculin A and do not display the original peptide construct ("Blank MCs"). The significant results were as follows. The targeted latrunculin A micelles reduced intraocular pressure by 5.6±2.0 mmHg after 1 day compared to Blank micelles, and by 5.4±1.9 mmHg compared to latrunculin A micelles. The latrunculin A micelles and Blank micelles were not significantly different. These differences were statistically significant (*$p<0.05$). Collectively, these results demonstrate that the targeted latrunculin A micelles significantly reduce IOP in mice after 24 h, and this effect is dependent on the presence of the targeting peptide. At 30 h, the targeted latrunculin A micelles reduced 4.0±1.6 mmHg compared to the blank MC control. This result was significant (*$p<0.05$). At this 30 h timepoint, no other comparisons between treatment groups were statistically significant.

The lack of effect of ntLatA-MC alone was unexpected but could be due to increased uptake in trabecular meshwork cells of ntLatA-MC that leads to a lower than threshold dose of LatA to be delivered to SC cells. Additionally, SC cells are only moderately phagocytic[11], and the targeting peptide may be required to reach intracellular threshold concentrations necessary for therapeutic effect.

Conclusions

In conclusion, we have successfully developed a targeted PEG-b-PPS nanocarrier system loaded with actin depolymerizing/cell softening agent latrunculin A (tLatA-MC). These micellar nanocarriers were designed with an FLT4-binding peptide to target SC cells in the eye. This system can load a variety of hydrophobic drug payloads and targeting moieties. Interestingly, the tBL-MC showed a decrease in HUVEC uptake although tLatA-MC did not. This is to our knowledge a previously unreported phenomenon and suggest that we not only can target the SC cells, but greatly reduce non-specific binding. Further work also must be undertaken to determine if this phenomenon is limited to HUVECs.

The data indicating tLatA-MC reduced IOP in two sets of mouse trials demonstrates the potential clinical significance of this delivery platform. Further studies will be necessary to demonstrate that use of these targeted nanocarriers reduce off-target effects, as our data suggests, and to investigate use of this delivery platform in other settings, particularly those requiring targeted delivery of hydrophobic drugs.

Materials and Methods

Synthesis of PEG-b-PPS block co-polymer. Nanocarriers were fabricated from a PEG-b-PPS copolymer which self assembles into various morphologies in a controllable way based on the molecular weight ratio of the hydrophilic PEG block to the hydrophobic PPS block. Block copolymers, $PEG_{45}$-b-$PPS_{23}$, were synthesized as previously described[17-18]. Briefly, PEG thioacetate was deprotected using sodium methoxide and subsequently used to initiate anionic ring opening polymerization of propylene sulfide. The reaction was allowed to run to completion and the resulting poly-propylene sulfide was end-capped using bromo benzene. The resulting polymer was precipitated twice in methanol for purification and then its structure was evaluated using 1H NMR (CDCL3) and gel permeation chromatography (Thermo Fisher Scientific) using a Waters Styragel column with refractive index and UV-Vis detectors in a tetrahydrofuran mobile phase.

Synthesis of FLT4 targeting peptide constructs. FLT4 peptide (WHWLPNLRHYAS (SEQ ID NO: 1)) was synthesized on a 0.5 mmol scale on Wang Resin (EMD Millipore) using standard Fmoc solid phase peptide synthesis (SPPS) and FastMoc chemistry (Applied Biosystems). Resins were swelled in N-methyl-2-pyrrolidinon (NMP) for 2 hours and Fmoc moieties were deprotected using 20% piperidine in NMP for 20 minutes. Fmoc protected amino acids (2.5-3.5 eq.) were added stepwise with 2-(1H-Benzotriazol-1-ly)-1,1,3,3,-tetramthyluronium hexafluorophosphate (HBTU, 2.5-3.5 eq) and N,N-diisopropylethyleamine (DIPEA, 4 eq) as a solvent by shaking for 3 hours at room temperature. After the final fmoc peptide was added and deprotected, Fmoc protected PEG spacer (Fmoc-PEG6-COOH, 2 eq) was added to couple with the free peptide amine group (HBTU, 2.5 eq, DIPEA, 4 eq) and allowed to shake for 4 hours. The PEG spacer was then deprotected using 20% piperidine and coupled with 3 eq of palmitoleic acid (HBTU, 2.5 eq, DIPEA, 4 eq) and allowed to react overnight while shaking. Coupling and deprotection of each amino acid and PEG spacer was verified by Ninhydrin test (Sigma). Deprotection of side chains and cleavage from the resin was done using Fmoc cleavage cocktail TFA/phenol/water/triisopropylsilane (TIPS) (88/5/5/2) twice for 2 hours each. Unpurified products were isolated by double precipitation in ice cold diethyl ether and subsequently purified at the Simpson Querrey Institute (SQI) peptide synthesis core by using RP-HPLC (Water-acetonitrile gradient, C18 column). Purified peptide construct was mixed with α-cyano-4-hydroxycinnamic acid (CHCA) prepared with acetonitrile/water (50:50, v/v) with 0.1% trifluoroacetic acid and molecular weight was determined by MALDI-TOF on a Bruker Autoflex III Smartbeam Spectometer (Bruker).

Assembly and loading of PEG-b-PPS micelles. Micelles were assembled from PEG-b-PPS block copolymer by a previously described cosolvent method[11-35]. $PEG_{45}$-b-$PPS_{23}$ block copolymer, 10 μg latrunculin A (Cayman Chemical), and 6 μL DiI (Thermo Fisher Scientific) were dissolved in 1 mL dichloromethane (DCM). The resulting DCM solution was added dropwise to a scintillation vial containing 1 mL sterile PBS stirred vigorously. DCM was allowed to evaporate for 2 hours. The resulting micelle suspensions were then prepared for addition of peptide or set aside for later purification. To achieve precise control of the peptide density on the surface of the micelle, FLT4/PEG/Palmitoleic acid constructs were added to already formed micelles at the desired molar ratio (1%, 3%, 5%). The appropriate amount of peptide construct was dissolved in DMSO, added to the micelles, and allowed to shake overnight. Resulting micelle formulations were then purified by gravity column chromatography using a Sephadex LH-20 column (Sigma-Aldrich) with a PBS mobile phase. Gravity column filtered micelles were then further purified and concentrated using 10 k MWCO Zebaspin desalting columns (Thermo Fisher).

Size and charge of micelle formulations. Size distribution, and polydispersity index (PDI) of the micelle formulations were analyzed by Zetasizer Nano (Malvern Instruments) using a 4 mW He-Ne 633 nm laser at 1 mg/mL in PBS. PDI was determined using a two-parameter fit to the DLS correlation data. The number average nanoparticle diameter was calculated in MATLAB (MathWorks; version R2018a).

Scanning transmission electron microscopy (STEM). Micelle samples were diluted in ultrapure water to a polymer concentration of 5 mg/mL. Carbon-coated copper grids (400 mesh; Electron Microscopy Sciences) were glow discharged (25 W, 10 s) and the micelle formulation was applied subsequently. Micelles were negatively stained using uranyl formate (1.0% prepared in ultrapure water; pH adjusted to 4.5 via addition of 10 N KOH). In this procedure, sample-loaded grids are blotted with Whatman filter paper to remove excess sample and are subjected to two passages through water followed by two passages through 1.0% UF stain. This procedure results in ~0.5 μl stain left on the grid, with an activity of 2.55×10−5 μKi/grid. Electron micrographs of negatively stained specimens were acquired on a Hitachi HD-2300 Dual EDS Cryo STEM operating at 200 kV (field emission gun) and Gatan DigitalMicrograph Software. Unless otherwise indicated, images were obtained at a magnification of 200,000×. All .dm3 files were processed in ImageJ software with basic, routine adjustment for figure preparation (overall brightness level and gamma adjustment).

Small angle x-ray scattering (SAXS) using synchrotron radiation. SAXS was performed at the DuPont-Northwestern-Dow Collaborative Access Team (DND-CAT) beamline at the Advanced Photon Source at Argonne National Laboratory (Argonne, IL, USA), using a 7.5 m sample-to-detector distance, 10 keV (λ=1.24 Å) collimated x-rays, and an exposure time of 3 s. Scattering was analyzed in the q-range of 0.001-0.5 $Å^{-1}$, calibrated using silver behenate diffraction patterns. Eq. 1 defines the momentum transfer vector (q), where θ is the scattering angle:

$$q = 4\pi\frac{\sin(\theta)}{\lambda} \tag{1}$$

The obtained data was reduced in PRIMUS software (version 2.8.3.) and model fitting was performed using SasView (version 5.0) software. A core shell sphere model was fit to micelle scattering profiles:

$$F(q) = \frac{3}{V_s}\left[V_c(\rho_c - \rho_s)\frac{\sin(qr_c) - qr_c\cos(qr_c)}{(qr_c)^3} + V_s(\rho_s - \rho_{solv})\frac{\sin(qr_2) - qr_s\cos(qr_s)}{(qr_s)^3}\right] \tag{2}$$

Where F is the structure factor, q is the momentum transfer vector (Eq. 1), $V_s$ is the particle volume ($Å^3$), $V_c$ is the particle core volume ($Å^3$), $\rho_c$ is the core scattering length density ($10^{-6}$ $Å^{-2}$), ρs is the shell scattering length density ($10^{-6}$ $Å^{-2}$), $\rho_{solv}$ is the solvent scattering length density ($10^{-6}$ $Å^{-2}$), $r_c$ is the core radius (Å). The shell thickness ($r_t$; in Å) is determined from the radius of the total particle ($r_s$; in Å) from Eq. 3:

$$r_s = r_c + r_t \tag{3}$$

Prior to performing more extensive parameter fitting procedures, the number-average micelle diameter determined by DLS was used to select initial core radius and shell thickness parameter values. Optimal model parameters were iteratively fit using the Levenberg-Marquardt algorithm in a chi square ($X^2$) minimization procedure. For core shell sphere models, a good model fit is indicated by $X^2<1.0$. For all models presented in this study, $X^2<0.1$ was obtained for the final model fit.

Drug loading characterization. Latrunculin A encapsulation efficiency was determined using a previously described method[11] in which 100 μL of concentrated and purified micelles were frozen at −80° C. and then lyophilized overnight. Latrunculin A was then extracted from the resulting lyophilized cake using methanol. After 1 h of extraction, the resulting suspension was centrifuged for 5 min at 4000×g and the supernatant latrunculin A content was evaluated by high performance liquid chromatography (HPLC). A static Methanol:Water (95:5) mobile phase was used on an Agilent C18 XDB-Eclipse column with absorption (235 nm) used to evaluate latrunculin A concentration. Standard curves were generated through serial dilution of latrunculin A with each of the resulting latrunculin A standards undergoing the same lyophilization and methanol extraction procedure described above.

Quantification of embedded targeting peptide. Peptide incorporation into the micelle was determined using fluorescence spectroscopy (SpectraMax M3; Molecular Devices). 100 μL of purified and concentrated micelles containing peptide were added to a black clear bottom 96 well plate in triplicate and tryptophan fluorescence at 270/350 nm (Ex/Em) was measured and compared to a standard curve to determine peptide incorporation. Blank micelle baseline was subtracted from raw values obtained for micelles displaying peptide. A standard curve was generated through serial dilution of DMSO-dissolved peptide in PBS of a paired peptide solution for each specific micelle batch. The final standard curve was prepared by background subtracting PBS.

Cell culture. Normal SC cells (SC71) were obtained from the lab of Dr. Dan Stamer. The protocol for extraction and isolation of these cells is described in detail elsewhere[32]. Extracted cells were shipped overnight in T25 cell culture flasks filled with low glucose DMEM (Life Technologies)+10% fetal bovine serum (Atlanta Biologicals) and 1% penicillin/streptomycin (Life technologies). Immediately upon arrival, cells media was refreshed and cells were stored at 37° C. and 5% $CO_2$ until 80% confluent. Cells were passaged using a standard trypsinization procedure and were split at a 1:3 ratio when 80% confluent. SC cells were used at passage 4 and 5 in all experiments. Human Umbilical Vein Endothelial Cells (HUVEC) were cultured in Endothelial Growth Media (Lonza). Cells were passaged at a 1:3 ratio using trypsinization when 75-80% confluent.

In vitro cell uptake assay. SC cells and/or HUVECs adhered to 24 well tissue culture treated polystyrene plates (Falcon), were treated with DiI (Thermo) loaded micelles with or without latrunculin A and with or without FLT4 targeting peptide (1%, 3%, 5%) were added to each well for 2 hours at 37° C. After incubation, cells were washed with PBS and harvested using trypsinization. Cells were stained with Zombie Aqua cell viability dye and then washed and fixed with IC cell fixation buffer (BioLegend). Flow cytometry was performed using FACS diva on a BD Aria flow cytometer (BD biosciences). Untreated cells of both types were used to subtract out background fluorescence and flow data were analyzed using Cytobank software (Cytobank).

Atomic force microscopy on cultured Schlemm's canal cells. SC cells were grown in 60 mm petri-dishes (VWR) for 48 hours prior to experiment and were 80% confluent at the time of measurement. AFM measurements were made using a BioScope II with NanoscopeV controller (Bruker) coupled to an inverted fluorescent microscope with 10× (NA=0.3), 20× (NA=0.8) objective lens. Spherical polystyrene probes with a diameter of 10 μm (Novascan Technologies) mounted on silicon nitride cantilever with nominal spring constant of 0.01 N/m. The cantilever spring constant was calibrated prior to measurement using the Thermal Tune module of the Nanoscope. Throughout the duration of the experiment, SC cells were maintained with previously described cell culture media in an incubator at 37° C. To avoid substrate effects, indentation depth was restricted to 400 nm or less and the tip velocity was set to 800 nm/s to avoid viscous effects. Force measurements were performed at regions away from the nucleus and cell periphery to avoid confounding effects from either. Each cell was only probed one time and a minimum of 15 measurements was made for each sample group. Data from these AFM measurements were used to extract force versus indentation curves and the Hertz model was then utilized to calculate the Young's Modulus of the cells as we have previously described[11,36].

Figure 8:
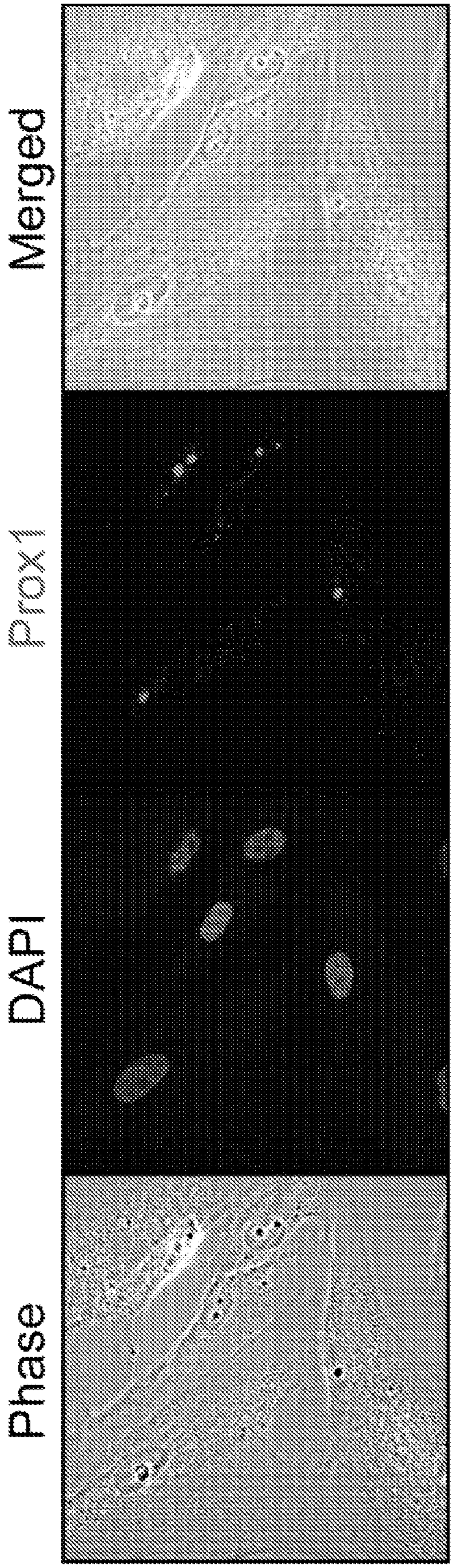
FIG. 8 shows PROX1 expression by SC endothelial cells. SC endothelial cells were stained with Hoescht 33342 (blue) and with anti-PROX1 antibody (pink) and were imaged by confocal microscopy. Representative phase contrast images of the SC cells are displayed together with fluorescence channels (magnification=60×). Prox1 was found to be expressed intracellularly on SC cells.

Confocal microscopy. SC cells were seeded in sterile 8 well confocal chamber slides (Thermo) and were allowed to grow in media for 24 hours prior to treatment. On the day of the experiment, fresh culture media was added containing anti-FLT4 PE conjugated antibody (Biolegend) and allowed to incubate with cells for 2 hours. Chamber slides were then washed with PBS and fixed using 4% paraformaldehyde (Electron Microscopy Sciences, Hatfield, PA) for 10 minutes at room temperature. Fixed cells were rinsed with PBS twice and then stained with Hoechst 33342 (1:10000) (Thermo) for 10 minutes. After rinsing 2 more times with PBS, fixed cells were imaged using a Zeiss 510 LSM inverted confocal microscope. Additionally, the same procedure was followed to examine Prox1 expression on SC cells as another possible targeting marker. SC cells were permeabilized using 100% methanol and subsequently stained with rabbit anti-PROX1 antibody (Abcam) along with a goat anti-rabbit IgG H&L (HRP) secondary antibody (Abcam). Prox1 was not expressed on the surface of SC cells (FIG. 8).

Figure 4:
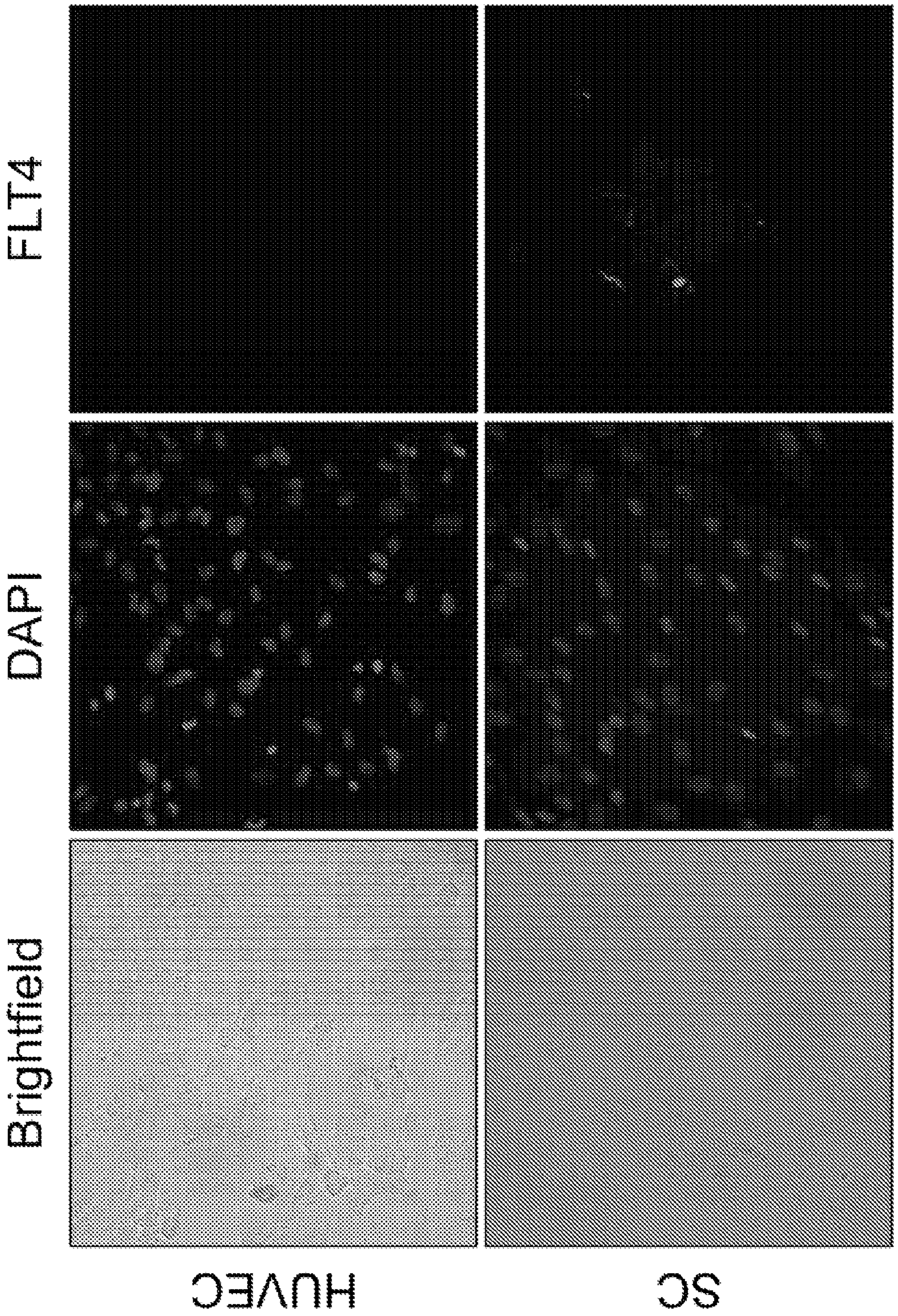
FIG. 4 shows widefield fluorescence microscopy of FLT4 expression in HUVECs and SC cells. Cells were stained with anti-VEGFR3/FLT4-APC to detect FLT4 expression. Representative images from brightfield, DAPI, and Cy5 channels are displayed. Magnification=40×.

Widefield fluorescence microscopy on live cells. HUVECs and SC cells were plated at a density of 20,000 cells/well in glass-bottom 96-well plates (Greiner) and were allowed to adhere for 24 h prior to analysis. Cells were treated with anti-CD16/32 to block non-specific Fc receptor binding and were subsequently stained using anti-human VEGFR3/F1t4-APC antibody (BioLegend) per manufacturer recommendation. Cells were washed and stained with NucBlue (Hoechst 33342; cell permeable nuclear stain) prior to imaging. Widefield fluorescence microscopy images were obtained on ImageXpress High Content Imaging Robotic Platform (Molecular Devices). Images were acquired using the brightfield, DAPI, and Cy5 channels (magnification=40,000×). FLT4 was not expressed by HUVECs but was detectable on the surface of the SC cells (FIG. 4).

Flow cytometric characterization of FLT4 expression. SC cells and HUVECs were seeded in tissue culture treated 12 well polystyrene plates and maintained in their respective cell culture media at 37° C. until 80% confluent at which point they were harvested by trypsinization and transferred to flow tubes. Cells were spun down at 400×g for 5 minutes and supernatant was removed. Cells were then incubated with Zombie Aqua cell fixability dye (1:100) (Thermo) for 15 minutes and then Anti-FLT PE antibody was added and allowed to incubate for 30 minutes. Cells were then spun down and fixed using IC fixation buffer (Biolegend). After fixation, flow cytometry was performed using FAC Sdiva on a FACS Aria flow cytometer (BD biosciences). PE median fluorescence intensity for live cells was determined using Cytobank software (Cytobank).

Animals. C57BL/6 (C57) mice were purchased from the Jackson Laboratory, bred/housed in clear cages, and kept in housing rooms at 21° C. with a 12 h:12 h light:dark cycle.

Intraocular pressure measurements. The mice were anesthetized with ketamine (60 mg/kg) and xylazine (6 mg/kg). IOP was measured immediately upon cessation of movement (i.e., in light sleep) using rebound tonometry (TonoLab; Icare). Each recorded IOP was the average of six measurements, giving a total of 36 rebounds from the same eye per recorded IOP value. IOP was conducted prior and post 24, 30 and 48 h nanoparticle injection.

Nanoparticles (NPs) injection. Three-month-old male C57 mice were randomly selected into three groups (A, B and C, 5 mice/group). The mice were anesthetized with an intraperitoneal injection of ketamine (100 mg/kg) and xylazine (10 mg/kg). A drop of 0.5% proparacaine, a topical anesthetic, was applied to the injection eye. A pulled micro-glass needle filled with NPs (labeled with A, B or C) and connected to a pump was inserted in one of the mouse anterior chambers (another non-treated eye was used as the contralateral control). Two microliters of the nanoparticles were infused in the mouse anterior chamber at a rate of 0.67 μl/min. After infusion, the needle was withdrawn, and topical erythromycin antibiotic ointment was applied to the infused eye. All the mice were maintained on a warm water-circulating blanket until they had recovered from the anesthesia and then returned to the animal housing rack.

Statistical analysis. All statistical analyses were performed using GraphPad Prism software (GraphPad Software; version 8.4.1). Each figure notes the specific type of statistical test utilized to determine statistical significance.

TABLE 1

Physical characteristics of nanoparticles as determined by DLS and HPLC

| | BL-MC | ntLatA-MC | tLatA-MC |
|---|---|---|---|
| Diameter [nm][a)] | 15.2 ± 4.1 | 20.0 ± 5.4 | 15.8 ± 3.6 |
| PDI | 0.07 | 0.07 | 0.05 |
| Loading efficiency | N/A | 62.5% | 62.5% |

[a)]The number average diameter is presented.

Reference is made to Stack et al., "Targeted Delivery of Cell Softening Micelles to Schlemm's Canal Endothelial Cells for Treatment of Glaucoma", Small 2020, 16, 43, 2004205, the content of which his incorporated by reference in entirety.

REFERENCES FOR EXAMPLE 1

[1] H. A. Quigley, A. T. Broman, *Br J Ophthalmol* 2006, 90, 262.
[2] D. R. Overby, E. H. Zhou, R. Vargas-Pinto, R. M. Pedrigi, R. Fuchshofer, S. T. Braakman, R. Gupta, K. M. Perkumas, J. M. Sherwood, A. Vahabikashi, Q. Dang, J. H. Kim, C. R. Ethier, W. D. Stamer, J. J. Fredberg, M. Johnson, *Proc Natl Acad Sci USA* 2014, 111, 13876.
[3] A. Vahabikashi, A. Gelman, B. Dong, L. Gong, E. D. K. Cha, M. Schimmel, E. R. Tamm, K. Perkumas, W. D. Stamer, C. Sun, H. F. Zhang, H. Gong, M. Johnson, *PNAS* 2019, 116, 26555.
[4] A. P. Tanna, M. Johnson, *Ophthalmology* 2018, 125, 1741.
[5] J. A. Peterson, B. Tian, A. D. Bershadsky, T. Volberg, R. E. Gangnon, I. Spector, B. Geiger, P. L. Kaufman, *Invest. Ophthalmol. Vis. Sci.* 1999, 40, 931.
[6] V. Andrés-Guerrero, J. Garcia-Feijoo, A. G. Konstas, *Adv Ther* 2017, 34, 1049.
[7] A. P. Tanna, H. Esfandiari, K. Teramoto, *J. Glaucoma* 2020, DOI 10.1097/HG.0000000000001507.
[8] S. Yi, X. Zhang, M. H. Sangji, Y. Liu, S. D. Allen, B. Xiao, S. Bobbala, C. L. Braverman, L. Cai, P. I. Hecker, M. DeBerge, E. B. Thorp, R. E. Temel, S. I. Stupp, E. A. Scott, *Advanced Functional Materials* 2019, 29, 1904399.
[9] J. Yoo, C. Park, G. Yi, D. Lee, H. Koo, *Cancers* 2019, 11, 640.
[10] E. A. Scott, N. B. Karabin, P. Augsornworawat, *Annu Rev Biomed Eng* 2017, 19, 57.
[11] T. Stack, A. Vahabikashi, M. Johnson, E. Scott, *J Biomed Mater Res A* 2018, 106, 1771.
[12] S. D. Allen, Y.-G. Liu, T. Kim, S. Bobbala, S. Yi, X. Zhang, J. Choi, E. A. Scott, *Biomater. Sci.* 2019, 7, 657.
[13] S. D. Allen, Y.-G. Liu, S. Bobbala, L. Cai, P. I. Hecker, R. Temel, E. A. Scott, *Nano Res.* 2018, 11, 5689.
[14] I. Spector, N. R. Shochet, D. Blasberger, Y. Kashman, *Cell Motil. Cytoskeleton* 1989, 13, 127.
[15] J. A. Peterson, B. Tian, J. W. McLaren, W. C. Hubbard, B. Geiger, P. L. Kaufman, *Invest. Ophthalmol. Vis. Sci.* 2000, 41, 1749.
[16] C. A. Rasmussen, P. L. Kaufman, R. Ritch, R. Hague, R. K. Brazzell, J. L. Vittitow, *Transl Vis Sci Technol* 2014, 3, DOI 10.1167/tvst.3.5.1.
[17] E. A. Scott, A. Stano, M. Gillard, A. C. Maio-Liu, M. A. Swartz, J. A. Hubbell, *Biomaterials* 2012, 33, 6211.
[18] S. Yi, S. D. Allen, Y.-G. Liu, B. Z. Ouyang, X. Li, P. Augsornworawat, E. B. Thorp, E. A. Scott, *ACS Nano* 2016, 10, 11290.
[19] N. B. Karabin, S. Allen, H.-K. Kwon, S. Bobbala, E. Firlar, T. Shokuhfar, K. R. Shull, E. A. Scott, *Nature Communications* 2018, 9, 624.
[20] A. E. Vasdekis, E. A. Scott, C. P. O'Neil, D. Psaltis, Jeffrey. A. Hubbell, *ACS Nano* 2012, 6, 7850.
[21] S. Allen, M. Vincent, E. Scott, *J Vis Exp* 2018, DOI 10.3791/57793.
[22] S. Bobbala, S. D. Allen, S. Yi, M. Vincent, M. Frey, N. B. Karabin, E. A. Scott, *Nanoscale* 2020, 12, 5332.
[23] S. Yi, N. B. Karabin, J. Zhu, S. Bobbala, H. Lyu, S. Li, Y. Liu, M. Frey, M. Vincent, E. A. Scott, *Front Bioeng Biotechnol* 2020, 8, DOI 10.3389/fbioe.2020.00542.
[24] S. Bobbala, S. D. Allen, E. A. Scott, *Nanoscale* 2018, 10, 5078.
[25] A. Stano, E. A. Scott, K. Y. Dane, M. A. Swartz, J. A. Hubbell, *Biomaterials* 2013, 34, 4339.
[26] D. J. Dowling, E. A. Scott, A. Scheid, I. Bergelson, S. Joshi, C. Pietrasanta, S. Brightman, G. Sanchez-Schmitz, S. D. Van Haren, J. Ninković, D. Kats, C. Guiducci, A. de Titta, D. K. Bonner, S. Hirosue, M. A. Swartz, J. A. Hubbell, O. Levy, *J. Allergy Clin. Immunol.* 2017, 140, 1339.
[27] M. P. Vincent, S. Bobbala, N. B. Karabin, M. Frey, Y. Liu, J. O. Navidzadeh, T. Stack, E. A. Scott, *bioRxiv* 2020, 2020.04.24.060772.
[28] A. S. Piotrowski-Daspit, A. C. Kauffman, L. G. Bracaglia, W. M. Saltzman, *Advanced Drug Delivery Reviews* 2020, DOI 10.1016/j .addr.2020.06.014.
[29] A. Aspelund, T. Tammela, S. Antila, H. Nurmi, V.-M. Leppanen, G. Zarkada, L. Stanczuk, M. Francois, T. Mäkinen, P. Saharinen, I. Immonen, K. Alitalo, *J Clin Invest* 2014, 124, 3975.
[30] C. N. Dautriche, Y. Tian, Y. Xie, S. T. Sharfstein, *Journal of Functional Biomaterials* 2015, 6, 963.
[31] K. Kizhatil, M. Ryan, J. K. Marchant, S. Henrich, S. W. M. John, *PLoS Biol.* 2014, 12, e1001912.
[32] W. D. Stamer, B. C. Roberts, D. N. Howell, D. L. Epstein, *Invest. Ophthalmol. Vis. Sci.* 1998, 39, 1804.
[33] L.-F. Shi, Y. Wu, C.-Y. Li, *J Gynecol Oncol* 2015, 26, 327.
[34] G. Sahay, E. V. Batrakova, A. V. Kabanov, *Bioconjug Chem* 2008, 19, 2023.
[35] S. Cerritelli, D. Velluto, J. A. Hubbell, *Biomacromolecules* 2007, 8, 1966.
[36] R. Vargas-Pinto, H. Gong, A. Vahabikashi, M. Johnson, *Biophys. J.* 2013, 105, 300.

Example 2

In Example 1, we developed a lipid-anchored targeting peptide that binds to FLT4/VEGFR3 receptors to target the delivery of cell softening agents to Schlemm's canal cells. FLT4 receptors are enriched on the Schlemm's canal endothelium in animal models[35], cultured Schlemm's canal cells derived from healthy human donors[34], and in human donor eyes by single cell RNA sequencing[36,37]. Despite this early work, multiple uncertainties remain regarding the use of a FLT4-targeting strategy. One uncertainty pertains to clinical utility and whether FLT4 receptors are expressed on the Schlemm's canal surface in the eyes of glaucoma patients to permit the targeted delivery of cell softening drugs. Second, to maximize the efficacy and minimize the side effects of these agents, it is important that the engineered vehicles optimally deliver drug payloads to Schlemm's canal cells instead of off-target endothelial cell types, in particular the corneal endothelium. Regarding our initial Schlemm's canal-targeting approach, steric considerations involving the PEG chains of the drug delivery vehicle chassis and their potential for obstructing receptor access to the peptide ligand motivated us to rationally design alternative ligand structures to improve performance. Suboptimal receptor binding is a general problem with targeted drug delivery systems[38], and it is often left unresolved due to a lack of methods for optimizing ligand interactions at the nanocarrier surface. While useful insights into the role of ligand length on organ-level nanocarrier accumulation are available in the literature[39], empirical relationships between ligand steric effects at nanocarrier surfaces and their consequences on multiscale targeting performance and impact on clinically-relevant outcomes remains unestablished.

In the following Example, we address these issues by developing a novel assay to measure peptide accessibility to proteolysis, which enabled us to quantify the availability of ligands for binding events. We were particularly interested in determining whether lipid-anchored targeting constructs can be optimized to maximize binding to FLT4 receptors, and whether differences in receptor engagement produced measurable differences in drug delivery vehicle performance in a clinically relevant setting. Using a multidisciplinary approach that included molecular characterization, in vitro targeting studies and direct evaluation in a murine model, we examined the potential for these optimized nanotherapeutics to target a cell softening agent to Schlemm's canal in vivo and lower IOP. C57BL/6J mice were used as an animal model in these studies due to their similar conventional outflow pathway anatomy, physiology, and pharmacologic responses to humans[40-42]. This work holds important clinical implications for the use of cell softening nanotherapies as safe and efficacious tools for managing glaucoma. Furthermore, the rational design principles established herein, as well as the empirical evidence supporting their utility, can be harnessed to meet diverse challenges in drug delivery.

Results

Target validation: glaucomatous Schlemm's canal endothelial cells highly express FLT4/VEGFR3 receptors. The Schlemm's canal endothelium is somewhat unique in that it expresses both blood vascular and lymphatic characteristics[50]. FLT4 receptors are a lymphatic marker expressed by Schlemm's canal cells[35]. Developing strategies to promote nanocarrier interactions with FLT4 receptors offers a potential strategy for increasing their uptake by Schlemm's canal endothelial cells relative to blood vascular cells of the iris and ciliary body. While past studies detected FLT4 receptors on the surface of Schlemm's canal cells derived from normal human patients[34], it is unclear whether glaucoma alters the expression of these receptors. To determine whether FLT4 is a viable cell surface marker for targeting Schlemm's canal cells in patients with glaucoma, FLT4 expression was examined in two normal and two glaucomatous Schlemm's canal cell strains from human donors (FIG. 9*a*; Table 2).

Figure 9:
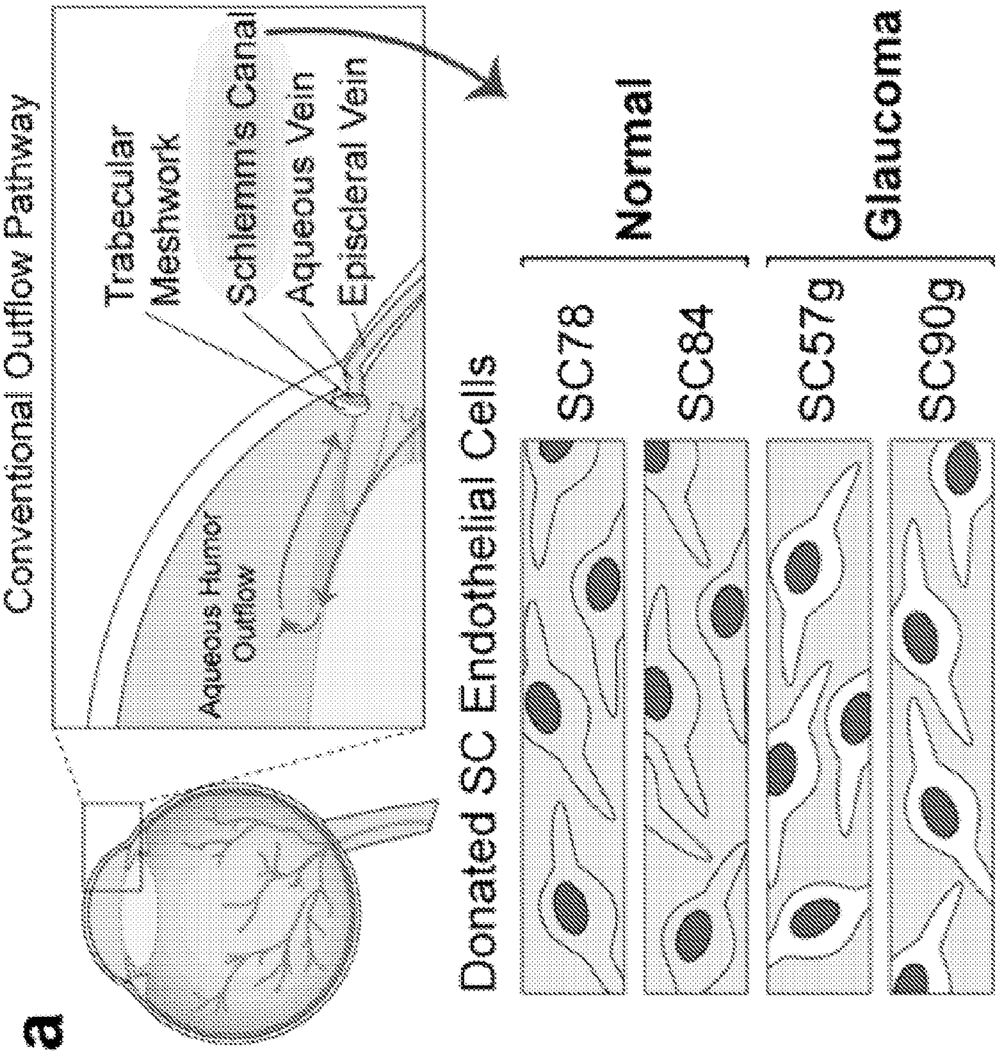
FIG. 9 demonstrates that normal and glaucomatous Schlemm's canal (SC) endothelial cells express FLT4/VEGFR3. (a) Illustration of FLT4/VEGFR3 expression test in two normal SC endothelial cell strains (SC 78, SC 84) and two glaucomatous SC cell strains (SC 57 g, SC 90 g). (b) Flow cytometric analysis of FLT4 expression in SC and SC g cell strains. HUVECs are included as a control endothelial cell line that does not express FLT4 at high levels. FLT4 expression was detected by staining cells with anti-human FLT4-APC antibody. Data is presented as mean±s.e.m. (n=3). Significant differences between SC and HUVEC FLT4 MFI were determined by ANOVA with Dunnett's multiple comparisons test (5% significance level). *p<0.05. (c) FLT4 expression observed by widefield fluorescence microscopy (40×). Brightfield images are shown together with the DAPI channel (cell nuclei) and Cy5 channel (anti-FLT4-APC). "Merge" denotes the merged DAPI and Cy5 channels. Scale bar=50 μm.
Figure 9:
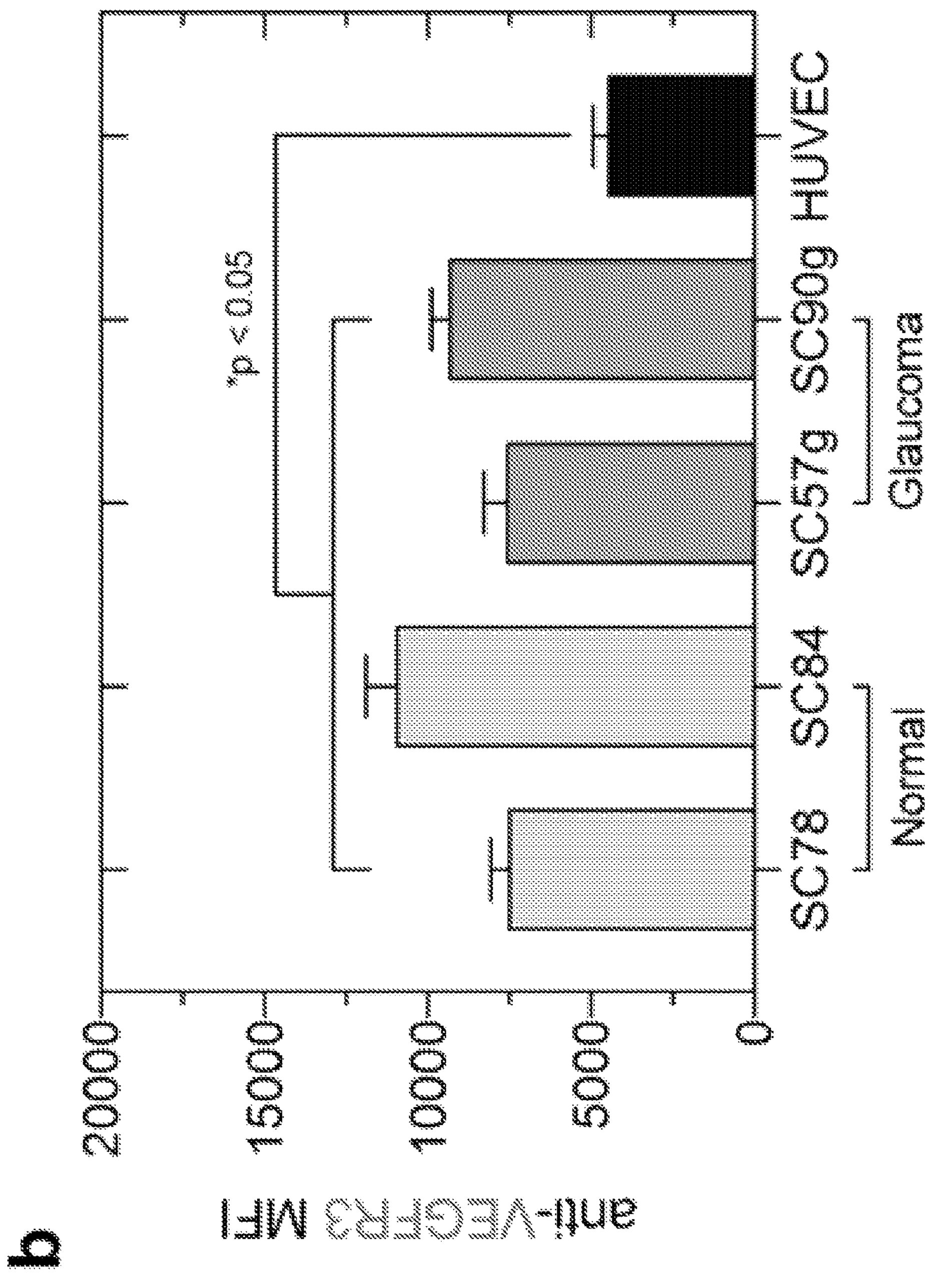
Figure 9:
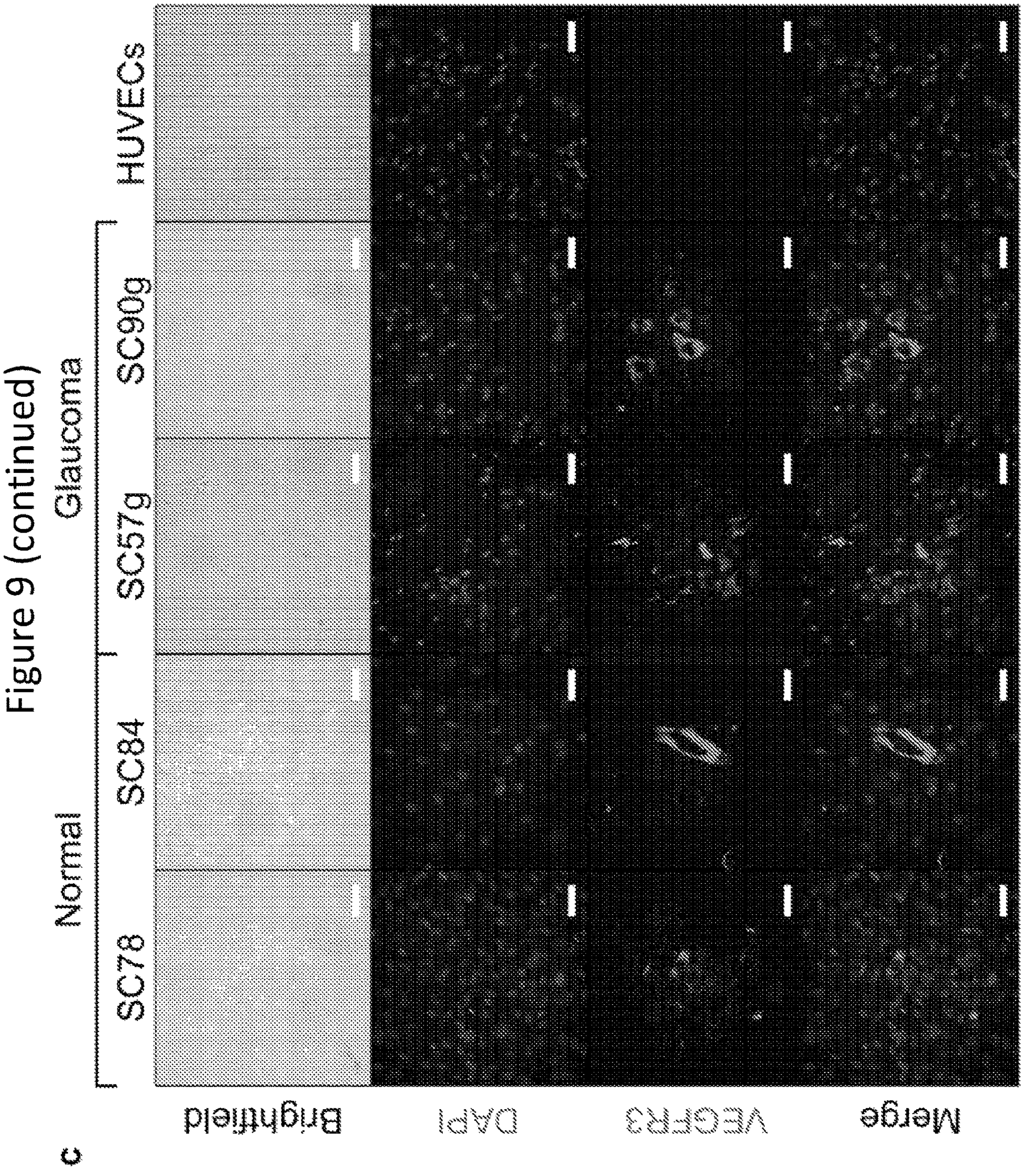

Schlemm's canal cells expressed FLT4 at significantly greater levels than human umbilical vein endothelial cells (HUVECs), a representative model of blood vascular endothelial cells, in both the normal and glaucomatous cell strains examined (FIG. 9*b,c*). Quantification of FLT4 expression by flow cytometry (FIG. 9*b*) was consistent with the FLT4 expression levels observed by widefield fluorescence microscopy (FIG. 9*c*). While low FLT4 expression was detected on HUVECs by flow cytometry, this lower expression level is below the limit of detection of the less sensitive fluorescence microscopy technique. The relatively high FLT4 expression by Schlemm's canal cells in the conventional outflow tissues', and its maintenance during glaucoma (FIG. 9), suggests FLT4 is available for targeting the delivery of IOP reducing agents directly to Schlemm's canal cells in glaucoma patients.

TABLE 2

Donated human Schlemm's canal (SC) endothelial cell lines used in this study

| Cell Line | Disease State | Age | Gender† | Race† | Dex Test†† | Eye Source | Eye Bank |
|---|---|---|---|---|---|---|---|
| SC 78 | Normal | 77 | Male | White | Negative | Whole eye | Kansas Eye Bank |
| SC 84 | Normal | 67 | NA | NA | Negative | Cornea | NC Eye Bank |
| SC 57g | Glaucoma | 78 | Male | NA | Negative | Whole eye | Life Legacy |
| SC 90g | Glaucoma | 71 | Female | White | Negative | Whole eye | NC Eye Bank |

†NA = Information not available

††Dex (dexamethasone) test. A negative Dex Test indicates a lack of myocilin induction upon treatment with dexamethasone, which is a response that is expected of SC cells and is used to distinguish isolated SC cells from the major possible contaminant, trabecular meshwork (TM) cells (a positive Dex Test is expected for TM cells).

Figure 14:
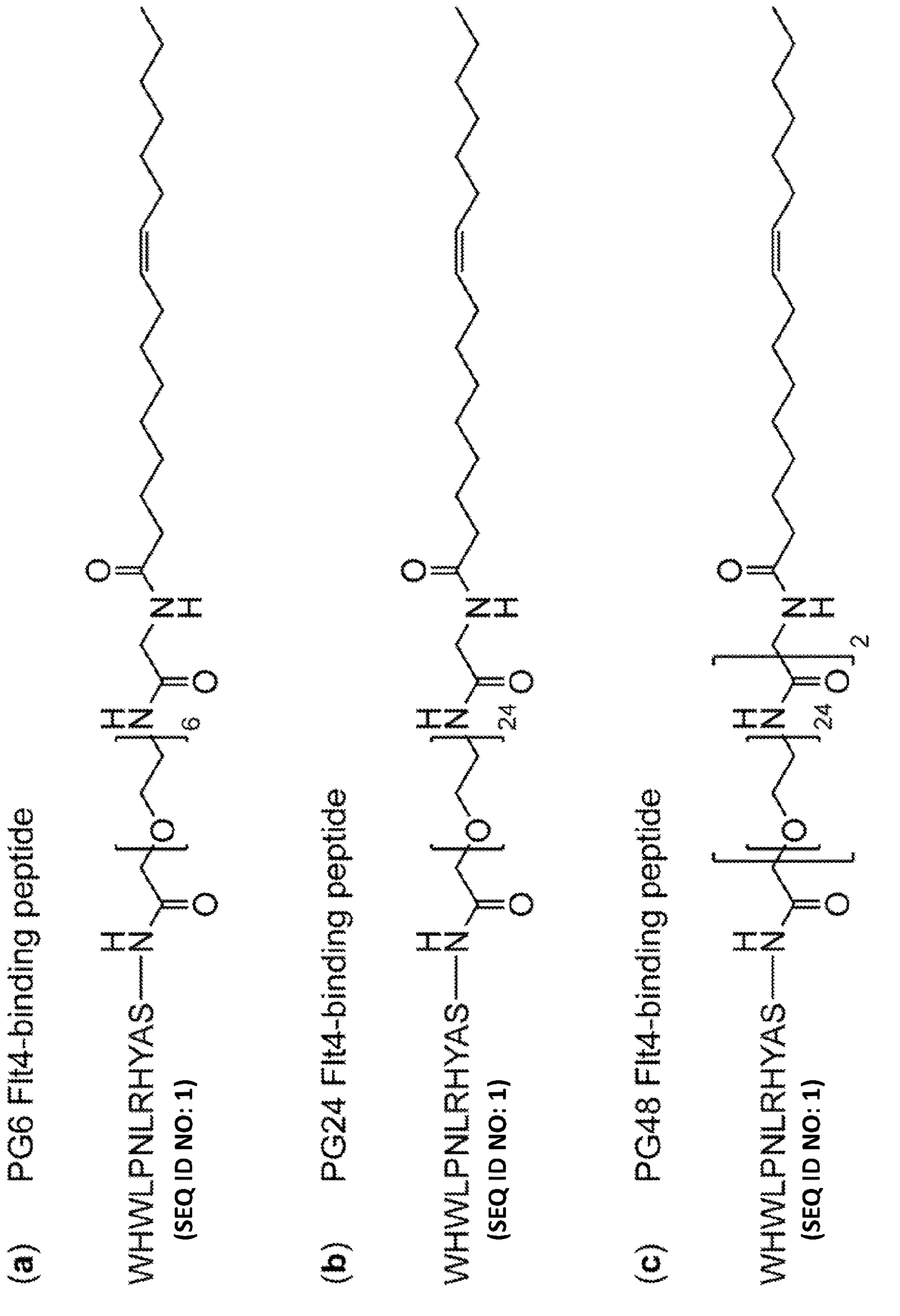
FIG. 14 is a depiction of the structures of the lipid-anchored FLT4-binding peptide constructs. Lipid anchored peptide constructs were synthesized in the form [palmitoleic acid]-[$PEG_x$ spacer]-[Flt4-binding peptide] (listed from N-terminus to C-terminus). The constructs differed by the length of their PEG spacers. (a) "PG6" Flt4-binding peptide (x=6 PEG units), (b) "PG24" Flt4-binding peptide (x=24 PEG units), and (c) "PG48" Flt4-binding peptide (x=24×2 PEG units).

Development of Schlemm's canal-targeted PEG-b-PPS micelles displaying optimized FLT4-binding peptides. The drug delivery vehicles developed in this work are polymeric micelles (MCs) self-assembled from oxidation-sensitive, amphiphilic poly(ethylene glycol)-b-poly(propylene sulfide) ($PEG_{45}$-b-$PPS_{23}$) diblock copolymers that employ a methoxy (—$OCH_3$) group at the terminus of the PEG hydrophilic block (FIG. 10*a-c*; Table 3). Our past studies established rational design principles for modulating protein corona formation in protein-rich biofluids and demonstrated the methoxy surface chemistry greatly reduces plasma protein adsorption to PEG-b-PPS micelle surfaces[51]. The methoxy surface chemistry was therefore used to minimize the adsorption of aqueous humor proteins, which are present at a relatively low concentration and are compositionally similar to plasma[52], since adsorbed protein layers would otherwise shield targeting ligands and hinder binding interactions. We hypothesized that the FLT4-binding peptides incorporating longer PEG spacers would more easily bind to the FLT4-binding receptors of the Schlemm's canal cells as the longer spacer would minimize obstruction by the 45-unit micelle PEG corona. To test this hypothesis, peptide constructs were designed with 6-(PG6), 24-(PG24) or 48-(PG48) unit PEG spacers (FIG. 10*d*; FIG. 14). Peptides were synthesized using standard Fmoc solid phase peptide synthesis and the resulting products were of high purity (≥95% purity; FIG. 10*d,e*). Dominant peaks of 2151.1 Da, 3046.7 Da, and 4071.4 Da are visible in the extracted mass spectra for PG6, PG24, and PG48, respectively, and these mass differences are consistent with the differences in the mass of the construct-specific PEG spacers (FIG. 10*e*; Table 4).

TABLE 3

| PEG-b-PPS Micelle (MC) diblock copolymer | | |
|---|---|---|
| BCP | $f_{PEG}$† | MW (g/mol) |
| MeO-$PEG_{45}$-b-$PPS_{19}$-Bn | 0.59 | 3,596 |

†Hydrophilic weight fraction of polymer.

TABLE 4

| FLT4-targeting peptide constructs | | | | | | |
|---|---|---|---|---|---|---|
| | Lipid | PEG Spacer††† | | Peptide primary | MW | Purity |
| Construct† | Anchor†† | Units | Length (Å) | structure‡‡ | (g/mol) | * |
| PG6 | PA | 6 | 25.046 | WHWLPNLRHYAS (SEQ ID NO: 1) | 2151.1 | >95% |
| PG24 | PA | 24 | 88.913 | WHWLPNLRHYAS (SEQ ID NO: 1) | 3046.7 | >95% |
| PG48 | PA | 48‡ | 174.058 | WHWLPNLRHYAS (SEQ ID NO: 1) | 4071.4 | >95% |

†All peptide constructs are of the form [Lipid]-[$PEG_X$ spacer]-[Peptide].
††Palmitoleic acid (PA).
†††The spacer length is presented as the number of PEG units.
‡The peptide construct with a 48-unit PEG spacer was synthesized using Fmoc-PEG24x2.
‡‡Peptide primary structure is listed N-terminus to C-terminus.
* Peptide purity determined using LC-MS.

Figure 15:
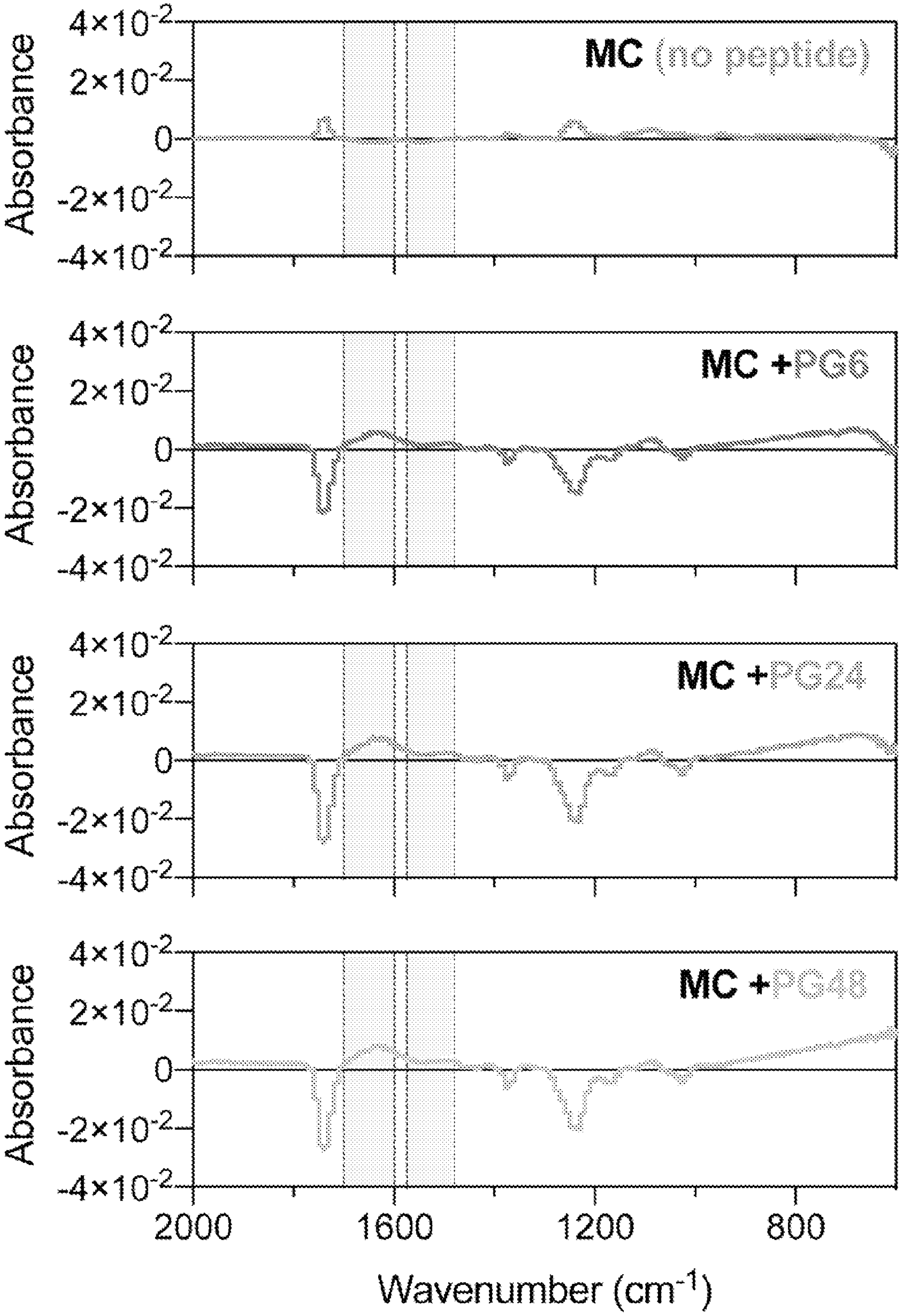
FIG. 15 shows Fourier-transform infrared (FTIR) spectroscopy spectra of purified micelle formulations. The FTIR spectra of phosphate buffered saline (i.e., background from the buffer) was subtracted from the spectra of each of the specified formulations. In each case, the average spectrum is presented from a total of 64 scans. The amide I (1700-1600 $cm^{-1}$) and amide II (1590-1520 $cm^{-1}$) bands are highlighted in yellow.
Figure 16:
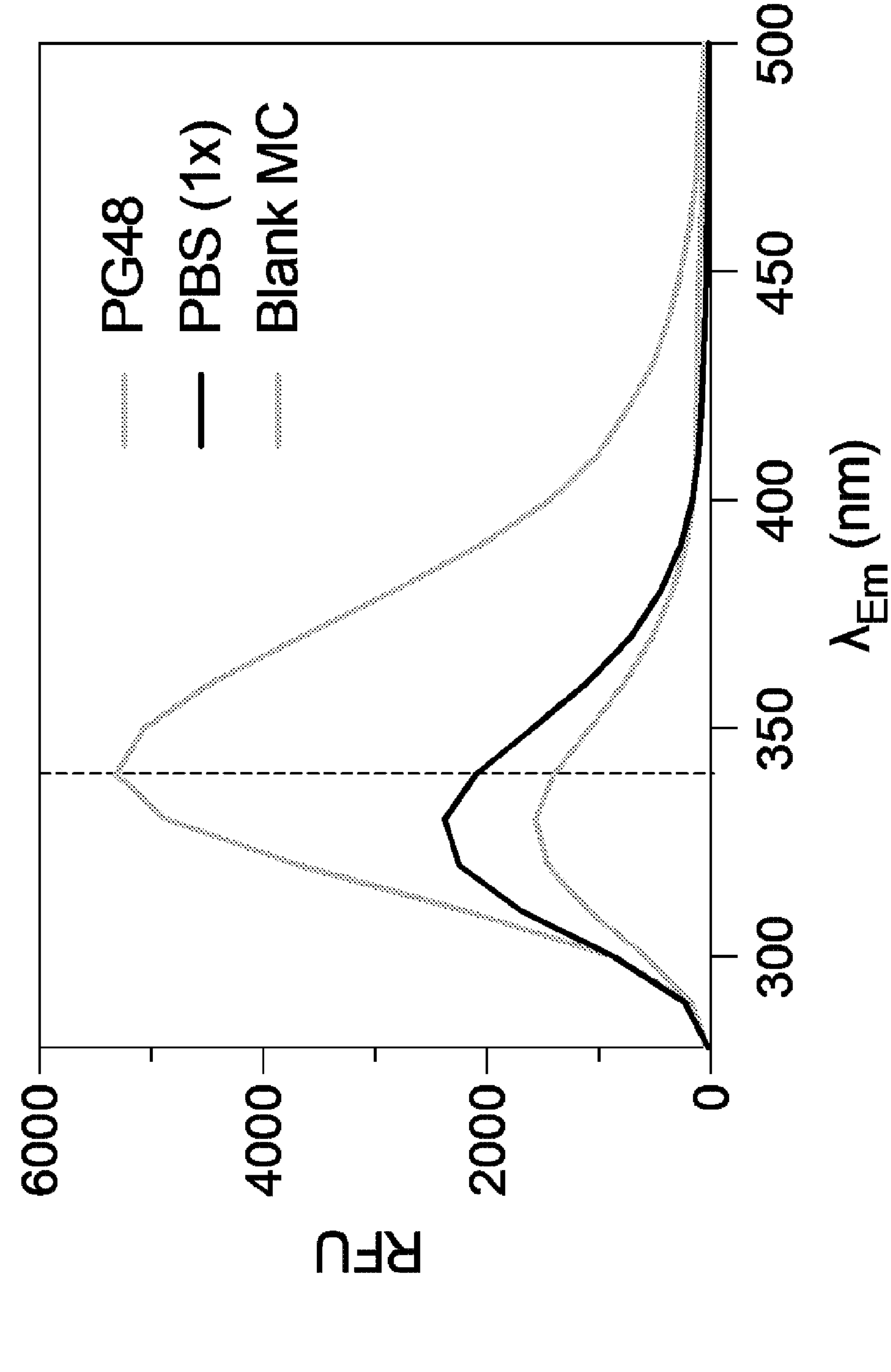
FIG. 16 shows a fluorescence emission scan of PEG-b-PPS micelles comprising FLT4-binding peptide and blank micelles. The relative fluorescence signal is displayed for PBS (1×) background, blank micelles (MC), and the PG48 peptide. Fixed excitation wavelength ($\lambda_{Ex}$)=270 nm. Emission scan: $\lambda_{Em}$=280-500 nm.
Figure 17:
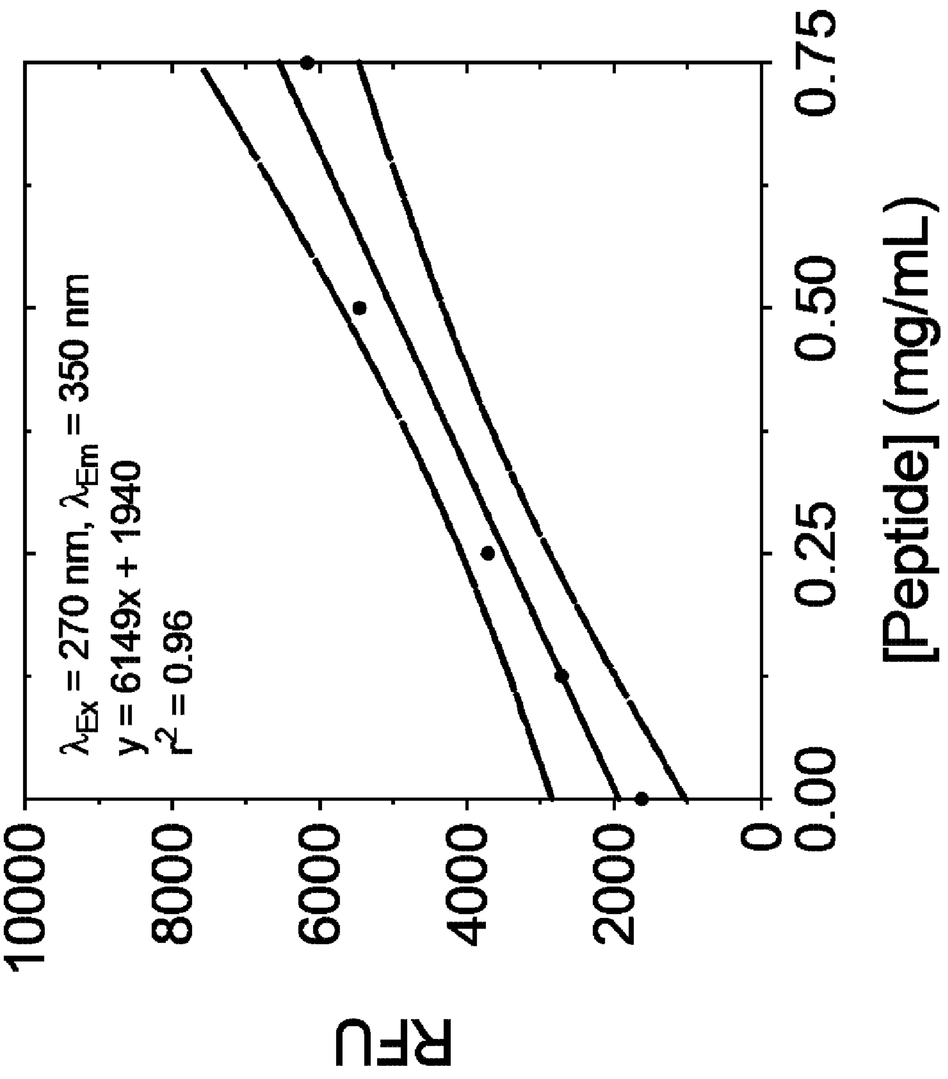
FIG. 17 shows a targeting peptide calibration. A representative calibration curve is displayed for a peptide concentration series (0, 0.125, 0.25, 0.50, and 0.75 mg/mL). Data was acquired at an excitation wavelength ($\lambda_{Ex}$) of 270 nm and an emission wavelength ($\lambda_{Em}$) of 350 nm. The mean±s.e.m. (n=3) is displayed with the 95% confidence bands. Where error bars are not displayed, the error is so small that the bars would not be visible. A linear regression model was fit to the data.

Peptides were embedded into $PEG_{45}$-b-$PPS_{23}$ MC nanocarriers at 1% or 5% molar ratios (peptide:polymer) and were purified through a lipophilic Sephadex column to remove any unembedded peptide. The resulting micelle formulations were monodisperse (PDI<0.1) with an average diameter of ~21-23 nm (Table 5). Electrophoretic light scattering (ELS) analysis demonstrate a zeta potential indicative of a neutrally charged surface for all nanocarriers in the presence and absence or peptide (Table 5). Peptide incorporation into micelles was verified by Fourier transform infrared spectroscopy (FTIR; FIG. 15) and peptide concentration was determined spectrophotometry (FIG. 16; FIG. 17). FTIR spectra of purified peptide-displaying micelle formulations revealed peaks in the amide I band (1700-1600 $cm^{-1}$; C═O and C—N stretching vibrations) and amide II band (1590-1520 $cm^{-1}$; N—H in-plane bending and C—N, C—C stretching vibrations) (FIG. 15). These peaks are characteristic of the peptide bond and were absent from micelles prepared without peptide (FIG. 15).

The incorporation of peptide did not disrupt the spherical morphology expected for PEG-b-PPS micelles, as demonstrated by morphological analysis using cryogenic transmission electron microscopy (Cryo-TEM; FIG. 10*f*) and small angle x-ray scattering (SAXS) performed using synchrotron radiation (FIG. 10*g-i*; Table 5). In Cryo-TEM micrographs, PEG-b-PPS micelles appear as small dark circles in two-dimensions. These visible structures are the high contrast PPS hydrophobic core of the self-assembled PEG-b-PPS micelles, rather than the low contrast micelle PEG corona. Consistent with this interpretation, the hydrodynamic size measured by DLS (Table 5) exceeds the diameter of the PPS core observed by Cryo-TEM. The exclusive presence of the PPS core structures, and their size similarity across different formulations, is consistent with the expected micelle morphology. These results further suggest nanocarrier morphology is not perturbed by the palmitoleic lipid anchor of the peptide.

Figure 18:
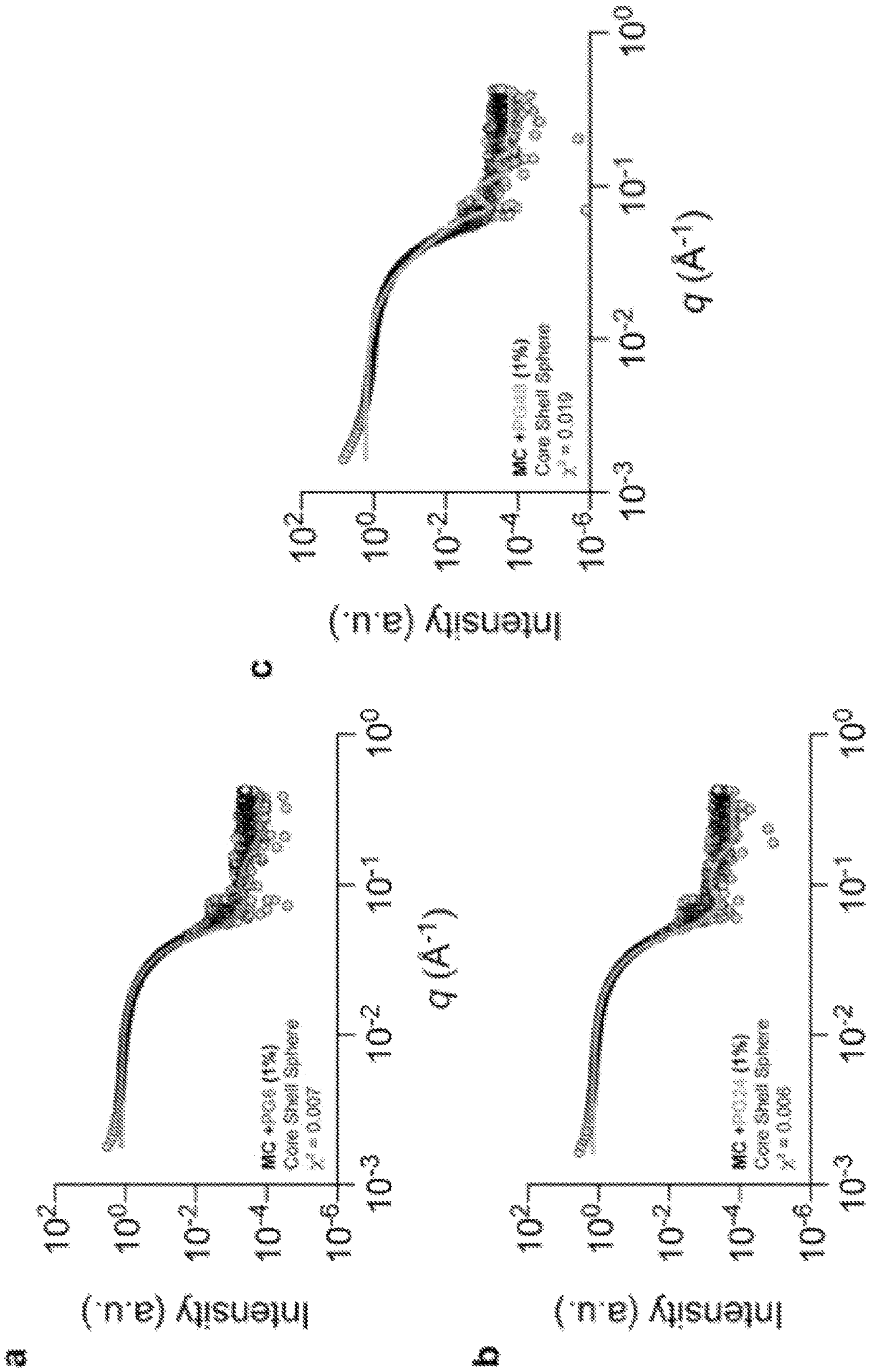
FIG. 18 shows small angle x-ray scattering (SAXS) data for PEG-b-PPS micelles displaying FLT4-binding peptides at a 1% molar ratio. Core shell sphere models were fit to SAXS data obtained for PEG-b-PPS MCs displaying (a) PG6, (b) PG24, or (c) PG48 at a 1% molar ratio (peptide: polymer). The chi square of each model fit is inset ($c^2<1.0$ indicates a good model fit). See Table 2 for more details regarding each model fit. SAXS was performed using synchrotron radiation at Argonne National Laboratory.

Micelle total diameter measurements obtained by SAXS was generally in agreement with the orthogonal analysis by DLS (Table 5). However, the higher resolution information obtained by probing the nanocarrier suspensions with high intensity x-rays did shed light on various structural details. Core shell models were fit to the data with high confidence, further supporting the micelle morphology was unperturbed by the presence of peptide at 1% (FIG. 18) or 5% (FIG. 10*g-i*) molar ratios. In all cases, the micelle core radius in the presence of peptide exceeded that of blank micelles by greater than 1 nm (Table 5). We attribute this observation to hydrophobic packing by the palmitoleic acid lipid anchor of the FLT4-binding peptides with the PPS core of the micelles.

TABLE 5

| Physicochemical characterization of PEG-b-PPS micelles displaying FLT4-targeting peptide constructs | | | | | | | |
|---|---|---|---|---|---|---|---|
| | | | SAXS†† | | | | ELS |
| | DLS† | | | | Shell | | Zeta |
| Formulation | $D_{Total}$ (nm) | PDI | $D_{Total}$ (nm) | $R_{Core}$ (nm) | thickness (nm) | $\square^2$ | Potential (mV)‡ |
| BL MC | 21.9 | 0.06 | 21.0 | 4.5 | 6.0 | 0.011 | −1.2 ± 0.2 |
| MC +PG6 (1%) | 21.8 | 0.05 | 21.2 | 6.3 | 4.3 | 0.007 | 1.7 ± 0.4 |
| MC +PG6 (5%) | 21.5 | 0.06 | 20.9 | 6.1 | 4.3 | 0.008 | 2.5 ± 0.1 |

TABLE 5-continued

Physicochemical characterization of PEG-b-PPS micelles displaying FLT4-targeting peptide constructs

| | DLS† | | SAXS†† | | | | ELS |
|---|---|---|---|---|---|---|---|
| Formulation | $D_{Total}$ (nm) | PDI | $D_{Total}$ (nm) | $R_{Core}$ (nm) | Shell thickness (nm) | $\square^2$ | Zeta Potential (mV)‡ |
| MC +PG24 (1%) | 20.4 | 0.07 | 21.2 | 6.1 | 4.5 | 0.006 | 0.6 ± 0.2 |
| MC +PG24 (5%) | 21.6 | 0.08 | 21.4 | 6.1 | 4.6 | 0.014 | 1.3 ± 0.7 |
| MC +PG48 (1%) | 20.7 | 0.06 | 23.0 | 6.3 | 5.2 | 0.019 | 0.4 ± 0.2 |
| MC +PG48 (5%) | 22.4 | 0.05 | 24.2 | 6.1 | 6.0 | 0.012 | 2.1 ± 0.7 |

†Number average hydrodynamic diameter ($D_{Total}$) and polydispersity index (PDI) measured by dynamic light scattering (DLS).
††Small angle x-ray scattering (SAXS) performed using synchrotron radiation at Argonne National Laboratory. The fit values for the total diameter ($D_{Total}$), thickness of the shell, and radius of the core ($R_{Core}$) are displayed together with the chi squared ($\square^2$) value for the final model fit.
‡Mean zeta potential ± s.d. (n = 3) measured by electrophoretic light scattering (ELS).

While the shell thickness of micelles displaying PG48 at 1% or 5% molar ratio is greater than that of micelles displaying PG6 or PG24 at equivalent molar density, the shell thickness of PG48 formulations matched that of the blank micelles (Table 5). We attribute this observation to the greater continuity of the PEG corona in micelles prepared without peptide (blank micelles) and those displaying PG48, which scatter x-rays more consistently. The PG6 and PG24 constructs have fewer hydrophilic units than the 45-unit PEG block (PEG45) of the polymer (this is depicted in the FIG. 10*f* illustrations). This length mismatch leaves a void volume that provides greater freedom for the $PEG_{45}$ distal end to compact, leading to less consistent scattering near the micelle surface and a lower apparent shell thickness in these formulations. This interpretation will be corroborated by proteolysis experiments in the proceeding section, which probe the differences in biochemical access of each targeting ligand type.

Evaluation of peptide biochemical accessibility and targeting Schlemm's canal cells in vitro. We hypothesized that targeting peptides designed with longer PEG spacers would minimize ligand obstruction by the micelle PEG corona to biomolecules in the surrounding environment, and that these accessibility enhancements would improve peptide binding with FLT4 receptors (FIG. 9). To examine differences in peptide accessibility, we developed a mass spectrometry-based proteolysis kinetic assay. This assay uses trypsin protease (23.3 kDa) as a biochemical probe (~5.8 nm diameter), which cleaves arginine (WHWLPNLRHYAS (SEQ ID NO: 1)) in the peptide sequence to induce mass shifts that are detectable in quenched reaction aliquots (FIG. 11*a*). A crude proteolysis rate is determined by monitoring the ratio of intact versus cleaved peptide signal intensities with time. Comparing differences in proteolysis kinetics provides a means to examine how accessible peptide constructs are to biomolecules in their environment when displayed on nanocarriers.

When presented on micelles in the PG48 form, the FLT4-binding peptide substrate was cleaved to completion almost immediately, whereas buried PG6 and PG24 constructs were cleaved at much slower rates (FIG. 11*b*). This result indicates protease access to the peptide component of the PG6 and PG24 constructs is obstructed by the 45-unit PEG corona of the MC nanocarriers to an extent that depends on the depth it is buried. The ligand obstruction observed for PG6 and PG24 constructs further suggests the potential for suboptimal engagement with FLT4/VEGFR3 receptors on the surface of the Schlemm's canal cells.

To examine whether these differences in ligand accessibility translate into greater interactions with the Schlemm's canal cells, we performed nanocarrier uptake studies with cultured Schlemm's canal cells from normal human donors (target cell type) and HUVECs (vascular endothelial cell model; off-target cell type) (FIG. 11*c*). Increasing peptide accessibility improved Schlemm's canal-targeting in vitro. Compared to all other formulations, MC +PG48 (5%) significantly enhanced micelle uptake by Schlemm's canal cells (FIG. 11*d*) and decreased off-target uptake by HUVECs (FIG. 11*e*). Micelles displaying the PG48 peptide resulted in a nearly 2-fold enhancement in Schlemm's canal-targeting specificity compared to the PG6 and PG24 constructs that are buried within the micelle PEG corona (FIG. 11*f*) and a 4.5-fold enhancement in Schlemm's canal cell uptake over HUVEC (FIG. 11*f*).

For micelles displaying the PG6 or PG24 constructs, the use of shorter PEG spacers together with the 12 amino acid FLT4-binding peptide obstructs biochemical access to the ligand (FIG. 11*b*) and the extent of this obstruction is a function of ligand display depth within the micelle PEG corona. Importantly, differences in ligand biochemically accessibility resulted in significant differences in Schlemm's canal cell targeting performance (FIG. 11*d-f*). The targeting performance of a nanocarrier measurably decreased with increasing ligand obstruction.

Performance evaluation of PG48 versus PG6 on enhancing the micellar delivery of IOP-reducing agents in vivo. As our goal was to develop nanocarriers capable of targeting Schlemm's canal cells and delivering payloads that lower IOP, we sought to determine if the optimized nanocarriers displaying the FLT4-binding peptide above the surface would outperform our original, buried peptide construct (PG6) in a more clinically relevant setting. We were particularly interested in evaluating the performance of the original PG6 construct[34] against the more highly-targeted PG48 construct in the delivery of the IOP-reducing agent latrunculin A (LatA) in vivo. LatA is a 16-membered macrolide[53] that acts by blocking the incorporation of actin monomers into actin filaments and thereby depolymerizing actin and lowering cell stiffness[34,45]. We executed a longitudinal assessment of IOP in C57BL/6J mice receiving LatA MC displaying either PG6 or PG48 in contralateral eyes. Aside from the introduction of the optimized targeting construct, this study incorporated a paired design and greater statistical power than our previous analysis[34].

Figure 20:
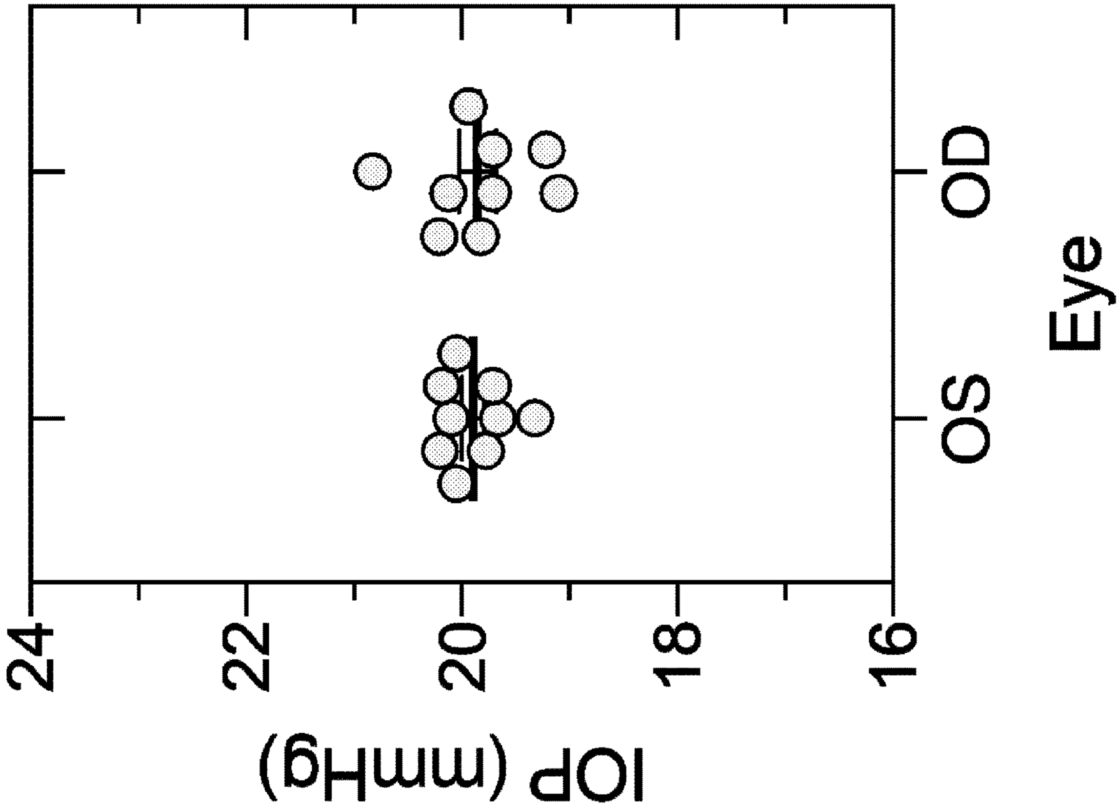
FIG. 20 shows a comparison of the baseline IOP measured in the left and right eyes of C57BL/6J mice. Significant differences in the IOP of the left (OS) and right (OD) eyes of the animals were determined at baseline using a paired t-test and a 5% significance level (n=9). Significant differences in baseline IOP were not found.

The baseline IOP was measured by tonometry prior to treatment. Significant differences were not found in the contralateral IOP measured at baseline (OS: 19.9±0.1 mmHg; OD: 19.9±0.2 mmHg; FIG. 20). Afterwards, LatA MC +PG48 and LatA MC +PG6 were administered intracamerally to contralateral eyes (i.e., one eye received one formulation type whereas the other eye received the second formulation type) (FIG. 12*a*). IOP was measured by tonometry at 24, 30, 48, 72, and 96 h following intracameral injection (FIG. 12*a*). Compared to baseline IOP values, both formulations led to a significant decrease in IOP at the 24 h timepoint, with an IOP reduction of −7.5±0.9 mmHg in the LatA MC +PG48 treatment group and −7.1±1.4 mmHg in the LatA MC +PG6 group (FIG. 12*b*). While the decrease in IOP in the PG48 group was greater at 24 h than the PG6 group, this difference was not statistically significant.

However, a notable divergence in the efficacy of the two competing formulations was observed after 24 h (FIG. 12*b*). LatA-loaded micelles displaying the PG48 peptide sustained a reduction in IOP through 72 h and did not return to baseline until day 4 post-treatment (FIG. 12*b*), in contrast to the PG6 treatment group, in which the IOP returned to baseline by 48 h (FIG. 12*b*). Our paired statistical analysis demonstrated that the IOP of eyes treated with LatA MC +PG48 (18.0±0.7 mmHg) was significantly lower than those treated with LatA MC +PG6 (20.3±0.9 mmHg) at 48 h (FIG. 12*b*). Furthermore, the IOP measured in eyes receiving LatA MC +PG48 was significantly lower than baseline values through 48 h (i.e., at 24, 30, and 48 h) (FIG. 12*b*). For eyes receiving LatA MC +PG6, significant differences from baseline IOP were only observed through 30 h (FIG. 12*b*).

From these results, we conclude the targeting performance of micelles displaying the PG48 FLT4-binding peptide is superior to that of micelles displaying the PG6 variant. This improved ability to target cell softening agent delivery to the Schlemm's canal endothelium enhanced efficacy by achieving a prolonged reduction in IOP that was statistically significant through 48 h after a single injection.

Figure 12:
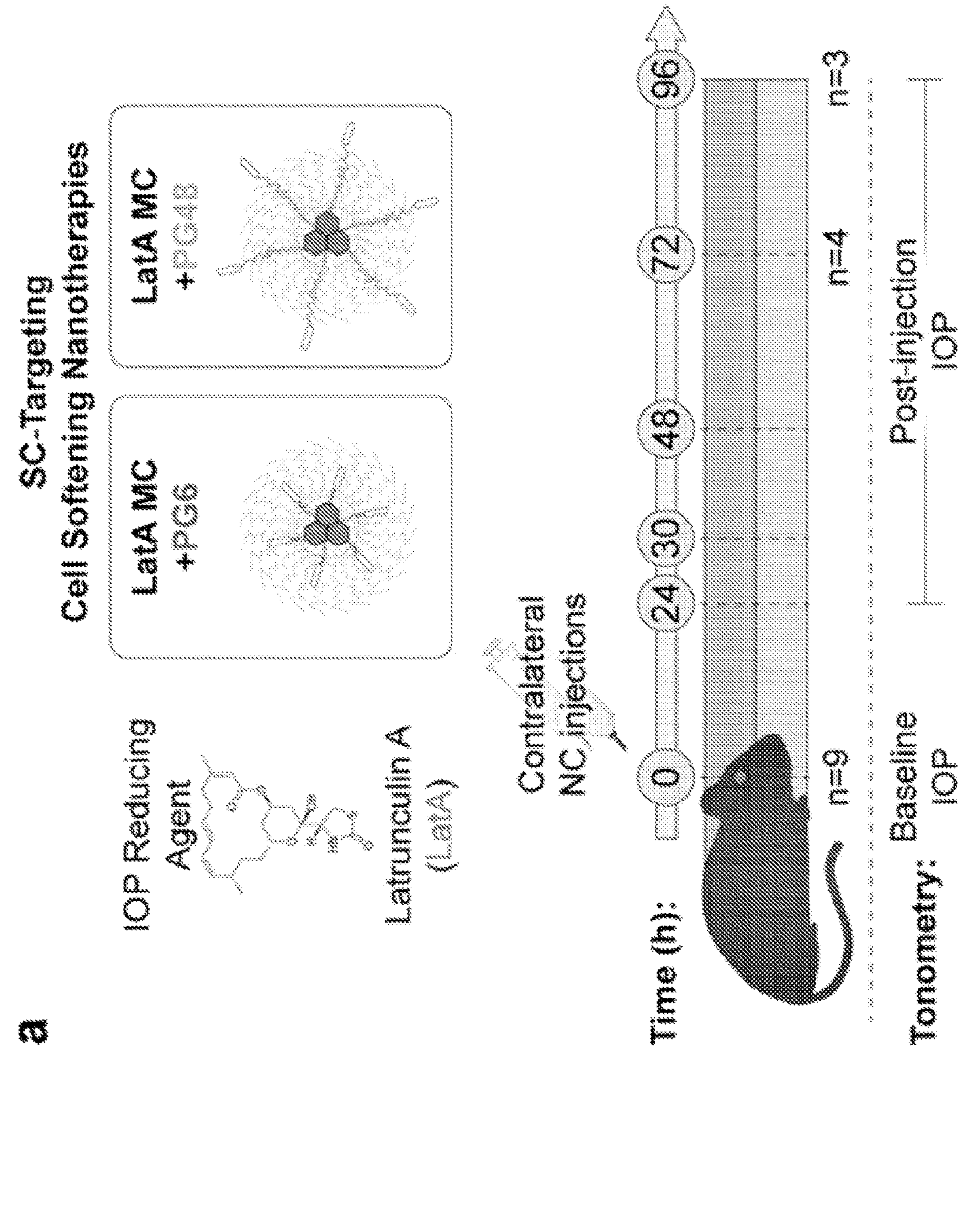
FIG. 12 demonstrates that increasing the biochemical accessibility of the FLT4-targeting peptide on SC-targeting nanocarriers enhances efficacy of a model IOP-reducing agent in vivo. (a) Experimental overview. The performance of latrunculin A-loaded micelles (18 μM latrunculin A) displaying either the PG6 or PG48 FLT4-binding peptide was evaluated in vivo in a paired IOP study. Nanocarriers were injected intracamerally into the contralateral eyes of mice. IOP was measured prior to injection (baseline), and at 24, 30, 48, 72, and 96 h after injection. Nine mice (n=9) were evaluated through 48 h. Measurements from four (n=4) and three (n=3) mice were obtained at 72 h and 96 h timepoints, respectively. (b) IOP time course at baseline and after intracameral injection of the specified nanocarrier formulations. Statistically significant differences between the PG6 and PG48 treatment groups were determined using a paired, two-tailed t-test and a 5% significance level. ‡‡p<0.01. The bars above the plot show statistically significant differences in IOP from the baseline value within the specified treatment group, assessed using a paired, two-tailed t-test. **p<0.0001; *p≤0.001; **p<0.005; *p<0.05.
Figure 12:
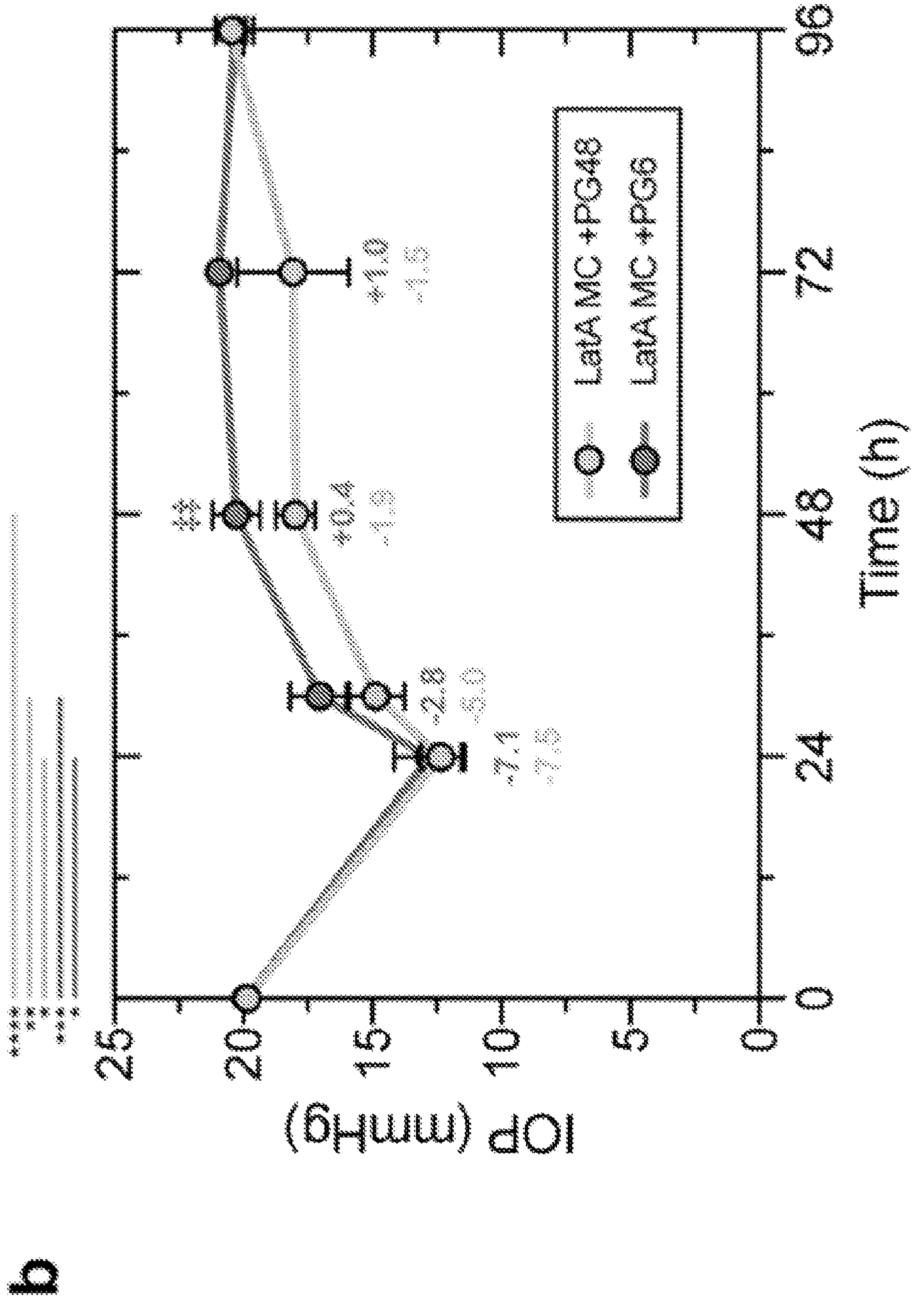
Figure 13:
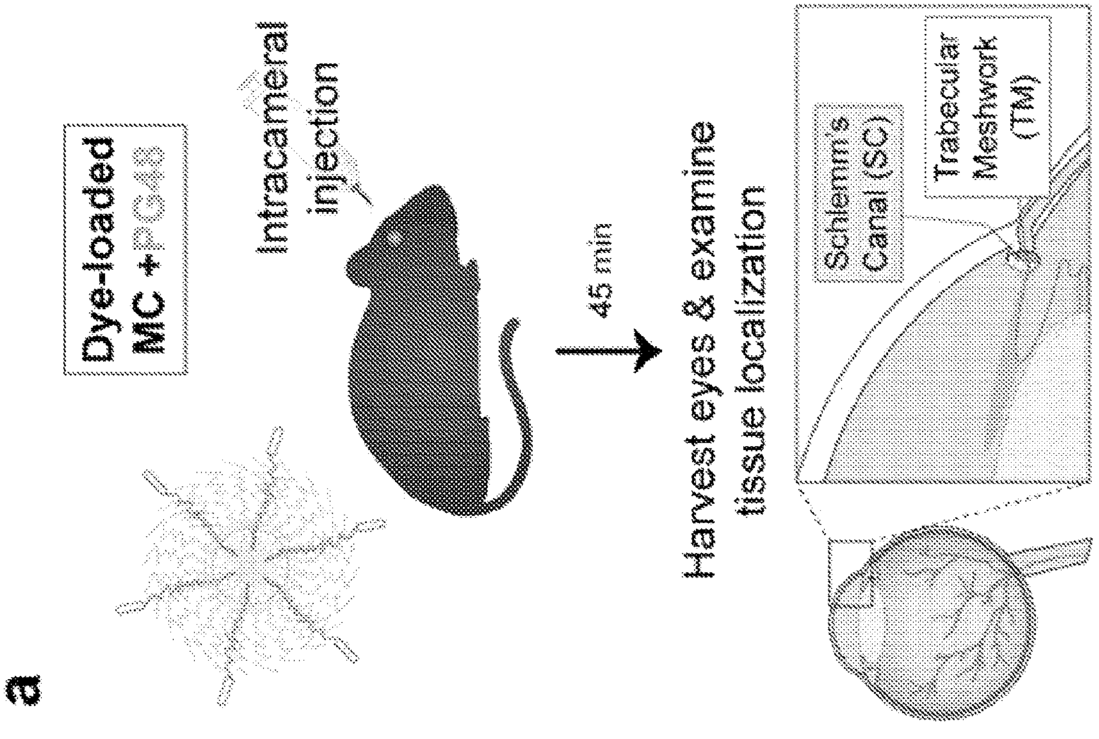
FIG. 13 shows confocal microscopy of MC +PG48 localization within the murine conventional outflow pathway in vivo. (a) Experimental illustration. DiI dye-loaded MC +PG48 (5%) nanocarriers (20 mg/mL polymer concentration) were administered intracamerally in C57BL/6J mice. After 45 min, eyes were enucleated and fixed for confocal microscopy analysis. (b, c) Images of conventional outflow pathway tissues obtained from eyes of (b) the negative control group (no injection) and (c) the MC +PG48 treatment group. Images were acquired at 20× magnification. DAPI and DiI signals are overlaid to present the cell nuclei and nanocarrier localization, respectively. Scale bar=50 μm. Tissue abbreviations: SC: Schlemm's canal; TM: Trabecular meshwork.
Figure 13:
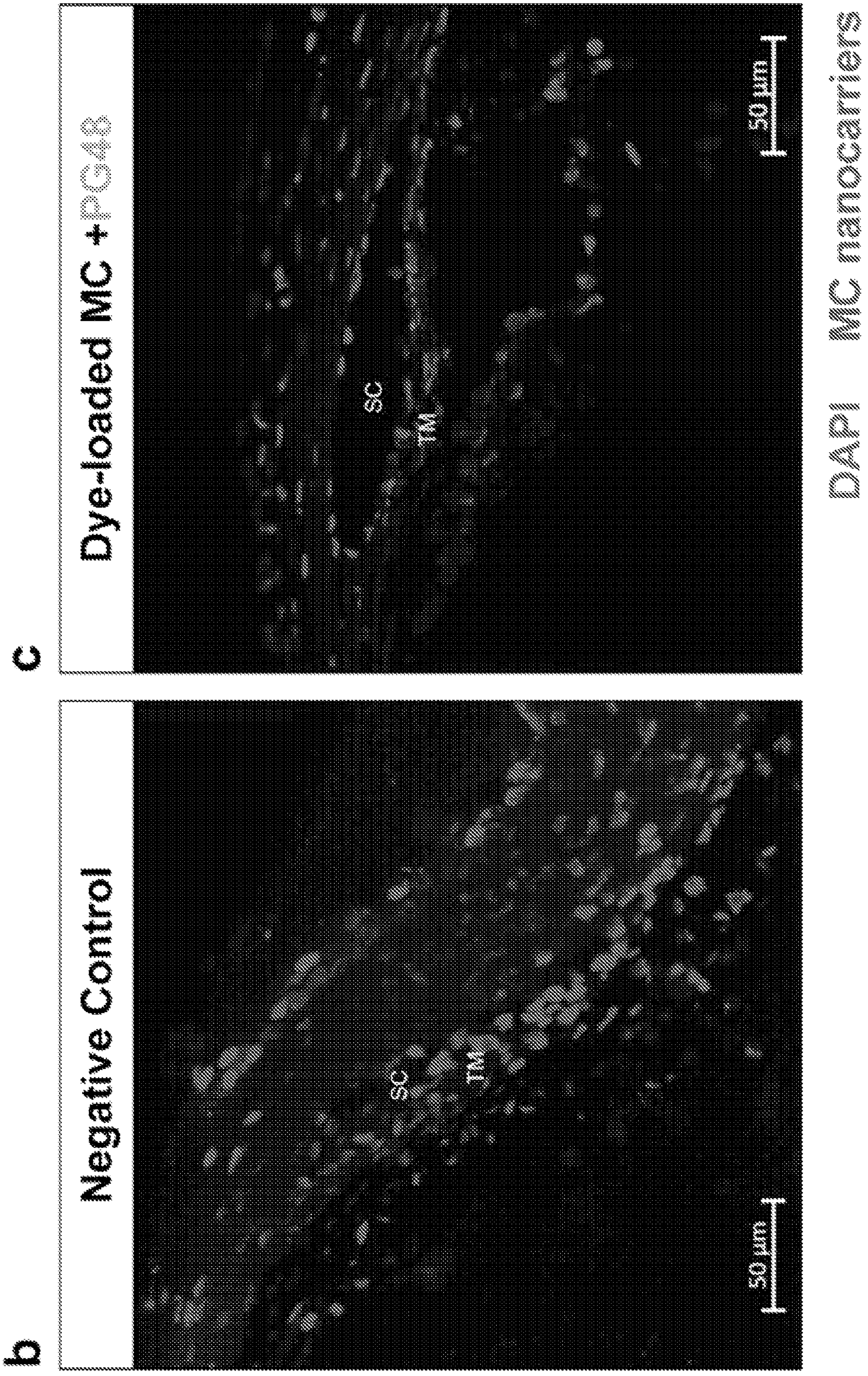

Localization of the optimal SC-targeting nanocarriers in the murine conventional outflow pathway. We next examined the localization of micelles displaying the PG48 peptide within the murine conventional outflow pathway (FIG. 13*a*). We were particularly interested in the localization of PG48-displaying micelles at an early timepoint that would precede its observed effects in our longitudinal IOP assessment (FIG. 12). To this end, PG48-displaying micelles were prepared to load a lipophilic dye to permit fluorescence tracing in conventional outflow tissues. Nanocarriers were administered intracamerally into C57BL/6J mice and eyes were enucleated at 45 minutes post-injection for confocal microscopy. A previous study[54] using carboxylate-modified fluorescent tracers demonstrated that a post-injection duration of 45 min is sufficient to allow 20 nm spherical vehicles to migrate through the conventional outflow pathway tissues and reach the trabecular meshwork and Schlemm's canal[54]. Thus, the 45 min timepoint was used in the present studies to examine whether the targeted PEG-b-PPS nanocarriers are detectable at the target site (Schlemm's canal) shortly after entering the conventional outflow pathway.

We examined tissue sections prepared from the anterior segments of the negative control and nanocarrier-receiving eyes (FIG. 13*b,c*). The PG48-displaying micelles were distributed non-uniformly circumferentially around the eye (data not shown). These SC-targeting nanocarriers accumulated at the inner wall of Schlemm's canal and the neighboring juxtacanalicular tissue (JCT) of the trabecular meshwork (TM) (FIG. 13*c*). Interestingly, the fluorescent signal that localized to the SC was much greater than the TM-localizing signal (FIG. 13*c*). We further note that at this timepoint (45 min post-injection), the nanocarriers were also observed to a lesser extent along the endothelial side of cornea but were blocked by the endothelial barrier. From this analysis, we conclude that the SC-targeting micelles accumulate at the SC endothelium at higher concentrations than in the nearby trabecular meshwork. The relatively strong localization to the SC in the anterior chamber further suggests that the FLT4-binding strategy achieves high specificity for the tissue of interest.

Discussion

Glaucoma is a progressive disease that, if untreated, slowly but relentlessly destroys ganglion cells and robs vision. The lowering of IOP is the only treatment for glaucoma that is proven to decrease disease progression. Agents such as actin depolymerizers and Rho kinase inhibitors reduce cell stiffness and have been shown to lower the IOP when delivered to the aqueous humor outflow pathway. However, these agents have significant side effects that are associated with off-target vasodilation of ocular surface vessels. Using optimized nanocarriers loaded with an actin depolymerizing agent, LatA, we demonstrate here that we can target Schlemm's canal cells in a highly specific fashion using versatile nanocarriers and that these nanocarriers when loaded with a cell softening agent significantly lower IOP in murine eyes for an extended period of time.

As the goal was to develop a nanocarrier that selectively targeted Schlemm's canal cells, it was necessary to demonstrate that the target, FLT4, is expressed at high levels not only on normal, but also glaucomatous Schlemm's canal cells (FIG. 9). This indicated that promoting nanocarrier engagement with these receptors may provide a clinically useful approach to direct the delivery of cell softening agents to the Schlemm's canal cells. These data also suggested that the disease state does not hinder the expression of FLT4 by Schlemm's canal cells.

The overarching goal of the present work was to develop an improved nanotechnology platform for targeting the delivery of cell softening agents to the Schlemm's canal endothelium in order to lower IOP. Previous studies of LatA demonstrated promise in reducing the IOP[25,26] but did not lead to the development of a clinical product. Our previous biomechanical analyses using atomic force microscopy (AFM) demonstrated that untargeted micellar delivery of LatA softens Schlemm's canal cells in vitro[45], thereby confirming the successful lysosomal escape of an actin depolymerizing agent following cellular internalization and validated PEG-b-PPS nanocarriers as appropriate vehicles for delivering cell softening agents. In a separate set of studies we demonstrated that the targeted micellar delivery of LatA (LatA MC +PG6) at a low concentration of 50 nM is sufficient to significantly reduce Schlemm's canal cell stiffness compared to control in vitro[34], and the targeted micellar delivery of 15.5-17 μM LatA using PG6 led to significant reductions in murine IOP for up to 24 h in vivo following intracameral injection[34].

To improve the efficacy of cell softening agents delivered by Schlemm's canal-targeting micelles, we rationally designed variants of our modular lipid-anchored FLT4-binding peptide to achieve a greater influx of drug-loaded nanocarriers into the Schlemm's canal cells. We began this design process with the observation that our original Schlemm's canal-targeting construct[34], denoted in the present work as "PG6", was likely buried beneath the micelle surface where it is less accessible to FLT4 receptors. This design consideration is fairly unique to lipid-anchored targeting peptides embedded in amphiphilic nanocarriers, since materials are more commonly prepared for targeting via the direct conjugation of ligand to the surface[55]—a strategy that can encounter issues with a lack of modularity, usage of harsh chemical conditions, control over display density, among others[56,57].

Understanding the relationship between the biochemical access of a lipid-anchored ligand and targeting performance became a focus of the present work, since the use of targeting moieties to direct vehicles to the intended location requires (i) successful ligand docking with the cognate receptor, which is enabled by the specific arrangement of functional groups of the ligand with those of the receptor binding pocket, but also (ii) a lack of obstruction that hinders formation of the ligand-receptor complex. The latter consideration permits successful binding events to occur with a greater frequency. Whereas the first requirement is fulfilled by the WHWLPNLRHYAS (SEQ ID NO: 1) peptide that was developed by phage display to specifically bind FLT4 receptors, the second requirement was not fully met, since the use of the six-unit PEG spacer left the lipid-anchored peptide shrouded within the 45-unit PEG corona of the micelles self-assembling from $PEG_{45}$-b-$PPS_{19}$ polymer.

Figure 10:
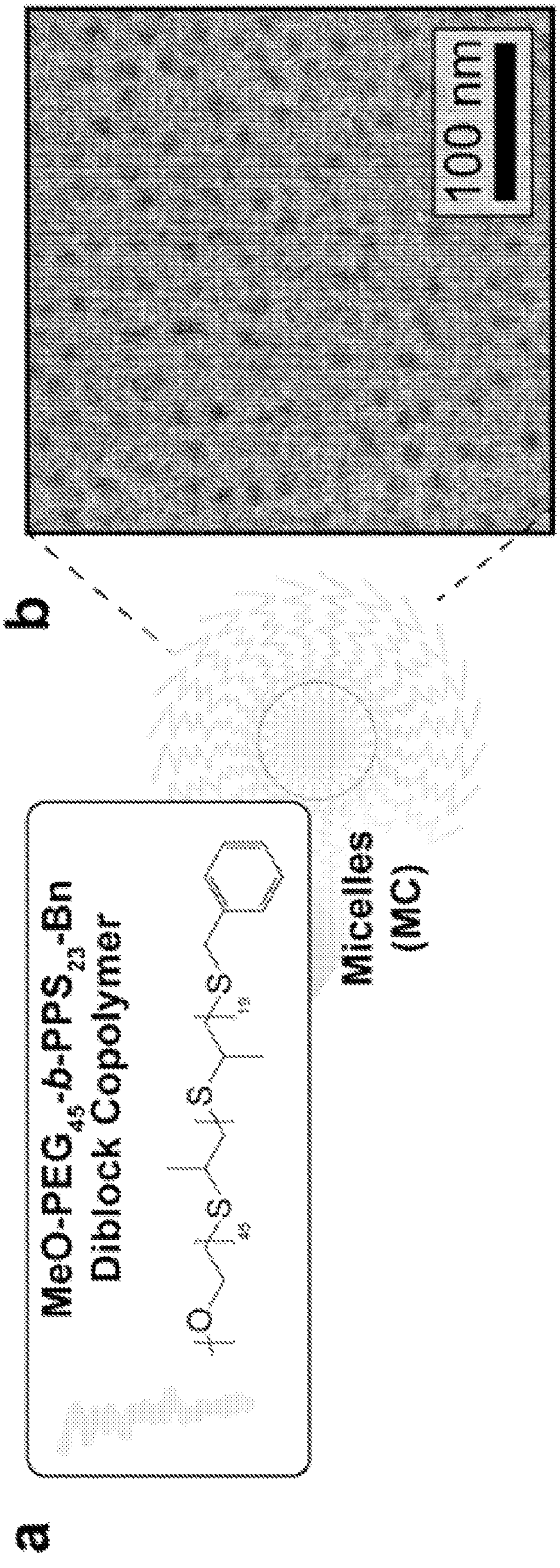
FIG. 10 shows a characterization of PEG-b-PPS micelles displaying lipid-anchored FLT4/VEGFR3-binding peptides that differ in the length of their PEG spacers. (a) Illustration of PEG-b-PPS micelles. (b) Cryo-TEM of blank micelles (i.e., micelles without peptide). (c) Micelle characterization by small angle x-ray scattering (SAXS). (d) Illustration of the designed FLT4-binding peptide constructs and LC-MS performed on the synthesized peptide products. (e) Deconvoluted mass spectra of purified peptides. Peaks are 2151.1, 3046.7, and 4071.4 Da for PG6, PG24, and PG48, respectively. (f) Cryo-TEM of MCs displaying the specified targeting peptides at 5% molar ratio (peptide:polymer). (g-i) Characterization of micelles displaying FLT4-binding peptides at a 5% molar ratio: (g) PG6, (h) PG24, and (i) PG48. The magnification is 10,000× and the scale bar is 100 nm for all Cryo-TEM micrographs. In all cases, small angle x-ray scattering (SAXS) was performed using synchrotron radiation at Argonne National Laboratory and a core shell model was fit to the data. The $\chi^2$<<1.0 was obtained for all model fits (a good fit is indicated by $\chi^2$<1.0).
Figure 10:
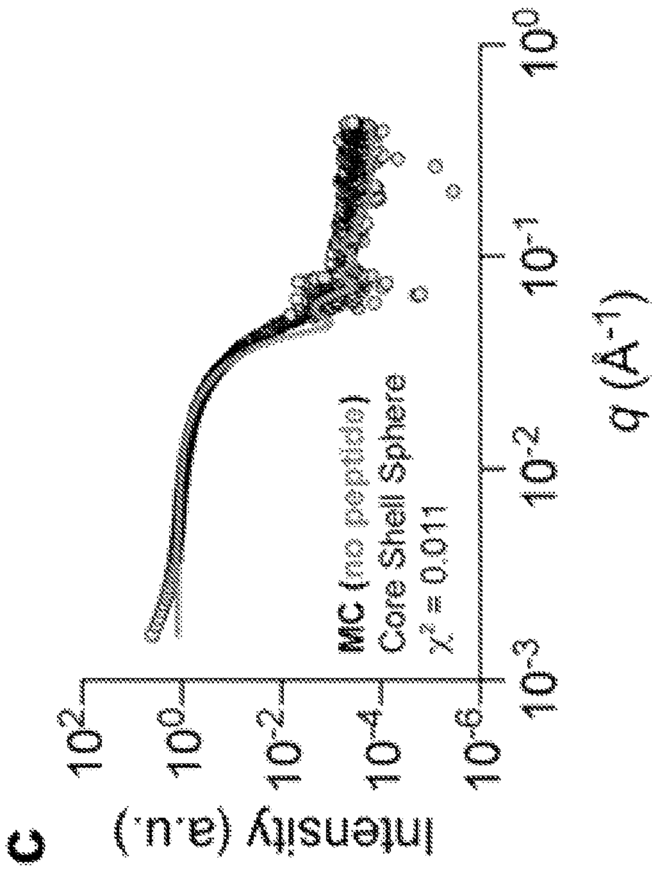
Figure 10:
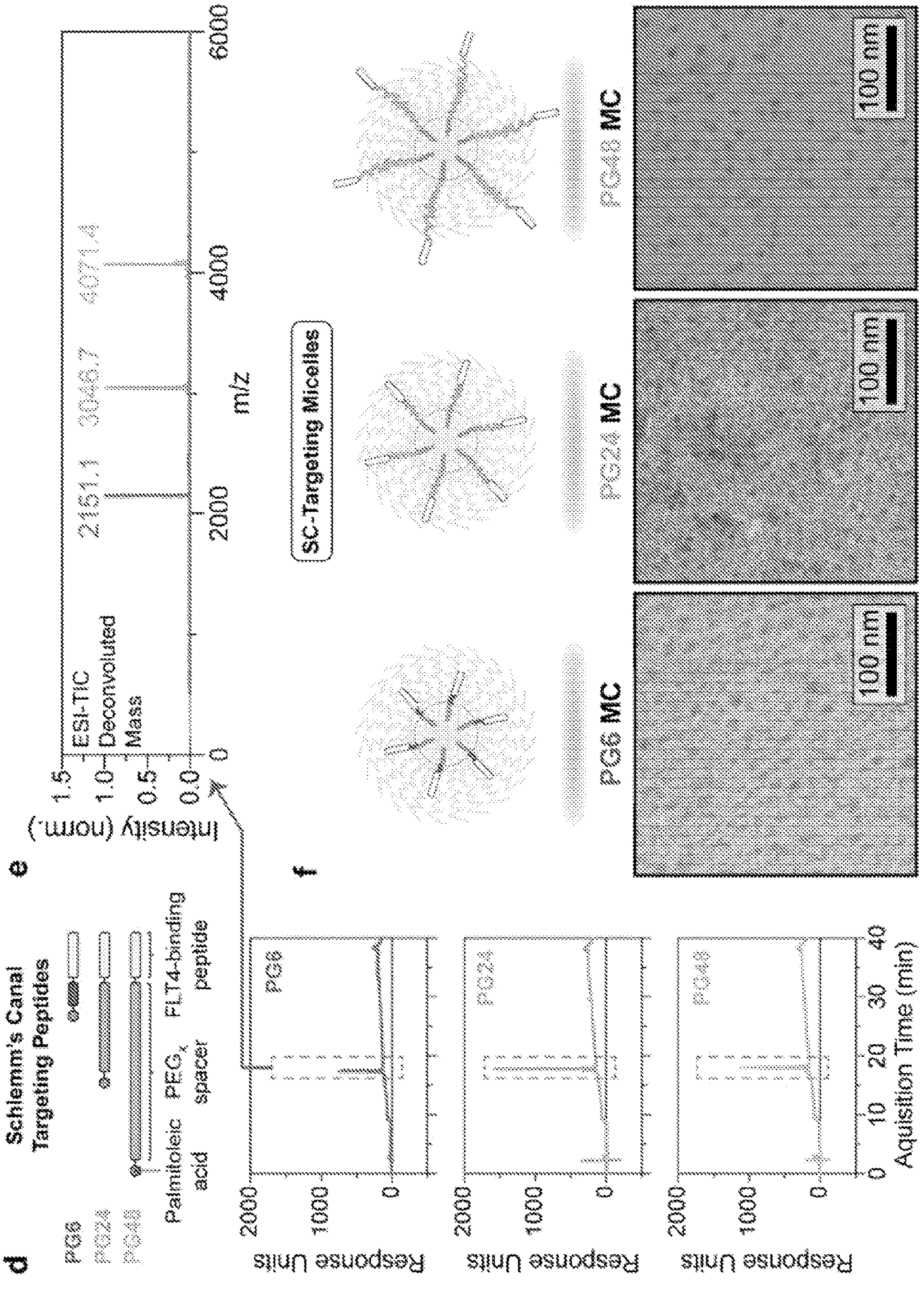
Figure 10:
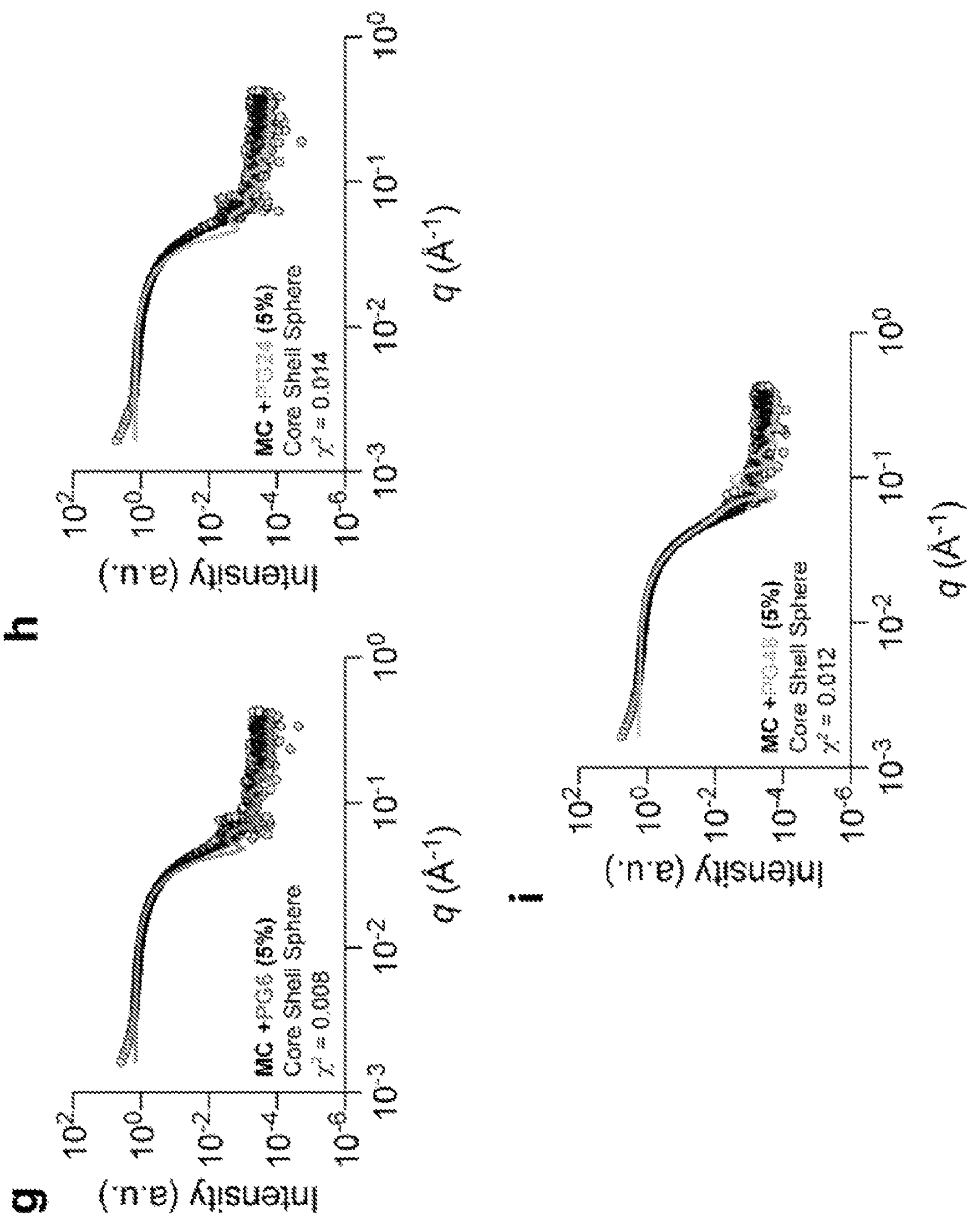

These considerations prompted our rational design of optimized targeting peptide constructs that differed in their PEG linker lengths and display depth on micelles (FIG. 10). As a pre-requisite for understanding the influence of these steric differences on targeting performance, we required an assay that is capable of probing peptide accessibility at the nanoscale. We sought to develop an assay that is high-throughput compatible and avoids the use of receptor proteins, which are notoriously difficult to purify in their native/active form and are expensive when commercially available. We reasoned the accessibility of nanocarrier-displayed peptide to its cognate receptor would correlate with its susceptibility to proteolysis in vitro. Despite being very different in nature, receptor binding and protease-mediated cleavage both require physical access to the peptide ligand to initiate a successful interaction. It seemed plausible to quantify peptide accessibility by monitoring the occurrence of a peptide-modifying event with time. If the steric differences influenced peptide access, the frequency of a peptide-modifying event should decrease with greater obstruction by the micelle PEG corona.

These considerations inspired our development of a novel method that uses trypsin as a biochemical probe. Trypsin acts on each peptide molecule only once, since the peptide contains one arginine residue and lysine is absent. Cleavage of the peptide by trypsin produces irreversible mass shifts, and the proteolysis kinetics are monitored to quantify differences in the accessibility of lipid-anchored targeting peptides displayed on amphiphilic nanocarriers (FIG. 11*a*). In this assay, we hypothesized that PG48 is displayed at the micelle surface where it is most susceptible to proteolysis, thereby yielding peptide cleavage at a greater rate than the PG24 or PG6 peptides. PG24 and PG6 incorporate shorter PEG linkers (FIG. 10), leaving these constructs buried to different extents within the outer PEG corona micelles that self-assemble from $PEG_{45}$-b-$PPS_{19}$.

In agreement with our hypothesis, the protease protection kinetic assay developed herein demonstrated that the use of 6-, 24-, or 48-unit PEG spacers achieves significant differences in biomolecular access to the peptide ligand (FIG. 11*a,b*). These molecular-level differences in ligand access translated to differences in targeting specificity in vitro in studies conducted with primary cultures of Schlemm's canal cells obtained from human donors (FIG. 11*c-f*). Micelles displaying the most accessible targeting peptide, PG48, achieved the greatest targeting specificity for Schlemm's canal cells in these studies (FIG. 11*f*). This specificity improvement resulted in both an increase in uptake by the Schlemm's canal cells (FIG. 11*d*) and a decrease in uptake by vascular endothelial cells, a model of cells where uptake is not desirable[23] (FIG. 11*e*).

Our paired longitudinal IOP studies demonstrated that LatA-loaded micelles displaying the biochemically enhanced PG48 construct led to a 7.5 mmHg reduction in IOP, on average, after 24 h compared to 7.1 mmHg achieved by treatment with the LatA MC +PG6 formulation (FIG. 12*b*). While this change in IOP was not significantly different between the two groups at 24 h, the greater magnitude decrease observed after treatment with LatA MC +PG48 is consistent with a greater amount of drug reaching Schlemm's canal endothelium in vivo. Strikingly, mice receiving the optimized drug delivery vehicle maintained IOP reductions of −5.0, −1.9, and −1.5 mmHg at 30 h, 48 h, and 72 h, respectively, with the return to baseline observed at 96 h post-administration (FIG. 12*b*). The IOP reductions at 24 h, 30 h, and 48 h differed significantly from baseline levels for the PG48 group. In contrast, contralateral eyes receiving LatA MC +PG6 returned to baseline by 48 h after achieving a significant decrease in IOP at 24 h and 30 h (FIG. 12*b*)—an outcome that is consistent with the transient IOP decrease observed in our past reports from two separate trials with this construct[34]. Importantly, the IOP reduction in the PG48 group was significantly greater in magnitude than the PG6 group at the 48 h timepoint (FIG. 12*b*). Collectively, these results demonstrate the superiority of the PG48 construct for targeting the micellar delivery of a cell softening glaucoma therapeutic to Schlemm's canal in the eye. Analysis by confocal microscopy demonstrated that micelles displaying the PG48 FLT4-binding peptide accumulate within Schlemm's canal in vivo (FIG. 13*c*).

Enhancing the biochemical access to the FLT4 binding peptide leads to a greater accumulation of cell softening agents within the Schlemm's canal endothelium. Higher drug concentrations at the target site resulted in longer lasting improvements in outflow facility to yield an IOP reduction that is sustained for a longer period of time. We further conclude that micelles displaying the PG48 construct are the highest performing nanocarrier chassis for delivering IOP-lowering cell softening agents to Schlemm's canal. PEG-b-PPS micelles efficiently load diverse hydrophobic small molecules[44,58] and will accommodate a wide variety of new and currently available therapeutics[59].

Looking ahead, there remains the practical challenges of how the therapeutic effect of softening Schlemm's canal cells can be sustained for a longer period of time. As the corneal endothelium is permeable only to molecules with molecular weights less than approximately 500 Da[60,61], nanoparticles cannot be delivered to the anterior segment topically. Instead, these agents need to be either (i) injected to the anterior segment or retro-injected into the aqueous veins[62], or (ii) released continuously from a long-term depot/device placed in the eye. While injection is plausible for targeted-nanocarriers carrying gene therapy to Schlemm's canal, long term release is required for pharmacological treatments such as LatA carrying micelles as frequent intraocular injections would not be tolerated.

Aside from the more conventional delivery of pharmacological payloads, our Schlemm's canal targeting strategy can be extended to the development of gene delivery technologies[63]. Glaucoma is an attractive target for gene therapy[64,65] and modulating the expression of genes that regulate the stiffness of Schlemm's canal endothelial cells may hold the key to producing more permanent enhancements in outflow facility without stents or surgery. The lipid-anchored FLT4-binding peptides are modular, and readily incorporate into alternative PEG-b-PPS morphologies, such as vesicular polymersomes[48,56,58,66,67] or bicontinuous nanospheres[68-70], which are capable of encapsulating the hydrophilic cargoes necessary for genetic intervention. This includes regulatory RNAs for the transient modulation of gene expression, or CRISPR/Cas9 components for stable genome editing.

Conclusions

In closing, we demonstrate that steric effects between surface-displayed ligands and PEG coronas significantly impact targeting performance across multiple biological scales. Our work holds general implications for the rational design of receptor-targeted nanocarriers and also addresses challenges that are unique to the display of modular ligands anchored to vehicles bearing a common hydrophilic corona (here, PEG2k). We further demonstrate that the assessment of differential proteolysis kinetics provides a powerful tool for quantifying the relative biochemical access of targeting ligand prototypes displayed on nanocarrier surfaces. The biochemical access of a targeting ligand is an engineerable property that can be leveraged to control nanocarrier engagement with receptors on the target cell type over a continuous domain. When applied to the development of glaucoma nanotherapies using our FLT4-targeting approach, improving the biochemical access of peptide ligands increased drug delivery to Schlemm's canal endothelial cells while minimizing off-target interactions with vascular endothelial cells. These performance improvements at the molecular and cellular levels translated to efficacy enhancements in a paired, longitudinal IOP study in vivo, thereby demonstrating the potential utility of our methods in clinically relevant settings. The technologies developed herein show promise for improving the potency and specificity of cell softening agents used to manage ocular hypertension. More generally, our rational design principles and methodology can be extended to the development of other targeted nanotherapies to solve diverse challenges in drug delivery.

Materials and Methods

Chemicals. Unless otherwise stated, all chemical reagents were purchased from the Sigma Aldrich Chemical Company.

Solid phase peptide synthesis. Fmoc-N-amido-dPEG$_6$-acid, Fmoc-N-amido-dPEG$_{24}$-acid, and Fmoc-N-amido-dPEG$_{24}$-amido-dPEG$_{24}$-acid (Quanta Biodesign) were purchased for use in the synthesis of the PG6, PG24, and PG48 peptide constructs. Standard Fmoc solid phase peptide synthesis was performed to synthesize PG6, PG24, and PG24×2 (PG48) peptides on a 0.125 mmol scale. Information regarding each synthesized peptide is presented in Table 4. The chemical structure of each peptide is presented in FIG. 14.

Preparation of PEG-b-PPS micelle formulations. PEG$_{45}$-b-PPS$_{23}$ polymer was synthesized using established procedures[43,44] (Table 3). Briefly, sodium methoxide was used to deprotect PEG thioacetate. This deprotected PEG thioacetate is then used to initiate the polymerization of propylene sulfide through an anionic ring opening polymerization reaction. MC nanocarriers were self-assembled from PEG$_{45}$-b-PPS$_{23}$ polymer[43,44] via cosolvent evaporation using established protocols[45]. For uptake studies in vitro, MCs were prepared to load DiI hydrophobic dye (Invitrogen), whereas formulations intended for IOP studies in vivo were prepared to co-load latrunculin A (LatA; Cayman Chemical Company) and DiI. The formed MCs were split into aliquots of equal volume prior to the addition of peptide. PG6, PG24, or PG48 targeting peptides were dissolved in DMSO and were added to the specified MC aliquots at either a 1% or 5% molar ratio (peptide:polymer). Blank MC controls (lacking peptide) were included in cellular uptake studies. All formulations were prepared under sterile conditions and were filtered using a Sephadex LH-20 column.

Determination of peptide concentration. Peptide concentration in purified MCs was determined by measuring tryptophan fluorescence ($\lambda_{Ex}$=270 nm, $\lambda_{Em}$=350 nm), calibrated against a peptide concentration series, using a SpectraMax M3 microplate reader (Molecular Devices, LLC). The peptide is readily detectable using these parameters (FIG. 16). The concentration of peptide was determined using a simple linear regression model that was obtained by fitting the calibration data (see FIG. 17 for a representative calibration curve). To account for background fluorescence from the polymeric micelles, the emission from a blank micelle control formulation (lacking peptide) was subtracted from the peptide-containing micelle formulations. The peptide-containing formulations and control formulations were prepared in the same solvent and contained PEG-b-PPS polymer at identical concentration. This procedure isolates the analyte signal (the specified peptide) by removing contributions from PEG-b-PPS polymer and solvent.

Small angle x-ray scattering (SAXS). SAXS was performed using synchrotron radiation at the DuPont-Northwestern-Dow Collaborative Access Team (DND-CAT) beamline at the Advanced Photon Source at Argonne National Laboratory (Argonne, IL, USA). A 7.5 m sample-to-detector distance, 10 keV (λ=1.24 Å) collimated x-rays, and 3 second exposure time was used in all SAXS experiments. The q-range of 0.001-0.5 $Å^{-1}$ was used to analyze scattering, and silver behenate diffraction patterns were used for calibration. The momentum transfer vector (q) is defined in Equation 1, θ denotes the scattering angle:

$$q = 4\pi\frac{\sin(\theta)}{\lambda} \tag{1}$$

PRIMUS software (version 3.0.3) was used for data reduction. SasView (version 5.0) software was used for model fitting. A core shell sphere model (Equation 2) was fit to the scattering profiles of blank micelles (prepared without peptide), as well as micelles displaying PG6, PG24, or PG48 peptides at 1% or 5% molar ratios (peptide:polymer):

$$F(q) = \frac{3}{V_s}\left[V_c(\rho_c-\rho_s)\frac{\sin(qr_c)-qr_c\cos(qr_c)}{(qr_c)^3} + V_s(\rho_s-\rho_{solv})\frac{\sin(qr_s)-qr_s\cos(qr_s)}{(qr_s)^3}\right] \tag{2}$$

Where F is the structure factor, q is the momentum transfer vector (Equation 1), $V_s$ is the particle volume ($Å^3$), $V_c$ is the particle core volume ($Å^3$), $\rho_c$ is the core scattering length density ($10^{-6}$ $Å^{-2}$), $\rho_s$ is the shell scattering length density ($10^{-6}$ $Å^{-2}$), $\rho_{solv}$ is the solvent scattering length density ($10^{-6}$ $Å^{-2}$), $r_c$ is the core radius (Å). The radius of the total particle ($r_s$; units: Å) is used to determine the shell thickness ($r_t$; units: Å), as described by Equation 3:

$$r_s = r_c + r_t \tag{3}$$

Micelle diameter values determined from DLS (Table 5) were used to select initial values for the core radius and shell thickness prior to parameter fitting. An iterative chi square ($\chi^2$) minimization procedure using the Levenberg-Marquardt algorithm was used to fit optimal model parameters. A good core shell model fit is indicated by $\chi^2$<1.0. In all cases, $\chi^2$<<0.1 was obtained for final fit models.

Figure 19:
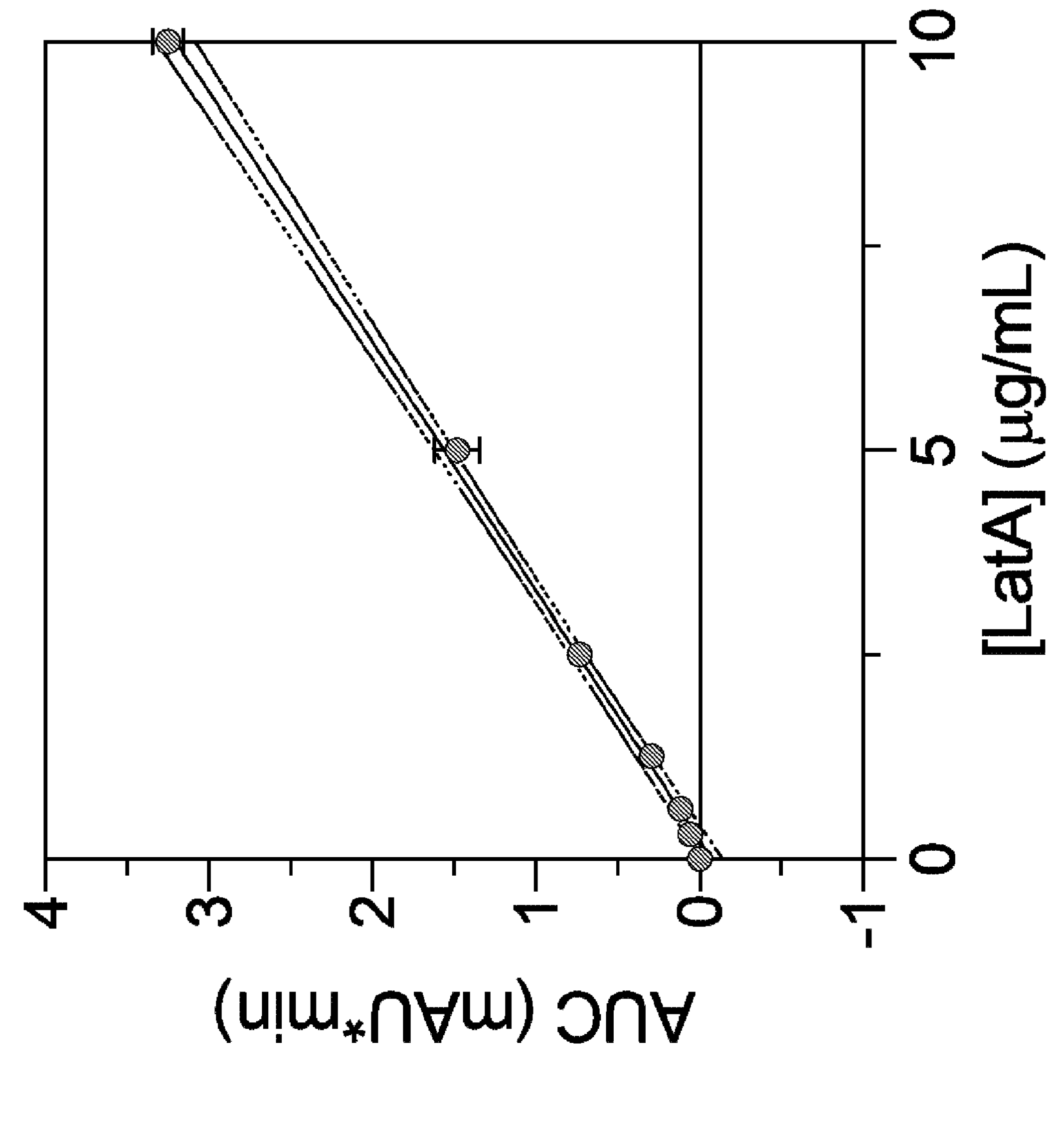
FIG. 19 shows the latrunculin A concentration series used for calibrating HPLC measurements. A representative calibration curve is displayed for a latrunculin A concentration series prepared in methanol (0.0, 0.306, 0.612, 1.25, 2.5, 5.0, 10.0 μg/mL). The area under the curve (AUC) was obtained from three replicates (n=3). The mean±s.e.m. is displayed with the 95% confidence bands. Where error bars are not displayed, the error is so small that the bars would not be visible. A linear regression model was fit to the data: $y=0.3273x-0.06997$, $r^2=0.99$.

Quantification of loaded drug concentration. Aliquots of purified LatA-loaded MC formulations were frozen at −80° C. and were lyophilized overnight. The resulting powder was resuspended in methanol and was placed at −20° C. for 1 h. Samples were centrifuged at 4,000×g for 5 min to sediment the polymer. After this extraction procedure, the supernatant (containing drug) was collected for further analysis. The concentration of LatA was determined using high performance liquid chromatography (HPLC) calibrated against a concentration series of LatA prepared in methanol (FIG. 19). The absorption of 235 nm light was measured. Data was acquired from three replicates. HPLC was performed using a C18 XDB-Eclipse column (Agilent) and a static methanol:water (95:5) mobile phase.

Protease protection assay for examining the biochemical accessibility of targeting peptides. PEG-b-PPS micelle nanocarriers displaying PG6, PG24, or PG48 at 5% molar ratio were incubated with trypsin gold protease (Promega) at 37° C., 80 rpm for 10 h. A peptide concentration of 40 nM and enzyme concentration of 800 nM (1:20 ratio) was used in these experiments. Reaction aliquots were quenched in 2% formic acid at the specified timepoints. Quenched reaction aliquots were mixed 1:1 with 50:50 methanol/acetonitrile with 0.1% trifloroacetic acid (TFA), and a saturating quantity of α-Cyano-4-hydroxycinnamic acid (Sigma) matrix. Samples were applied to 384-spot polished stainless-steel plates and were dried under hot air using a heat gun. Data was acquired using matrix assisted laser desorption ionization time-of-flight mass spectrometry (MALDI-TOF) using a Bruker rapifleX MALDI Tissuetyper TOF MS instrument.

Primary cell culture. Normal and glaucomatous Schlemm's canal endothelial cells were isolated from post-mortem human eyes obtained from BioSight (Table 2) and were cultured using established procedures[46,47]. Human umbilical vein endothelial cells (HUVECs) from pooled donors were purchased from Lonza, Ltd. The passage number of all primary cells used in these studies was less than six. Schlemm's canal cells were cultured in low glucose DMEM (Gibco) supplemented with 10% fetal bovine serum and 1× penicillin-streptomycin-glutamine (Gibco). HUVECs were cultured in endothelial cell growth basal medium-2 (EBM-2; Lonza) supplemented with FBS and an EGM-2 BulletKit (Lonza) optimized for HUVEC culture. All cells were cultured at 37° C., 5% $CO_2$ in T25 or T75 flasks.

Quantification of FLT4/VEGFR3 expression by flow cytometry. Schlemm's canal (SC) cells, glaucomatous Schlemm's canal cells (SCg), or HUVECs (n=3) were seeded in 24-well plates at a density of 100,000 cells per well. Cells were cultured in their appropriate media types (described elsewhere in this methods section) and were allowed to adhere overnight at 37° C., 5% $CO_2$. On the following day, media was aspirated, cells were washed with PBS, and single cell suspensions were prepared following established procedures[34,48]. Cell pellets were resuspended in cell staining buffer with zombie aqua cell viability stain (BioLegend), were incubated at 4° C. for 15 minutes, and were washed with cell staining buffer. After a subsequent blocking step, cells were incubated with an APC-conjugated anti-human VEGFR3 (FLT4) antibody (BioLegend) for 20 minutes at 4° C. and were then subjected to two iterative rounds of washing (and centrifugation) per manufacturer recommendations. Cells were fixed using a paraformaldehyde cell-fixation buffer (BioLegend). Flow cytometry was performed using a BD LSRFortessa Flow Cytometer. Cytobank software[49] was used to analyze the acquired data.

Live cell imaging by high-throughput widefield fluorescence microscopy. Schlemm's canal (SC) cells, glaucomatous Schlemm's canal (SCg) cells, or HUVECs (n=3) were seeded in glass-bottom 96-well plates (Greiner) at a seeding density of 25,000 cells/well, and were placed at 37° C., 5% $CO_2$ overnight. Cells were washed, blocked, and were then placed in media containing APC-conjugated anti-human FLT4/VEGFR3 antibody (BioLegend) for 30 minutes at 37° C. Afterwards, the media was removed by aspiration and cells were gently washed twice with fresh media. After the final wash step, cells were treated with media supplemented with cell-permeant NucBlue (Hoechst 33342) counterstain to visualize cell nuclei. High-throughput widefield fluorescence microscopy was performed using an ImageXpress High Content Imager (Molecular Devices). Images of live cells were acquired at 40× magnification in brightfield, DAPI, and Cy5 channels.

Nanocarrier uptake studies. Schlemm's canal cells or HUVECs were seeded at a density of 100,000 cells/well in 48-well plates and were allowed to adhere overnight at 37° C., 5% $CO_2$. Cells were treated with the specified DiI-loaded MC formulations (0.5 mg/mL polymer) for 2 h at 37° C., 5% $CO_2$. All experiments included untreated cells and a PBS-treatment group, as well as three biological replicates per treatment group (n=3). MC uptake was quantified by flow cytometry using a BD LSRFortessa Flow Cytometer and the acquired data was analyzed using Cytobank software[49]. The median fluorescence intensity (MFI) above PBS-treated background was calculated to remove cellular autofluorescence contributions to the measured values.

Longitudinal evaluation of intraocular pressure (IOP) in vivo. The mice were anesthetized with ketamine (60 mg/kg) and xylazine (6 mg/kg). IOP was measured using rebound tonometry (TonoLab; Icare) immediately upon cessation of movement (i.e., in light sleep). Each recorded IOP was the average of six measurements, giving a total of 36 rebounds from the same eye per recorded IOP value. IOP was measured three times prior to nanocarrier treatment and 24, 30, 48, 72, and 96 h following nanoparticle injection. A total of nine mice were used for the 0-48 h timepoints. Four mice and three mice were carried through the 72 h and 96 h timepoints, respectively.

Intracameral injection of nanocarrier formulations. For IOP studies, three-month-old female C57 mice were anesthetized with an intraperitoneal injection of ketamine (100 mg/kg) and xylazine (10 mg/kg). A drop of 0.5% proparacaine, a topical anesthetic, was applied to both eyes. Two pulled microglass needles filled with nanocarrier formulation (labeled "A" or "B") and connected to a pump were alternatively inserted into both mouse anterior chambers. A volume of 2 μL of nanocarrier formulation "A" or "B" containing 18 μM LatA was infused into the anterior chamber of contralateral mouse eyes at a rate of 0.67 μL/min. Thus, this procedure delivered 15.2 ng of LatA per eye. After infusion, the needles were withdrawn, and topical erythromycin antibiotic ointment was applied to both eyes. All the mice were maintained on a warm water-circulating blanket until they had recovered from the anesthesia and the animals were subsequently returned to the animal housing rack. Unmasking of treatment identity occurred after all IOP measurements were recorded.

Confocal microscopy. Mouse eyes were dissected into 8 radial wedges. Each wedge was immersed in Vectashield® mounting media containing DAPI (Vector Laboratories) in a glass-bottom dish and were imaged along one of the two sagittal planes using a Zeiss LSM 700 confocal microscope (Carl Zeiss). The uninjected contralateral eyes were used as negative control. Single images and tiles images were acquired using a 20× objective to capture either Schlemm's canal and its surrounding structures or the entire sagittal plane, using the ZEN2010 operating software (Carl Zeiss).

Statistical analysis. Statistical analyses were performed using Prism software (version 9.0.0; GraphPad Prism Software, LLC). Details of each statistical analysis are provided in the Brief Description of the Drawings.

Dynamic light scattering (DLS) and electrophoretic light scattering (ELS). The number average diameter and polydispersity index (PDI) of nanocarriers was determined by DLS using a Zetasizer Nano instrument (Malvern Instruments). The number average PDI was calculated using a custom MATLAB script (version R2019a). ELS was performed to determine zeta potential.

Cryogenic transmission electron microscopy (Cryo-TEM). Copper grids (200 mesh) with a lacey carbon membrane (EMS Cat #LC200-Cu-100) were glow-discharged in a Pelco easiGlow™ Glow Discharge Cleaning System (Ted Pella). This procedure used an atmosphere plasma generated at 15 mA for 15 seconds and a pressure of 0.24 mbar. A sample volume of 4 μL was applied to the grid. The grid was blotted for 5 seconds with a blot offset of +0.5 mm and was subsequently plunged into liquid ethane within a FEI Vitrobot Mark III plunge freezing instrument (Thermo Fisher Scientific). Specimens were imaged using a JEOL JEM1230 LaB6 emission TEM (JEOL USA) operating at 100 keV. The plunge-frozen grids were kept vitreous at −180° C. in a Gatan Cryo Transfer Holder (Model 626.6) during imaging. Images were acquired using a Gatan Orius SC1000 CCD camera (Model 831).

Fourier transform infrared (FTIR) spectroscopy. FTIR spectroscopy was performed using a Nicolet™ i S50 FTIR Spectrometer (Thermo Scientific). The background spectra for air were collected prior to obtaining measurements for the experimental samples. Spectra were obtained from liquid samples of purified PEG-b-PPS micelle formulations prepared with and without the specified targeting peptide construct (PG6, PG24, or PG48) displayed at a 5% molar ratio (peptide:polymer). Measurements were obtained in the wavenumber range of 2000-600 $cm^{-1}$ and 64 scans were collected per sample. The presence of peptide bonds was detected by analyzing the 1700-1600 $cm^{-1}$ (amide I) and 1590-1520 $cm^{-1}$ (amide II) bands.

Animals. All experiments that used animals were completed in compliance with The Association for Research in Vision and Ophthalmology (ARVO) "Statement for the Use of Animals in Ophthalmic and Vision Research". For IOP studies, mice were handled in accordance with a protocol (A001-19-01) approved by the Institutional Animal Care and Use Committee of Duke University. For confocal microscopy studies (see below) at Boston University, local Institutional Animal Care and Use Committee (IACUC) approval was obtained.

C57BL/6 (C57) mice were purchased from The Jackson Laboratory. Mice were housed and bred in clear cages and were maintained in housing rooms at 21° C. with a 12 h:12 h light:dark cycle. At Boston University, mice were housed in the Animal Science Center of Boston University Medical Campus, with a 12-hour light/12-hour dark cycle and access to food and water ad libitum. Upon arrival, mice were examined to confirm a normal appearance, i.e., free of any signs of ocular disease, and allowed to acclimatize for at least three days before experiments.

Confocal microscopy of ocular tissues. Mice (n=2) were anesthetized with 87.5 mg/kg ketamine (Henry Schein Inc.) and 12.5 mg/kg xylazine (Henry Schein Inc.) administered by intraperitoneal injection. One eye of each mouse was then injected with nanocarriers using an adapted protocol based on published procedures' for the administration of 20 nm fluorescent tracers (carboxylate-modified FluoSpheres; Invitrogen). Briefly, a 10-μL Hamilton microsyringe (Nanofil; World Precision Instruments) was loaded with 1 μL solution of nanocarriers (20 mg/mL polymer concentration), as well as 2 μL modified 4% paraformaldehyde (PFA) separated by a 0.2 μL air bubble. A 35G needle (NF35BL-2; World Precision Instruments) connected to this syringe was then inserted in the central region of the anterior chamber to uniformly distribute the injected nanocarriers. The nanocarrier injection volume was delivered at a rate of 4 nL/s using a microprocessor-based microsyringe pump controller (Micro4; World Precision Instruments). The 12 o'clock position of the eye was marked using Tissue Marking Dye (TMD; Triangle Biomedical Sciences) to provide orientation information. The nanocarriers were allowed to migrate through the anterior chamber, penetrate the trabecular meshwork, and reach Schlemm's canal for a period of 45 minutes while the needle remained in the eye. During this time, artificial tears (Henry Schein Inc.) were applied to the cornea of both eyes to prevent dehydration. A 2 μL volume of 4% paraformaldehyde (PFA) was subsequently injected into the anterior chamber while additional fixative was simultaneously applied to the exterior of the eye. After 30 minutes of fixation, both eyes were enucleated after euthanizing the mouse. The enucleated eyes were immersion-fixed in 4% PFA at 4° C. overnight, transferred to PBS, and then stored at 4° C. for further processing.

REFERENCES FOR EXAMPLE 2 AND BACKGROUND (1) Tham, Y.-C.; Li, X.; Wong, T. Y.; Quigley, H. A.; Aung, T.; Cheng, C.-Y. Global Prevalence of Glaucoma and Projections of Glaucoma Burden through 2040. *Ophthalmology* 2014, 121 (11), 2081-2090.

(2) Mao, L. K.; Stewart, W. C.; Shields, M. B. Correlation Between Intraocular Pressure Control and Progressive Glaucomatous Damage in Primary Open-Angle Glaucoma. *Am J Ophthalmol* 1991, 111 (1), 51-55.

(3) Quigley, H. A.; Nickells, R. W.; Kerrigan, L. A.; Pease, M. E.; Thibault, D. J.; Zack, D. J. Retinal Ganglion Cell Death in Experimental Glaucoma and after Axotomy Occurs by Apoptosis. *Invest Ophthalmol Vis Sci* 1995, 36 (5), 774-786.

(4) Allingham, R. R.; de Kater, A. W.; Ethier, C. R.; Anderson, P. J.; Hertzmark, E.; Epstein, D. L. The Relationship between Pore Density and Outflow Facility in Human Eyes. *Invest Ophthalmol Vis Sci* 1992, 33 (5), 1661-1669.

(5) Johnson, M.; Shapiro, A.; Ethier, C. R.; Kamm, R. D. Modulation of Outflow Resistance by the Pores of the Inner Wall Endothelium. *Invest Ophthalmol Vis Sci* 1992, 33 (5), 1670-1675.

(6) Sit, A. J.; Coloma, F. M.; Ethier, C. R.; Johnson, M. Factors Affecting the Pores of the Inner Wall Endothelium of Schlemm's Canal. *Invest Ophthalmol Vis Sci* 1997, 38 (8), 1517-1525.

(7) Ethier, C. R.; Coloma, F. M.; Sit, A. J.; Johnson, M. Two Pore Types in the Inner-Wall Endothelium of Schlemm's Canal. *Invest Ophthalmol Vis Sci* 1998, 39 (11), 2041-2048.

(8) Johnson, M.; Chan, D.; Read, A. T.; Christensen, C.; Sit, A.; Ethier, C. R. The Pore Density in the Inner Wall Endothelium of Schlemm's Canal of Glaucomatous Eyes. *Invest Ophthalmol Vis Sci* 2002, 43 (9), 2950-2955.

(9) Johnson, M. "What Controls Aqueous Humour Outflow Resistance?" *Exp Eye Res* 2006, 82 (4), 545-557.

(10) Zhou, E. H.; Krishnan, R.; Stamer, W. D.; Perkumas, K. M.; Raj endran, K.; Nabhan, J. F.; Lu, Q.; Fredberg, J. J.; Johnson, M. Mechanical Responsiveness of the Endothelial Cell of Schlemm's Canal: Scope, Variability and Its Potential Role in Controlling Aqueous Humour Outflow. *J R Soc Interface* 2012, 9 (71), 1144-1155.

(11) Braakman, S. T.; Pedrigi, R. M.; Read, A. T.; Smith, J. A. E.; Stamer, W. D.; Ethier, C. R.; Overby, D. R. Biomechanical Strain as a Trigger for Pore Formation in Schlemm's Canal Endothelial Cells. *Exp Eye Res* 2014, 127, 224-235.

(12) Overby, D. R.; Zhou, E. H.; Vargas-Pinto, R.; Pedrigi, R. M.; Fuchshofer, R.; Braakman, S. T.; Gupta, R.; Perkumas, K. M.; Sherwood, J. M.; Vahabikashi, A.; Dang, Q.; Kim, J. H.; Ethier, C. R.; Stamer, W. D.; Fredberg, J. J.; Johnson, M. Altered Mechanobiology of Schlemm's Canal Endothelial Cells in Glaucoma. *Proc Natl Acad Sci USA* 2014, 111 (38), 13876-13881.

(13) Vahabikashi, A.; Gelman, A.; Dong, B.; Gong, L.; Cha, E. D. K.; Schimmel, M.; Tamm, E. R.; Perkumas, K.; Stamer, W. D.; Sun, C.; Zhang, H. F.; Gong, H.; Johnson, M. Increased Stiffness and Flow Resistance of the Inner Wall of Schlemm's Canal in Glaucomatous Human Eyes. *Proc Natl Acad Sci USA* 2019, 116 (52), 26555-26563.

(14) Schwalbe, G. Untersuchungen über die Lymphbahnen des Auges und ihre Begrenzungen. *Archiv f. mikrosk. Anatomic* 1870, 6 (1), 261-362.

(15) Leber, Th. Studien über den Flüssigkeitswechsel im Auge. *Graefes Arhiv für Ophthalmologic* 1873, 19 (2), 87-185.

(16) Seidel, E. Weitere experimentelle Untersuchungen über die Quelle und den Verlauf der intraokularen Saftströmung. *Graefes Arhiv für Ophthalmologic* 1921, 104 (2), 284-292.

(17) Ascher, K. W. Aqueous Veins. *Am J Ophthalmol* 1942, 25 (1), 31-38.

(18) Bill, A. The Albumin Exchange in the Rabbit Eye. *Acta Physiol Scand* 1964, 60 (1-2), 18-29.

(19) Bill, A. The Drainage of Albumin from the Uvea. *Exp Eye Res* 1964, 3 (2), 179-187.

(20) Bill, A. The Aqueous Humor Drainage Mechanism in the Cynomolgus Monkey (Macaca Irus) with Evidence for Unconventional Routes. *Invest Ophthalmol* 1965, 4 (5), 911-919.

(21) Bill, A.; Hellsing, K. Production and Drainage of Aqueous Humor in the Cynomolgus Monkey (Macaca Irus). *Invest Ophthalmol* 1965, 4 (5), 920-926.

(22) Grant, W. M. Clinical Measurements of Aqueous Outflow. *AMA Arch Ophthalmol* 1951, 46 (2), 113-131.

(23) Tanna, A. P.; Johnson, M. Rho Kinase Inhibitors as a Novel Treatment for Glaucoma and Ocular Hypertension. *Ophthalmology* 2018, 125 (11), 1741-1756.

(24) Kaufman, P. L.; Bill, A.; Bárány, E. H. Effect of Cytochalasin B on Conventional Drainage of Aqueous Humor in the Cynomolgus Monkey. Exp. *Eye Res.* 1977, 25 *Suppl,* 411-414.

(25) Peterson, J. A.; Tian, B.; Bershadsky, A. D.; Volberg, T.; Gangnon, R. E.; Spector, I.; Geiger, B.; Kaufman, P. L. Latrunculin-A Increases Outflow Facility in the Monkey. *Invest Ophthalmol Vis Sci* 1999, 40 (5), 931-941.

(26) Peterson, J. A.; Tian, B.; Geiger, B.; Kaufman, P. L. Effect of Latrunculin-B on Outflow Facility in Monkeys. *Exp Eye Res* 2000, 70 (3), 307-313.

(27) Levy, B.; Ramirez, N.; Novack, G. D.; Kopczynski, C. Ocular Hypotensive Safety and Systemic Absorption of AR-13324 Ophthalmic Solution in Normal Volunteers. *Am J Ophthalmol* 2015, 159 (5), 980-985.e1.

(28) Bacharach, J.; Dubiner, H. B.; Levy, B.; Kopczynski, C. C.; Novack, G. D. Double-Masked, Randomized, Dose—Response Study of AR-13324 versus Latanoprost in Patients with Elevated Intraocular Pressure. *Ophthalmology* 2015, 122 (2), 302-307.

(29) Lewis, R. A.; Levy, B.; Ramirez, N.; Kopczynski, C. C.; Usner, D. W.; Novack, G. D.; Group, for the P.-C. S. Fixed-Dose Combination of AR-13324 and Latanoprost: A Double-Masked, 28-Day, Randomised, Controlled Study in Patients with Open-Angle Glaucoma or Ocular Hypertension. *Br J Ophthalmol* 2016, 100 (3), 339-344.

(30) Serle, J. B.; Katz, L. J.; McLaurin, E.; Heah, T.; Ramirez-Davis, N.; Usner, D. W.; Novack, G. D.; Kopczynski, C. C. Two Phase 3 Clinical Trials Comparing the Safety and Efficacy of Netarsudil to Timolol in Patients With Elevated Intraocular Pressure: Rho Kinase Elevated IOP Treatment Trial 1 and 2 (ROCKET-1 and ROCKET-2). *Am J Ophthalmol* 2018, 186, 116-127.

(31) Kahook, M. Y.; Serle, J. B.; Mah, F. S.; Kim, T.; Raizman, M. B.; Heah, T.; Ramirez-Davis, N.; Kopczynski, C. C.; Usner, D. W.; Novack, G. D.; ROCKET-2 Study Group. Long-Term Safety and Ocular Hypotensive Efficacy Evaluation of Netarsudil Ophthalmic Solution: Rho Kinase Elevated IOP Treatment Trial (ROCKET-2). *Am J Ophthalmol* 2019, 200, 130-137.

(32) Asrani, S.; Robin, A. L.; Serle, J. B.; Lewis, R. A.; Usner, D. W.; Kopczynski, C. C.; Heah, T.; Ackerman, S. L.; Alpern, L. M.; Asrani, S.; Bashford, K.; Bluestein, E. C.; Boyce, J. D.; Branch, J. D.; Brubaker, J. W.; Christie, W. C.; Cohen, J. S.; Collins, N. M.; Corin, S. M.; Daynes, T. E.; Depenbusch, M.; Dixon, E.-R.; Duzman, E.; Flowers, B. E.; Flynn, W. J.; Fong, R.; Gira, J. P.; Goldberg, D. F.; Greene, B.; Han, S. B.; Henderson, T. T.; Jerkins, G.; Jong, K. Y.; Katzen, L. B.; Khemsara, V.; Klugo, K. L.; Kozlovsky, J. F.; Leonardo, D.; Liu, Y.; LoBue, T. D.; Luchs, J. I.; Malhotra, R. P.; Mays, A.; McLaurin, E. B.; McMenemy, M. G.; Modi, S.; Moroi, S.; Mulaney, J.; Nagi, K.; Nicolau, J.; Parikh, M.; Patel, J. R.; Peplinski, L. S.; Perez, B. R.; Piltz-Seymour, J.; Sadri, E.; Saltzmann, R. M.; Schenker, H. I.; Swanic, M. J.; Tekwani, N.; Teymoorian, S.; Thomas, J. W.; Tyson, F. C.; Vold, S.; Weiss, M. J.; Zaman, F. Netarsudil/Latanoprost Fixed-Dose Combination for Elevated Intraocular Pressure: Three-Month Data from a Randomized Phase 3 Trial. *Am J Ophthalmol* 2019, 207, 248-257.

(33) Tanihara, H.; Inoue, T.; Yamamoto, T.; Kuwayama, Y.; Abe, H.; Araie, M.; K-115 Clinical Study Group. Phase 2 Randomized Clinical Study of a Rho Kinase Inhibitor, K-115, in Primary Open-Angle Glaucoma and Ocular Hypertension. *Am J Ophthalmol* 2013, 156 (4), 731-736.

(34) Stack, T.; Vincent, M.; Vahabikashi, A.; Li, G.; Perkumas, K. M.; Stamer, W. D.; Johnson, M.; Scott, E. Targeted Delivery of Cell Softening Micelles to Schlemm's Canal Endothelial Cells for Treatment of Glaucoma. *Small* 2020, e2004205.

(35) Aspelund, A.; Tammela, T.; Antila, S.; Nurmi, H.; Leppänen, V.-M.; Zarkada, G.; Stanczuk, L.; Francois, M.; Mäkinen, T.; Saharinen, P.; Immonen, I.; Alitalo, K. The Schlemm's Canal Is a VEGF-C/VEGFR-3—Responsive Lymphatic-like Vessel. *J Clin Invest* 2014, 124 (9), 3975-3986.
(36) Patel, G.; Fury, W.; Yang, H.; Gomez-Caraballo, M.; Bai, Y.; Yang, T.; Adler, C.; Wei, Y.; Ni, M.; Schmitt, H.; Hu, Y.; Yancopoulos, G.; Stamer, W. D.; Romano, C. Molecular Taxonomy of Human Ocular Outflow Tissues Defined by Single-Cell Transcriptomics. *Proc Natl Acad Sci USA* 2020, 117 (23), 12856-12867.
(37) van Zyl, T.; Yan, W.; McAdams, A.; Peng, Y.-R.; Shekhar, K.; Regev, A.; Juric, D.; Sanes, J. R. Cell Atlas of Aqueous Humor Outflow Pathways in Eyes of Humans and Four Model Species Provides Insight into Glaucoma Pathogenesis. *Proc Natl Acad Sci USA* 2020, 117 (19), 10339-10349.
(38) Elias, D. R.; Poloukhtine, A.; Popik, V.; Tsourkas, A. Effect of Ligand Density, Receptor Density, and Nanoparticle Size on Cell Targeting. *Nanomedicine* 2013, 9 (2), 194-201
(39) Huang, Y.; Jiang, K.; Zhang, X.; Chung, E. J. The Effect of Size, Charge, and Peptide Ligand Length on Kidney Targeting by Small, Organic Nanoparticles. *Bioengineering & Transla Med* 2020, 5 (3), e10173.
(40) Boussommier-Calleja, A.; Bertrand, J.; Woodward, D. F.; Ethier, C. R.; Stamer, W. D.; Overby, D. R. Pharmacologic Manipulation of Conventional Outflow Facility in Ex Vivo Mouse Eyes. *Invest Ophthalmol Vis Sci* 2012, 53 (9), 5838-5845.
(41) Boussommier-Calleja, A.; Li, G.; Wilson, A.; Ziskind, T.; Scinteie, O. E.; Ashpole, N. E.; Sherwood, J. M.; Farsiu, S.; Challa, P.; Gonzalez, P.; Downs, J. C.; Ethier, C. R.; Stamer, W. D.; Overby, D. R. Physical Factors Affecting Outflow Facility Measurements in Mice. *Invest Ophthalmol Vis Sci* 2015, 56 (13), 8331-8339.
(42) Zhang, X.; Beckmann, L.; Miller, D. A.; Shao, G.; Cai, Z.; Sun, C.; Sheibani, N.; Liu, X.; Schuman, J.; Johnson, M.; Kume, T.; Zhang, H. F. In Vivo Imaging of Schlemm's Canal and Limbal Vascular Network in Mouse Using Visible-Light OCT. *Invest Ophthalmol Vis Sci* 2020, 61 (2), 23-23.
(43) Scott, E. A.; Stano, A.; Gillard, M.; Maio-Liu, A. C.; Swartz, M. A.; Hubbell, J. A. Dendritic Cell Activation and T Cell Priming with Adjuvant- and Antigen-Loaded Oxidation-Sensitive Polymersomes. *Biomaterials* 2012, 33 (26), 6211-6219.
(44) Yi, S.; Allen, S. D.; Liu, Y.-G.; Ouyang, B. Z.; Li, X.; Augsornworawat, P.; Thorp, E. B.; Scott, E. A. Tailoring Nanostructure Morphology for Enhanced Targeting of Dendritic Cells in Atherosclerosis. *ACS Nano* 2016, 10 (12), 11290-11303.
(45) Stack, T.; Vahabikashi, A.; Johnson, M.; Scott, E. Modulation of Schlemm's Canal Endothelial Cell Stiffness via Latrunculin Loaded Block Copolymer Micelles. *J Biomed Mater Res A* 2018, 106 (7), 1771-1779.
(46) Stamer, W. D.; Roberts, B. C.; Howell, D. N.; Epstein, D. L. Isolation, Culture, and Characterization of Endothelial Cells from Schlemm's Canal. *Invest Ophthalmol Vis Sci* 1998, 39 (10), 1804-1812.
(47) Perkumas, K. M.; Stamer, W. D. Protein Markers and Differentiation in Culture for Schlemm's Canal Endothelial Cells. *Exp Eye Res* 2012, 96 (1), 82-87.
(48) Vincent, M. P.; Bobbala, S.; Karabin, N. B.; Frey, M.; Liu, Y.; Navidzadeh, J. O.; Stack, T.; Scott, E. A. Surface Chemistry-Mediated Modulation of Adsorbed Albumin Folding State Specifies Nanocarrier Clearance by Distinct Macrophage Subsets. *Nat Commun* 2021, 12 (1), 648.
(49) Chen, T. J.; Kotecha, N. Cytobank: Providing an Analytics Platform for Community Cytometry Data Analysis and Collaboration. *Curr Top Microbiol Immunol* 2014, 377, 127-157.
(50) Kizhatil, K.; Ryan, M.; Marchant, J. K.; Henrich, S.; John, S. W. M. Schlemm's Canal Is a Unique Vessel with a Combination of Blood Vascular and Lymphatic Phenotypes That Forms by a Novel Developmental Process. *PLoS Biol* 2014, 12 (7).
(51) Vincent, M. P.; Karabin, N. B.; Allen, S. D.; Sharan, B.; Frey, M. A.; Yi, S.; Yang, Y.; Scott, E. A. The Combination of Morphology and Surface Chemistry Defines the Immunological Identity of Nanocarriers in Human Blood. *Adv Therap* 2021, 2100062.
(52) Tripathi, R. C.; Millard, C. B.; Tripathi, B. J. Protein Composition of Human Aqueous Humor: SDS-PAGE Analysis of Surgical and Post-Mortem Samples. *Exp Eye Res* 1989, 48 (1), 117-130.
(53) Kashman, Y.; Groweiss, A.; Shmueli, U. Latrunculin, a New 2-Thiazolidinone Macrolide from the Marine Sponge Latrunculia Magnifica. *Tetrahedron Lett* 1980, 21 (37), 3629-3632.
(54) Swaminathan, S. S.; Oh, D.-J.; Kang, M. H.; Ren, R.; Jin, R.; Gong, H.; Rhee, D. J. Secreted Protein Acidic and Rich in Cysteine (SPARC)-Null Mice Exhibit More Uniform Outflow. *Invest Ophthalmol Vis Sci* 2013, 54 (3), 2035-2047.
(55) Petros, R. A.; DeSimone, J. M. Strategies in the Design of Nanoparticles for Therapeutic Applications. *Nat Rev Drug Discov* 2010, 9 (8), 615-627.
(56) Yi, S.; Zhang, X.; Sangji, M. H.; Liu, Y.; Allen, S. D.; Xiao, B.; Bobbala, S.; Braverman, C. L.; Cai, L.; Hecker, P. I.; DeBerge, M.; Thorp, E. B.; Temel, R. E.; Stupp, S. I.; Scott, E. A. Surface Engineered Polymersomes for Enhanced Modulation of Dendritic Cells During Cardiovascular Immunotherapy. *Adv Funct Mater* 2019, 29 (42), 1904399.
(57) Bobbala, S.; Vincent, M. P.; Scott, E. A. Just Add Water: Hydratable, Morphologically Diverse Nanocarrier Powders for Targeted Delivery. *Nanoscale* 2021.
(58) Allen, S.; Vincent, M.; Scott, E. Rapid, Scalable Assembly and Loading of Bioactive Proteins and Immunostimulants into Diverse Synthetic Nanocarriers Via Flash Nanoprecipitation. *J Vis Exp* 2018, No. 138, e57793.
(59) Park, C. Y.; Zhou, E. H.; Tambe, D.; Chen, B.; Lavoie, T.; Dowell, M.; Simeonov, A.; Maloney, D. J.; Marinkovic, A.; Tschumperlin, D. J.; Burger, S.; Frykenberg, M.; Butler, J. P.; Stamer, W. D.; Johnson, M.; Solway, J.; Fredberg, J. J.; Krishnan, R. High-Throughput Screening for Modulators of Cellular Contractile Force. *Integr Biol* (*Camb*) 2015, 7 (10), 1318-1324.
(60) Hämäläinen, K. M.; Kananen, K.; Auriola, S.; Kontturi, K.; Urtti, A. Characterization of Paracellular and Aqueous Penetration Routes in Cornea, Conjunctiva, and Sclera. *Invest Ophthalmol Vis Sci* 1997, 38 (3), 627-634.

(61) Prausnitz, M. R.; Noonan, J. S. Permeability of Cornea, Sclera, and Conjunctiva: A Literature Analysis for Drug Delivery to the Eye. *J Pharm Sci* 1998, 87 (12), 1479-1488.

(62) Agrahari, V.; Mandal, A.; Agrahari, V.; Trinh, H. M.; Joseph, M.; Ray, A.; Hadji, H.; Mitra, R.; Pal, D.; Mitra, A. K. A Comprehensive Insight on Ocular Pharmacokinetics. *Drug Deliv Transl Res* 2016, 6 (6), 735-754.

(63) Velluto, D.; Thomas, S. N.; Simeoni, E.; Swartz, M. A.; Hubbell, J. A. PEG-b-PPS-b-PEI Micelles and PEG-b-PPS/PEG-b-PPS-b-PEI Mixed Micelles as Non-Viral Vectors for Plasmid DNA: Tumor Immunotoxicity in B16F10 Melanoma. *Biomaterials* 2011, 32 (36), 9839-9847.

(64) Wilson, A. M.; Di Polo, A. Gene Therapy for Retinal Ganglion Cell Neuroprotection in Glaucoma. *Gene Ther* 2012, 19 (2), 127-136.

(65) Choquet, H.; Wiggs, J. L.; Khawaj a, A. P. Clinical Implications of Recent Advances in Primary Open-Angle Glaucoma Genetics. *Eye* 2020, 34 (1), 29-39.

(66) Napoli, A.; Valentini, M.; Tirelli, N.; Müller, M.; Hubbell, J. A. Oxidation-Responsive Polymeric Vesicles. *Nature Materials* 2004, 3 (3), 183-189.

(67) Vasdekis, A. E.; Scott, E. A.; O'Neil, C. P.; Psaltis, D.; Hubbell, Jeffrey. A. Precision Intracellular Delivery Based on Optofluidic Polymersome Rupture. *ACS Nano* 2012, 6 (9), 7850-7857.

(68) Bobbala, S.; Allen, S. D.; Scott, E. A. Flash Nanoprecipitation Permits Versatile Assembly and Loading of Polymeric Bicontinuous Cubic Nanospheres. *Nanoscale* 2018, 10 (11), 5078-5088.

(69) Allen, S. D.; Bobbala, S.; Karabin, N. B.; Modak, M.; Scott, E. A. Benchmarking Bicontinuous Nanospheres against Polymersomes for in Vivo Biodistribution and Dual Intracellular Delivery of Lipophilic and Water-Soluble Payloads. *ACS Appl Mater Interfaces* 2018, 10 (40), 33857-33866.

(70) Bobbala, S.; Allen, S. D.; Yi, S.; Vincent, M.; Frey, M.; Karabin, N. B.; Scott, E. A. Employing Bicontinuous-to-Micellar Transitions in Nanostructure Morphology for on-Demand Photo-Oxidation Responsive Cytosolic Delivery and off—on Cytotoxicity. *Nanoscale* 2020, 12 (9), 5332-5340.

(71) Swaminathan, S. S.; Oh, D.-J.; Kang, M. H.; Ren, R.; Jin, R.; Gong, H.; Rhee, D. J. Secreted Protein Acidic and Rich in Cysteine (SPARC)-Null Mice Exhibit More Uniform Outflow. *Invest Ophthalmol Vis Sci* 2013, 54 (3), 2035-2047.

We claim:

1. A system for targeted delivery of a therapeutic agent to a Schlemm's canal (SC) endothelial cell, the system comprising:

a. a nanocarrier comprising a poly(ethylene glycol)-block-poly(propylene sulfide) (PEG-b-PPS) copolymer;

b. the therapeutic agent loaded in the nanocarrier; and c. a targeting moiety that targets SC endothelial cells incorporated into the surface of the nanocarrier;

wherein the targeting moiety comprises:

i. a peptide that specifically binds to SC endothelial cells;

ii. a polyethylene glycol (PEG) spacer comprising 48 or more units; and iii a hydrophobic anchor.

2. The system of claim 1, wherein the nanocarrier is a micelle.

3. The system of claim 1, wherein the nanocarrier has a diameter within the range of 5 nm to 60 nm.

4. The system of claim 1, wherein the nanocarrier has a diameter within the range of 100 nm to 300 nm.

5. The system of claim 1, wherein the PEG-b-PPS copolymer is a $PEG_{45}$-b-$PPS_{23}$ copolymer.

6. The system of claim 1, wherein the therapeutic agent is a cell softening agent.

7. The system of claim 6, wherein the therapeutic agent is latrunculin A.

8. The system of claim 1, wherein the peptide binds to a FLT4/VEGFR3 receptor.

9. The system of claim 8, wherein the peptide has a sequence of SEQ ID NO: 1 or a sequence having 95% sequence similarity to SEQ ID NO: 1.

10. The system of claim 1, wherein the molar ratio of the targeting moiety to the PEG-b-PPS copolymer is from 1% to 5%.

11. The system of claim 10, wherein the molar ratio of the targeting moiety to the PEG-b-PPS copolymer is 5%.

12. The system of claim 1, wherein the hydrophobic anchor is palmitoleic acid.

13. A pharmaceutical composition comprising the system of claim 1; and one or more pharmaceutically acceptable carriers.

14. A method of reducing the intraocular pressure (IOP) in a subject in need thereof, the method comprising administering to the subject a therapeutically effective amount of a pharmaceutical composition comprising the system of claim 1.

15. The method of claim 14, wherein the therapeutic agent is latrunculin A and the concentration of latrunculin A in the pharmaceutical composition is 0.05 μM-20 μM.

16. The method of claim 14, wherein the IOP is reduced by at least 35% after 24 hours from the administration.

17. A method of treating glaucoma in a subject in need thereof, the method comprising administering to the subject a therapeutically effective amount of a pharmaceutical composition comprising the system of claim 1.

18. The method of claim 17, wherein the therapeutic agent is latrunculin A and the concentration of latrunculin A in the pharmaceutical composition is 0.05 μM-20 μM.

* * * * *